US008685670B2

(12) United States Patent
Goldbaum et al.

(10) Patent No.: US 8,685,670 B2
(45) Date of Patent: Apr. 1, 2014

(54) ISOLATED CHIMERIC PROTEINS OF MODIFIED LUMAZINE SYNTHASE

(75) Inventors: Fernando Alberto Goldbaum, Buenos Aires (AR); Diego Andrés Laplagne, Buenos Aires (AR); Vanesa Zylberman, Buenos Aires (AR); Patricio Craig, Buenos Aires (AR); Paula Mercedes Berguer, Buenos Aires (AR); Natalia Ainciart, Buenos Aires (AR); Carlos Alberto Fossati, La Plata (AR); Carlos Alejandro Velikovsky, Buenos Aires (AR); Juliana Cassataro, Buenos Aires (AR); Guillermo Giambartolomei, Buenos Aires (AR)

(73) Assignee: Goldgene LLC, Buenos Aires (AR)

( * ) Notice: Subject to any disclaimer, the term of this patent is extended or adjusted under 35 U.S.C. 154(b) by 1367 days.

(21) Appl. No.: 11/569,957

(22) PCT Filed: Jun. 3, 2005

(86) PCT No.: PCT/US2005/019289
§ 371 (c)(1),
(2), (4) Date: Mar. 17, 2008

(87) PCT Pub. No.: WO2005/121330
PCT Pub. Date: Dec. 22, 2005

(65) Prior Publication Data
US 2009/0087435 A1    Apr. 2, 2009

(30) Foreign Application Priority Data

Jun. 3, 2004   (AR) ................................ P040101923

(51) Int. Cl.
| | |
|---|---|
| *C12P 21/04* | (2006.01) |
| *C12N 9/00* | (2006.01) |
| *C12N 1/20* | (2006.01) |
| *C12N 15/00* | (2006.01) |
| *A61K 38/00* | (2006.01) |
| *A61K 39/00* | (2006.01) |
| *A61K 39/02* | (2006.01) |
| *C07H 21/04* | (2006.01) |

(52) U.S. Cl.
USPC ................ 435/69.7; 435/183; 435/252.33; 435/320.1; 424/184.1; 424/190.1; 424/194.1; 514/1.1; 536/23.2

(58) Field of Classification Search
None
See application file for complete search history.

(56) References Cited

U.S. PATENT DOCUMENTS

2004/0014158 A1* 1/2004 Bacher et al. ................. 435/8
2004/0213808 A1* 10/2004 Lieberman et al. ......... 424/218.1

FOREIGN PATENT DOCUMENTS

| WO | 00/32227 A2 | 6/2000 |
|---|---|---|
| WO | 00/53229 A2 | 9/2000 |
| WO | 01/42439 A1 | 6/2001 |
| WO | 01/85208 A2 | 11/2001 |

OTHER PUBLICATIONS

Laplagne et al. Engineering of a polymeric bacterial protein as a scaffold for the multiple display of peptides, Proteins. Dec. 1, 2004;57(4):820-8.*
Sciutto et al. *Brucella* spp. lumazine synthase: a novel antigen delivery system, Vaccine. Apr. 15, 2005; 23(21): 2784-90.*
Mahairas et al. J Bacteriol. Mar. 1996;178(5):1274-82.*
Whisstock et al. Quaterly Reviews of Biophysics, 2003, "Prediction of protein function from protein sequence and structure", 36(3): 307-340.*
Sciutto et al. New approaches to improve a peptide vaccine against porcine *Taenia solium* cysticercosis, Archives of Med Res 33, 371-378, 2002, Review.*
Estein et al. The recombinant Omp31 from *Brucella melitensis* alone or associated with rough lipopolysaccharide induces protection against *Brucella ovis* infection in BALB/c mice, Microbes Infect. Feb. 2003;5(2):85-93.*
Arakawa Takeshi et al., "A plant-based cholera toxin B subunit-insulin fusion protein protects against the development of autoimmune diabetes", Nature Biotechnology., vol. 16, pp. 934-938, Oct. 1998.
Bachmann, Martin F. et al., "The Influence of Antigen Organization on B Cell Rresponsiveness", Science, vol. 262, pp. 1448-1451, Nov. 1993.
Baldi, Pablo. C. et al., "Humoral Immune Response against Lipolysaccharide and Cytoplasmic Proteins of *Brucella abortus* in Cattle Vaccinated with *B. abortus* S19 or Experimentally Infected with *Yersinia enterocolitica* Serotype 0:9", Clinical and Diagnostic and Laboratory Immunology, vol. 3, No. 4, pp. 472-476, Jul. 1996.
Baldi, P.C. et al., "Structural, functional and immunological studies on a polymeric bacterial protein", Brazilian Journal of Medical and Biological Research, vol. 33, pp. 741-747, 2000.

(Continued)

*Primary Examiner* — Iqbal H Chowdhury
(74) *Attorney, Agent, or Firm* — Sughrue Mion, PLLC

(57) ABSTRACT

Isolated chimeric proteins including up to ten copies of peptides, polypeptides or protein domains inserted in the amino termini of the *Brucella* spp. Lumazine synthase enzyme. Isolated nucleotide sequences codifying the chimeric proteins. Vectors, plasmids and transformed cells used for expressing the proteins. Monoclonal and polyclonal antibodies induced by the chimeric proteins. Hybridomas producing the monoclonal antibodies. Vaccines and pharmaceutical compounds including the chimeric proteins, nucleotide sequences and antibodies. A method to induce an immune response in higher organisms including the administration of effective amounts of the vaccines and pharmaceutical compounds. Biosensors including the chimeric proteins. Protein conjugates formed by the chimeric proteins and a ligand bound by means of covalent and noncovalent bonds. Uses of the chimeric proteins, nucleotide sequences, vectors, plasmids, transformed cells, antibodies, hybridomas, conjugates, biosensors, vaccines and pharmaceutical compounds. The quaternary structure of the chimeric proteins.

39 Claims, 42 Drawing Sheets

(56) References Cited

OTHER PUBLICATIONS

Figure 3A:
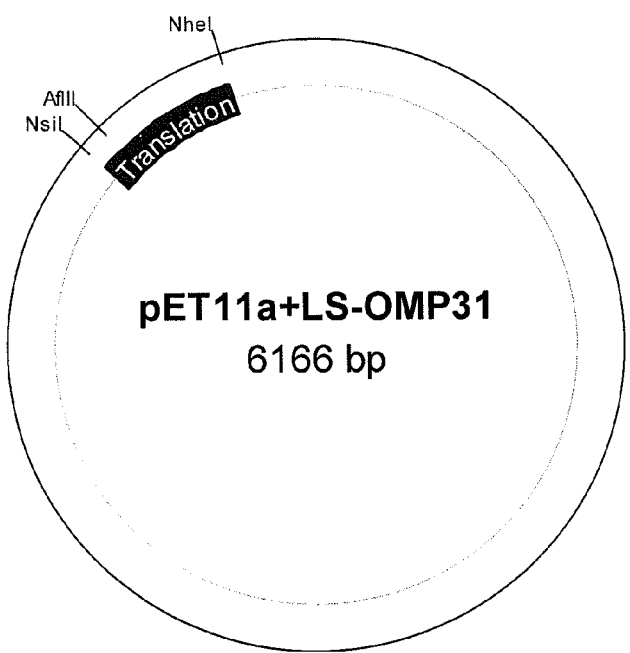

Braden, Bradford C. et al., "Divergence in Macromolecular Assembly: X-ray Crystallographic Structure Analysis of Lumazine Synthase from *Brucella abortus*", Journal of Molecular Biology, vol. 297, pp. 1031-1036, 2000.

Domingo, Gonzalo J. et al., "Multiple Display of Peptides and Proteins on a Macromolecular Scaffold Derived from a Multienzyme Complex", Journal of Molecular Biology, vol. 305, pp. 259-267, 2001.

Goldbaum, Fernando A. et al., "Differentiation between Active and Inactive Human Brucellosis by Measuring Antiprotein Humoral Immune Responses", Journal of Clinical Microbiology, vol. 30, No. 3, pp. 604-607, Mar. 1992.

Goldbaum, Fernando A. et al., "Characterization of an 18-Kilodalton *Brucella* Cytoplasmic Protein Which Appears to Be a Serological Marker of Active Infection of Both Human and Bovine Brucellosis", Journal of Clinical Microbiology, vol. 31, No. 8, pp. 2141-2145, Aug. 1993.

Goldbaum, F.A. et al., "Crystallization and Preliminary X-Ray Diffraction Analysis of the Lumazine Synthase from *Brucella abortus*", Journal of Structural Biology, vol. 123, pp. 175-178, 1998.

Goldbaum, Fernando A. et al, "The 18-kDa cytoplasmic protein of *Brucella* species—an antigen useful for diagnosis—is a lumazine synthase", Journal of Medical Microbiology, vol. 48, pp. 833-839, 1999.

Huerta, M. et al., "Synthetic peptide vaccine against *Taenia solium* pig cysticercosis: successful vaccination in a controlled field trial in rural Mexico", Vaccine, vol. 20, pp. 262-266, 2002.

Leclerc, Claude et al., "New approaches in vaccine development", Immunology Today, vol. 19, No. 7, pp. 300-302, 1998.

Li, Yu et al., The crystal structure of the C-terminal fragment of striated-muscle α-tropomyosin reveals a key troponin T recognition site, Procedings Nacional Academy of Sciences USA, vol. 99, No. 11, pp. 7378-7383, 2002.

Moll, Jonathan R. et al., "Designed heterodimerizing leucine zippers with a ranger of pIs and stabilities up to $10^{-15}$ M", Protein Science, vol. 10, pp. 649-655, 2001.

Nieba, Lars et al., "A New Generation of Vaccines", Moderns Aspects of Immunobiology, vol. 1, No. 2, pp. 36-39, 2000.

Ritsert, Karl et al., "Studies on the Lumazine Synthase/Riboflavin Synthase Complex of *Bacillus subtilis*: Crystal Structure Analysis of Reconstituted, Icosahedral β-subunit Capsids with Bound Substrate Analogue Inhibitor at 2.4 Å Resolution", Journal of Molecular Biology, vol. 253, pp. 151-167, 1995.

Toledo, Andrea et al., "Two Epitopes Shared by *Taenia crassiceps* and *Taenia solium* Confer Protection against Murine *T. crassiceps* Cysticercosis along with a Prominent T1 Response", Infection and Immunity, vol. 69, No. 3, pp. 1766-1773, Mar. 2001.

Velikovsky, Carlos A. et al., "Single-shot plasmid DNA intrasplenic immunization for the production of monoclonal antibodies Persistent Expression of DNA", J. Immunol. Meth., vol. 244, pp. 1-7, 2000.

\* cited by examiner

Figure 1

```
LS-WT:    GGA GAT ATA CAT ATG GCT AGC AAC CAA AGC TGT CCG AAC AAG ACA TCC
                          M   A   S   N   Q   S   C   P   N   K   T   S

ACEPTOR:  GGA GAT ATA CAT ATG CAT AGC AAC CAA AGC TGT CCG CTT AAG ACA TCC
                              H                           L
                          Nsi I                           Afl II
```

Figure 2

```
BLS-OMP31
     TAACGCCGGTTACGCAGGCGGCAAGTTCAAGCATCCATTTTCTAGCTTTGACAAGGAAGACAACGAACAGGTTTCCGGTTCGC
ACGTATTGCGGCCAATGCGTCCGCCGTTCAAGTTCGTAGGTAAAAGATCGAAACTGTTCCTTCTGTTGCTTGTCCAAAGGCCAAGCGAATT
     N   A   G   Y   A   G   G   K   F   K   H   P   F   S   S   F   D   K   E   D   N   E   Q   V   S   G   S
MW = 19777,5         pI = 6,00
```

Figure 3B. Complete sequence of vector pET11a with cloned BLS-OMP31 (SEQ ID NO: 23):

```
TTCTTGAAGACGAAAGGGCCTCGTGATACGCCTATTTTTATAGGTTAATGTCATGATAATAATGGTTTCTTAGACGTCAGGTGGCACTTTTCGG
GGAAATGTGCGCGGAACCCCTATTTGTTTATTTTTCTAAATACATTCAAATATGTATCCGCTCATGAGACAATAACCCTGATAAATGCTTCAAT
AATATTGAAAAAGGAAGAGTATGAGTATTCAACATTTCCGTGTCGCCCTTATTCCCTTTTTTGCGGCATTTTGCCTTCCTGTTTTTGCTCACCC
AGAAACGCTGGTGAAAGTAAAAGATGCTGAAGATCAGTTGGGTGCACGAGTGGGTTACATCGAACTGGATCTCAACAGCGGTAAGATCCTTGAG
AGTTTTCGCCCCGAAGAACGTTTTCCAATGATGAGCACTTTTAAAGTTCTGCTATGTGGCGCGGTATTATCCCGTGTTGACGCCGGGCAAGAGC
AACTCGGTCGCCGCATACACTATTCTCAGAATGACTTGGTTGAGTACTCACCAGTCACAGAAAAGCATCTTACGGATGGCATGACAGTAAGAGA
ATTATGCAGTGCTGCCATAACCATGAGTGATAACACTGCGGCCAACTTACTTCTGACAACGATCGGAGGACCGAAGGAGCTAACCGCTTTTTTG
CACAACATGGGGGATCATGTAACTCGCCTTGATCGTTGGGAACCGGAGCTGAATGAAGCCATACCAAACGACGAGCGTGACACCACGATGCCTG
CAGCAATGGCAACAACGTTGCGCAAACTATTAACTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCTGGAGCCGGTGAGCGTGGGTCTCGCGGTATCATT
GCAGCACTCGGGCCAGATGGTAAGCCCTCCCGTATCGTAGTTATCTACACGACGGGGAGTCAGGCAACTATGGATGAACGAAATAGACAGATCG
CTGAGATAGGTGCCTCACTGATTAAGCATTGGTAACTGTCAGACCAAGTTTACTCATATATACTTTAGATTGATTTAAAACTTCATTTTTAATT
TAAAAGGATCTAGGTGAAGATCCTTTTTGATAATCTCATGACCAAAATCCCTTAACGTGAGTTTTCGTTCCACTGAGCGTCAGACCCCGTAGAA
AAGATCAAAGGATCTTCTTGAGATCCTTTTTTTTCTGCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATACCAAATACTGTCCTTCTAGTGTAGCCGTAGTTAGG
CCACCACTTCAAGAACTCTGTAGCACCGCCTACATACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTATCTTTATAGTCCTGTCGGGTTTCGCCACCTCTGACTTGAGCGT
CGATTTTTGTGATGCTCGTCAGGGGGGCGGAGCCTATGGAAAAACGCCAGCAACGCGGCCTTTTTACGGTTCCTGGCCTTTTGCTGGCTTTTG
CTCACATGTTCTTTCCTGCGTTATCCCCTGATTCTGTGGATAACCGTATTACCGCCTTTGAGTGAGCTGATACCGCTCGCCGCAGCCGAACGAC
CGAGCGCAGCGAGTCAGTGAGCGAGGAAGCGGAAGAGCGCCTGATGCGGTATTTTCTCCTTACGCATCTGTGCGGTATTTCACACCGCATATAT
GGTGCACTCTCAGTACAATCTGCTCTGATGCCGCATAGTTAAGCCAGTATACACTCCGCTATCGCTACGTGACTGGGTCATGGCTGCGCCCCGA
CACCCGCCAACACCCGCTGACGCGCCCTGACGGGCTTGTCTGCTCCCGGCATCCGCTTACAGACAAGCTGTGACCGTCTCCGGGAGCTGCATGT
GTCAGAGGTTTTCACCGTCATCACCGAAACGCGCGAGGCAGCTGCGGTAAAGCTCATCAGCGTGGTCGTGAAGCGATTCACAGATGTCTGCCTG
TTCATCCGCGTCCAGCTCGTTGAGTTTCTCCAGAAGCGTTAATGTCTGGCTTCTGATAAAGCGGGCCATGTTAAGGGCGGTTTTTTCCTGTTTG
GTCACTGATGCCTCCGTGTAAGGGGGATTTCTGTTCATGGGGTAATGATACCGATGAAACGAGAGAGGATGCTCACGATACGGGTTACTGATG
ATGAACATGCCCGGTTACTGGAACGTTGTGAGGGTAAACAACTGGCGGTATGGATGCGGCGGGACCAGAGAAAAATCACTCAGGGTCAATGCCA
GCGCTTCGTTAATACAGATGTAGGTGTTCCACAGGGTAGCCAGCAGCATCCTGCGATGCAGATCCGGAACATAATGGTGCAGGGCGCTGACTTC
CGCGTTTCCAGACTTTACGAAACACGGAAACCGAAGACCATTCATGTTGTTGCTCAGGTCGCAGACGTTTTGCAGCAGCAGTCGCTTCACGTTC
GCTCGCGTATCGGTGATTCATTCTGCTAACCAGTAAGGCAACCCCGCCAGCCTAGCCGGGTCCTCAACGACAGGAGCACGATCATGCGCACCCG
TGGCCAGGACCCAACGCTGCCCGAGATGCGCCGCGTGCGGCTGCTGGAGATGGCGGACGCGATGGATATGTTCTGCCAAGGGTTGGTTTGCGCA
TTCACAGTTCTCCCGCAAGAATTGATTGGCTCCAATTCTTGGAGTGGTGAATCCGTTAGCGAGGTGCCGCCGGCTTCCATTCAGGTCGAGGTGGC
CCGGCTCCATGCACCGCGACGCAACGCGGGGAGGCAGACAAGGTATAGGGCGGCGCCTACAATCCATGCCAACCCGTTCCATGTGCTCGCCGAG
GCGGCATAAATCGCCGTGACGATCAGCGGTCCAGTGATCGAAGTTAGGCTGGTAAGAGCCGCGAGCGATCCTTGAAGCTGTCCCTGATGGTCGT
CATCTACCTGCCTGGACACGATGGCCTGCAACGCGGGCATCCCGATGCCGCCGGAAGCGAGAAGAATCATAATGGGGAAGGCCATCCAGCCTCG
CGTCGCGAACGCCAGCAAGACGTAGCCCAGCGCGTCGGCCGCCATGCCGGCGATAATGGCCTGCTTCTCGCCGAAACGTTTGGTGGCGGGACCA
GTGACGAAGGCTTGAGCGAGGGCGTGCAAGATTCCGAATACCGCAAGCGACAGGCCGATCATCGTCGCGCTCCAGCGAAAGCGGTCCTCGCCGA
AAATGACCCAGAGCGCTGCCGGCACCTGTCCTACGAGTTGCATGATAAAGAAGACAGTCATAAGTGCGGCGACGATAGTCATGCCCCGCGCCCA
CCGGAAGGAGCTGACTGGGTTGAAGGCTCTCAAGGGCATCGGTCGAGATCCCGGTGCCTAATGAGTGAGCTAACTTACATTAATTGCGTTGCGC
TCACTGCCCGCTTTCCAGTCGGGAAACCTGTCGTGCCAGCTGCATTAATGAATCGGCCAACGCGCGGGGAGAGGCGGTTTGCGTATTGGGCGCC
AGGGTGGTTTTTCTTTTCACCAGTGAGACGGGCAACAGCTGATTGCCCTTCACCGCCTGGCCCTGAGAGAGTTGCAGCAAGCGGTCCACGCTGG
TTTGCCCCAGCAGGCGAAAATCCTGTTTGATGGTGGTTAACGGCGGGATATAACATGAGCTGTCTTCGGTATCGTCGTATCCCACTACCGAGAT
ATCCGCACCAACGCGCAGCCCGGACTCGGTAATGGCGCGCATTGCGCCCAGCGCCATCTGATCGTTGGCAACCAGCATCGCAGTGGGAACGATG
CCCTCATTCAGCATTTGCATGGTTTGTTGAAAACCGGACATGGCACTCCAGTCGCCTTCCCGTTCCGCTATCGGCTGAATTTGATTGCGAGTGA
GATATTTATGCCAGCCAGCCAGACGCAGACGCGCCGAGACAGAACTTAATGGGCCCGCTAACAGCGCGATTTGCTGGTGACCCAATGCGACCAG
ATGCTCCACGCCCAGTCGCGTACCGTCTTCATGGGAGAAAATAATACTGTTGATGGGTGTCTGGTCAGAGACATCAAGAAATAACGCCGGAACA
TTAGTGCAGGCAGCTTCCACAGCAATGGCATCCTGGTCATCCAGCGGATAGTTAATGATCAGCCCACTGACGCGTTGCGCGAGAAGATTGTGCA
CCGCCGCTTTACAGGCTTCGACGCCGCTTCGTTCTACCATCGACACCACCACGCTGGCACCCAGTTGATCGGCGCGAGATTTAATCGCCGCGAC
AATTTGCGACGGCGCGTGCAGGGCCAGACTGGAGGTGGCAACGCCAATCAGCAACGACTGTTTGCCCGCCAGTTGTTGTGCCACGCGGTTGGGA
ATGTAATTCAGCTCCGCCATCGCCGCTTCCACTTTTTCCCGCGTTTTCGCAGAAACGTGGCTGGCCTGGTTCACCACGCGGGAAACGGTCTGAT
AAGAGACACCGGCATACTCTGCGACATCGTATAACGTTACTGGTTTCACATTCACCACCCTGAATTGACTCTCTTCCGGGCGCTATCATGCCAT
ACCGCGAAAGGTTTTGCGCCATTCGATGGTGTCCGGATCTCGACGCTCTCGCTTAGGAAGCAGCCCAGTAGTAGGTT
GAGGCCGTTGAGCACCGCCGCCGCAAGGAATGGTGCATGCAAGGAGATGGCGCCCAACAGTCCCCGGCCACGGGGCCTGCCACCATACCCACG
CCGAAACAAGCGCTCATGAGCCCGAAGTGGCGAGCCCGATCTTCCCCATCGGTGATGTCGGCGATATAGGCGCCAGCAACCGCACCTGTGGCGC
CGGTGATGCCGGCCACGATGCGTCCGGCGTAGAGGATCGAGATCTCGATCCCGCGAAATTAATACGACTCACTATAGGGGAATTGTGAGCGGAT
AACAATTCCCCTCTAGAAATAATTTTGTTTAACTTTAAGAAGGAGATATACATATGCATAACGCCGGTTACGCAGGCGGCAAGTTCAAGCATCC
ATTTTCTAGCTTTGACAAGGAAGACAACGAACAGGTTTCCGGTTCGCTTAAGACATCCTTTAAAATCGCATTCATTCAGGCCCGCTGGCACGCC
GACATCGTTGACGAAGCGCGCAAAAGCTTTGTCGCCGAACTGGCCGCAAAGACGGGTGGCAGCGTCGAGGTAGAGATATTCGACGTGCCGGGTG
CATATGAAATTCCCCTTCACGCCAAGACATTGGCCAGAACCGGGCGCTATGCAGCCATCGTCGGTGCGGCCTTCGTGATCGACGGCGGCATCTA
TCGTCATGATTTCGTGGCGACGGCCGTTATCAACGGCATGATGCAGGTGCAGCTTGAAACGGAAGTGCCGGTGCTGAGCGTCGTGCTGACGCCG
CACCATTTCCATGAAAGCAAGGAGCATCACGACTTCTTCCATGCTCATTTCAAGGTGAAGGGCGTGGAAGCGGCCCATGCCGCCTTGCAGATCG
TGAGCGAGCGCAGCCGCATCGCGCTTGTCTGAGCTAGCATGACTGGTGGACAGCAAATGGGTCGCGGATCCGGCTGCTAACAAAGCCCGAAAGG
AAGCTGAGTTGGCTGCTGCCACCGCTGAGCAATAACTAGCATAACCCCTTGGGGCCTCTAAACGGGTCTTGAGGGGTTTTTTGCTGAAAGGAGG
AACTATATCCGGATATCCCGCAAGAGGCCCGGCAGTACCGGCATAACCAAGCCTATGCCTACAGCATCCAGGGTGACGGTGCCGAGGATGACGA
TGAGCGCATTGTTAGATTTCATACACGGTGCCTGACTGCGTTAGCAATTTAACTGT
```

Figure 3C

BLS-OMP31 reading frame (SEQ ID NO:20):

```
Nucleotide sequence
ATGCATAACGCCGGTTACGCAGGCGGCAAGTTCAAGCATCCATTTTCTAGCTTTGACAAGGAAGACAACGAACAGGTTTCCGGT
TCGCTTAAGACATCCTTTAAAATCGCATTCATTCAGGCCCGCTGGCACGCCGACATCGTTGACGAAGCGCGCAAAAGCTTTGTC
GCCGAACTGGCCGCAAAGACGGGTGGCAGCGTCGAGGTAGAGATATTCGACGTGCCGGGTGCATATGAAATTCCCCTTCACGCC
AAGACATTGGCCAGAACCGGGCGCTATGCAGCCATCGTCGGTGCGGCCTTCGTGATCGACGGCGGCATCTATCGTCATGATTTC
GTGGCGACGGCCGTTATCAACGGCATGATGCAGGTGCAGCTTGAAACGGAAGTGCCGGTGCTGAGCGTCGTGCTGACGCCGCAC
CATTTCCATGAAAGCAAGGAGCATCACGACTTCTTCCATGCTCATTTCAAGGTGAAGGGCGTGGAAGCGGCCCATGCCGCCTTG
CAGATCGTGAGCGAGCGCAGCCGCATCGCGCTTGTCTGA
```

Aminoacid sequence (SEQ ID NO:9):

MHNAGYAGGKFKHPFSSFDKEDNEQVSGSLKTSFKIAFIQARWHADIVDEARKSFVAELAAKTGGSVEVEIFDVPGAYEIPLHA
KTLARTGRYAAIVGAAFVIDGGIYDHDFVATAVINGMMQVQLETEVPVLSVVLTPHHFHESKEHHDFFHAHFKVKGVEAAHAAL
QIVSERSRIALV

Figure 15A

Oligonucleotide sequence used to obtain the BLS-KETc1 chimera

KETc1

TGCCCCGATGAGCACGCCGAGCGCCACGAGCGTCCGCGGTAGCC

ACGTACGGGGCTACTCGTGCGGCTCGCGGTGCTCGCAGGCGCCATCGGAATT
      A  P  M  S  T  P  S  A  T  S  V  R  G  S

Figure 15B Complete sequence of vector pET11a with cloned BLS-KETc1 (SEQ ID NO: 29):

```
TTCTTGAAGACGAAAGGGCCTCGTGATACGCCTATTTTTATAGGTTAATGTCATGATAATAATGGTTTCTTAGACGTCAGGTGGCACTTTTCG
GGGAAATGTGCGCGGAACCCCTATTTGTTTATTTTTCTAAATACATTCAAATATGTATCCGCTCATGAGACAATAACCCTGATAAATGCTTCA
ATAATATTGAAAAAGGAAGAGTATGAGTATTCAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTACATCGAACTGGATCTCAACAGCGGTAAGATCCT
TGAGAGTTTTCGCCCCGAAGAACGTTTTCCAATGATGAGCACTTTTAAAGTTCTGCTATGTGGCGCGGTATTATCCCGTGTTGACGCCGGGCA
AGAGCAACTCGGTCGCCGCATACACTATTCTCAGAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGAATGAAGCCATACCAAACGACGAGCGTGACACCAC
GATGCCTGCAGCAATGGCAACAACGTTGCGCAAACTATTAACTGGCGAACTACTTACTCTAGCTTCCCGGCAACAATTAATAGACTGGATGCA
GGCGGATAAAGTTGCAGGACCACTTCTGCGCTCGGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACTTTAGATTGATTTAAAACT
TCATTTTTAATTTAAAAGGATCTAGGTGAAGATCCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTGCTGCTTGCAAACAAAAAAACCACCGCTACCAGC
GGTGGTTTGTTTGCCGGATCAAGAGCTACCAACTCTTTTTCCGAAGGTAACTGGCTTCAGCAGAGCGCAGATACCAAATACTGTCCTTCTAGT
GTAGCCGTAGTTAGGCCACCACTTCAAGAACTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGTCGGGCTGAACGGGGGGTTCGTGCACACAGCC
CAGCTTGGAGCGAACGACCTACACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATCTTTATAGTCCTGTCGGGTTTCG
CCACCTCTGACTTGAGCGTCGATTTTTGTGATGCTCGTCAGGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCTGTGGATAACCGTATTACCGCCTTTGAGTGAGCTGATAC
CGCTCGCCGCAGCCGAACGACCGAGCGCAGCGAGTCAGTGAGCGAGGAAGCGGAAGAGCGCCTGATGCGGTATTTTCTCCTTACGCATCTGTG
CGGTATTTCACACCGCATATATGGTGCACTCTCAGTACAATCTGCTCTGATGCCGCATAGTTAAGCCAGTATACACTCCGCTATCGCTACGTG
ACTGGGTCATGGCTGCGCCCCGACACCCGCCAACACCCGCTGACGCGCCCTGACGGGCTTGTCTGCTCCCGGCATCCGCTTACAGACAAGCTG
TGACCGTCTCCGGGAGCTGCATGTGTCAGAGGTTTTCACCGTCATCACCGAAACGCGCGAGGCAGCTGCGGTAAAGCTCATCAGCGTGGTCGT
GAAGCGATTCACAGATGTCTGCCTGTTCATCCGCGTCCAGCTCGTTGAGTTTCTCCAGAAGCGTTAATGTCTGGCTTCTGATAAAGCGGGCCA
TGTTAAGGGCGGTTTTTTCCTGTTTGGTCACTGATGCCTCCGTGTAAGGGGGATTTCTGTTCATGGGGGTAATGATACCGATGAAACGAGAGA
GGATGCTCACGATACGGGTTACTGATGATGAACATGCCCGGTTACTGGAACGTTGTGAGGGTAAACAACTGGCGGTATGGATGCGGCGGGACC
AGAGAAAAATCACTCAGGGTCAATGCCAGCGCTTCGTTAATACAGATGTAGGTGTTCCACAGGGTAGCCAGCAGCATCCTGCGATGCAGATCC
GGAACATAATGGTGCAGGGCGCTGACTTCCGCGTTTCCAGACTTTACGAAACACGGAAACCGAAGACCATTCATGTTGTTGCTCAGGTCGCAG
ACGTTTTGCAGCAGCAGTCGCTTCACGTTCGCTCGCGTATCGGTGATTCATTCTGCTAACCAGTAAGGCAACCCCGCCAGCCTAGCCGGGTCC
TCAACGACAGGAGCACGATCATGCGCACCCGTGGCCAGGACCCAACGCTGCCCGAGATGCGCCGCGTGCGGCTGCTGGAGATGGCGGACGCGA
TGGATATGTTCTGCCAAGGGTTGGTTTGCGCATTCACAGTTCTCCGCAAGAATTGATTGGCTCCAATTCTTGGAGTGGTGAATCCGTTAGCGA
GGTGCCGCCGGCTTCCATTCAGGTCGAGGTGGCCCGGCTCCATGCACCGCGACGCAACGCGGGGAGGCAGACAAGGTATAGGGCGGCGCCTAC
AATCCATGCCAACCCGTTCCATGTGCTCGCCGAGGCGGCATAAATCGCCGTGACGATCAGCGGTCCAGTGATCGAAGTTAGGCTGGTAAGAGC
CGCGAGCGATCCTTGAAGCTGTCCCTGATGGTCGTCATCTACCTGCCTGGACAGCATGGCCTGCAACGCGGGCATCCCGATGCCGCCGGAAGC
GAGAAGAATCATAATGGGGAAGGCCATCCAGCCTCGCGTCGCGAACGCCAGCAAGACGTAGCCCAGCGCGTCGGCCGCCATGCCGGCGATAAT
GGCCTGCTTCTCGCCGAAACGTTTGGTGGCGGGACCAGTGACGAAGGCTTGAGCGAGGGCGTGCAAGATTCCGAATACCGCAAGCGACAGCC
GATCATCGTCGCGCTCCAGCGAAAGCGGTCCTCGCCGAAAATGACCCAGAGCGCTGCCGGCACCTGTCCTACGAGTTGCATGATAAAGAAGAC
AGTCATAAGTGCGGCGACGATAGTCATGCCCCGCGCCCACCGGAAGGAGCTGACTGGGTTGAAGGCTCTCAAGGGCATCGGTCGAGATCCGG
TGCCTAATGAGTGAGCTAACTTACATTAATTGCGTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGCCAGGGTGGTTTTTCTTTTCACCAGTGAGACGGGCAACAGCTGATTGCCCTTCA
CCGCCTGGCCCTGAGAGAGTTGCAGCAAGCGGTCCACGCTGGTTTGCCCCAGCAGGCGAAAATCCTGTTTGATGGTGGTTAACGGCGGGATAT
AACATGAGCTGTCTTCGGTATCGTCGTATCCCACTACCGAGATATCCGCACCAACGCGCAGCCCGGACTCGGTAATGGCGCGCATTGCGCCCA
GCGCCATCTGATCGTTGGCAACCAGCATCGCAGTGGGAACGATGCCCTCATTCAGCATTTGCATGGTTTGTTGAAAACCGGACATGGCACTCC
AGTCGCCTTCCCGTTCCGCTATCGGCTGAATTTGATTGCGAGTGAGATATTTATGCCAGCCAGCCAGACGCAGACGCGCCGAGACAGAACTTA
ATGGGCCCGCTAACAGCGCGATTTGCTGGTGACCCAATGCGACCAGATGCTCCACGCCCAGTCGCGTACCGTCTTCATGGGAGAAAATAATAC
TGTTGATGGGTGTCTGGTCAGAGACATCAAGAAATAACGCCGGAACATTAGTGCAGGCAGCTTCCACAGCAATGGCATCCTGGTCATCCAGCG
GATAGTTAATGATCAGCCCACTGACGCGTTGCGCGAGAAGATTGTGCACCGCCGCTTTACAGGCTTCGACGCCGCTTCGTTCTACCATCGACA
CCACCACGCTGGCACCCAGTTGATCGGCGCGAGATTTAATCGCCGCGACAATTTGCGACGGCGCGTGCAGGGCCAGACTGGAGGTGGCAACGC
CAATCAGCAACGACTGTTTGCCCGCCAGTTGTTGTGCCACGCGGTTGGGAATGTAATTCAGCTCCGCCATCGCCGCTTCCACTTTTTCCCGCG
TTTTCGCAGAAACGTGGCTGGCCTGGTTCACCACGCGGGAAACGGTCTGATAAGAGACACCGGCATACTCTGCGACATCGTATAACGTTACTG
GTTTCACATTCACCACCCTGAATTGACTCTCTTCCGGGCGCTATCATGCCATACCGCGAAAGGTTTTGCGCCATTCGATGGTGTCCGGGATCT
CGACGCTCTCCCTTATGCGACTCCTGCATTAGGAAGCAGCCCAGTAGTAGGTTGAGGCCGTTGAGCACCGCCGCCGCAAGGAATGGTGCATGC
AAGGAGATGGCGCCCAACAGTCCCCCGGCCACGGGGCCTGCCACCATACCCACGCCGAAACAAGCGCTCATGAGCCCGAAGTGGCGAGCCCGA
TCTTCCCCATCGGTGATGTCGGCGATATAGGCGCCAGCAACCGCACCTGTGGCGCCGGTGATGCCGGCCACGATGCGTCCGGCGTAGAGGATC
GAGATCTCGATCCCGCGAAATTAATACGACTCACTATAGGGGAATTGTGAGCGGATAACAATTCCCCTCTAGAAATAATTTTGTTTAACTTTA
AGAAGGAGATATACATATGCATGCCCCGATGAGCACGCCGAGCGCCACGAGCGTCCGCGGTAGCCTTAAGACATCCTTTAAAATCGCATTCAT
TCAGGCCCGCTGGCACGCCGACATCGTTGACGAAGCGCGCAAAAGCTTTGTCGCGGAACTGGCCGCAAAGACGGGTGGCAGCGTCGAGGTAGA
GATATTCGACGTGCCGGGTGCATATGAAATTCCCCTTCACGCCAAGACATTGGCCAGAACCGGGCGCTATGCAGCCATCGTCGGTGCGGCCTT
CGTGATCGACGGCGGCATCTATCGTCATGATTTCGTGGCGACGGCCGTTATCAACGGCATGATGCAGGTGCAGCTTGAAACGGAAGTGCCGGT
GCTGAGCGTCGTGCTGACGCCGCACCATTTCCATGAAAGCAAGGAGCATCACGACTTCTTCCATGCTCATTTCAAGGTGAAGGGCATCGAAAGC
GGCCCATGCCGCCTTGCAGATCGTGAGCGAGCGCAGCCGCATCGCGCTTGTCTGAGCTAGCATGACTGGTGGACAGCAAATGGGTCGCGGATC
CGGCTGCTAACAAAGCCCGAAAGGAAGCTGAGTTGGCTGCTGCCACCGCTGAGCAATAACTAGCATAACCCCTTGGGGCCTCTAAACGGGTCT
TGAGGGGTTTTTTGCTGAAAGGAGGAACTATATCCGGATATCCCGCAAGAGGCCCGGCAGTACCGGCATAACCAAGCCTATGCCTACAGCATC
CAGGGTGACGGTGCCGAGGATGACGATGAGCGCATTGTTAGATTTCATACACGGTGCCTGACTGCGTTAGCAATTTAACTGT
```

Figure 15C

BLS-KETc1 reading frame:

Nucleotide sequence (SEQ ID NO:21):

```
ATGCATGCCCCGATGAGCACGCCGAGCGCCACGAGCGTCCGCGGTAGCCTTAAGACATCCTTTAAAATCGCATTCATTCAGGC
CCGCTGGCACGCCGACATCGTTGACGAAGCGCGCAAAAGCTTTGTCGCCGAACTGGCCGCAAAGACGGGTGGCAGCGTCGAGG
TAGAGATATTCGACGTGCCGGGTGCATATGAAATTCCCCTTCACGCCAAGACATTGGCCAGAACCGGGCGCTATGCAGCCATC
GTCGGTGCGGCCTTCGTGATCGACGGCGGCATCTATCGTCATGATTTCGTGGCGACGGCCGTTATCAACGGCATGATGCAGGT
GCAGCTTGAAACGGAAGTGCCGGTGCTGAGCGTCGTGCTGACGCCGCACCATTTCCATGAAAGCAAGGAGCATCACGACTTCT
TCCATGCTCATTTCAAGGTGAAGGGCGTGGAAGCGGCCCATGCCGCCTTGCAGATCGTGAGCGAGCGCAGCCGCATCGCGCTT
GTCTGA
```

Aminoacid sequence (SEQ ID NO:10):

```
MHAPMSTPSATSVRGSLKTSFKIAFIQARWHADIVDEARKSFVAELAAKTGGSVEVEIFDVPGAYEIPLHAKTLARTGRYAAI
VGAAFVIDGGIYDHDFVATAVINGMMQVQLETEVPVLSVVLTPHHFHESKEHHDFFHAHFKVKGVEAAHAALQIVSERSRIAL
V
```

Anionic interchange chromatography analysis

Figure 17A:
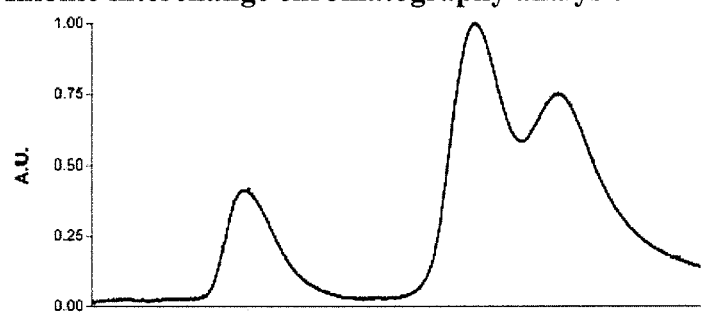

Figure 17B
SDS-PAGE/PAGE analysis
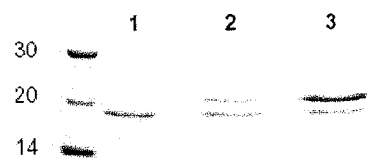
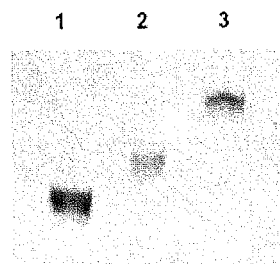

Figure 19

*In vitro* splenocyte proliferation induced by immunization with BLS-KETc1

|  | Cells from mice immunized with | |
|---|---|---|
| In vitro treatment | KETc1 | BLS-KETc1 |
| Medium | 189 ± 110 | 102 ± 82 |
| KETc1 | 379 ± 294 | 1736 ± 421* |
| BLS-KETc1 | 5686 ± 2030* | 15170 ± 2537* |

Mean ± SD of [3H] TdR incorporation (cpm) after *in vitro* stimulation of splenocytes from different strains of mice immunized with KETc1 synthetically produced or BLS-KETc1 plus saponin or saponin alone. *Significant increase in the cpm respect to splenocytes incubated with media alone ($P<0.05$).

Figure 20A *Vector pet11a with the codifying gene of the BLS-RBD3 chimera insertion in its sequence (SEQ ID NO: 30):*

TTCTTGAAGACGAAAGGGCCTCGTGATACGCCTATTTTTATAGGTTAATGTCATGATAATAATGGTTTCTTAGACGTCAGGTGGCACTTTTCG
GGGAAATGTGCGCGGAACCCCTATTTGTTTATTTTTCTAAATACATTCAAATATGTATCCGCTCATGAGACAATAACCCTGATAAATGCTTCA
ATAATATTGAAAAAGGAAGAGTATGAGTATTCAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTACATCGAACTGGATCTCAACAGCGGTAAGATCCT
TGAGAGTTTTCGCCCCGAAGAACGTTTTCCAATGATGAGCACTTTTAAAGTTCTGCTATGTGGCGCGGTATTATCCCGTGTTGACGCCGGGCA
AGAGCAACTCGGTCGCCGCATACACTATTCTCAGAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGAATGAAGCCATACCAAACGACGAGCGTGACACCAC
GATGCCTGCAGCAATGGCAACAACGTTGCGCAAACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACACGACGGGGAGTCAGGCAACTATGGATGAACGAAA
TAGACAGATCGCTGAGATAGGTGCCTCACTGATTAAGCATTGGTAACTGTCAGACCAAGTTTACTCATATATACTTTAGATTGATTTAAAACT
TCATTTTTAATTTAAAAGGATCTAGGTGAAGATCCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTGCTGCTTGCAAACAAAAAAACCACCGCTACCAGC
GGTGGTTTGTTTGCCGGATCAAGAGCTACCAACTCTTTTTCCGAAGGTAACTGGCTTCAGCAGAGCGCAGATACCAAATACTGTCCTTCTAGT
GTAGCCGTAGTTAGGCCACCACTTCAAGAACTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGTCGGGCTGAACGGGGGGTTCGTGCACACAGCC
CAGCTTGGAGCGAACGACCTACACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATCTTTATAGTCCTGTCGGGTTTCG
CCACCTCTGACTTGAGCGTCGATTTTTGTGATGCTCGTCAGGGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCTGTGGATAACCGTATTACCGCCTTTGAGTGAGCTGATAC
CGCTCGCCGCAGCCGAACGACCGAGCGCAGCGAGTCAGTGAGCGAGGAAGCGGAAGAGCGCCTGATGCGGTATTTTCTCCTTACGCATCTGTG
CGGTATTTCACACCGCATATATGGTGCACTCTCAGTACAATCTGCTCTGATGCCGCATAGTTAAGCCAGTATACACTCCGCTATCGCTACGTG
ACTGGGTCATGGCTGCGCCCCGACACCCGCCAACACCCGCTGACGCGCCCTGACGGGCTTGTCTGCTCCCGGCATCCGCTTACAGACAAGCTG
TGACCGTCTCCGGGAGCTGCATGTGTCAGAGGTTTTCACCGTCATCACCGAAACGCGCGAGGCAGCTGCGGTAAAGCTCATCAGCGTGGTCGT
GAAGCGATTCACAGATGTCTGCCTGTTCATCCGCGTCCAGCTCGTTGAGTTTCTCCAGAAGCGTTAATGTCTGGCTTCTGATAAAGCGGGCCA
TGTTAAGGGCGGTTTTTTCCTGTTTGGTCACTGATGCCTCCGTGTAAGGGGGATTTCTGTTCATGGGGGTAATGATACCGATGAAACGAGAGA
GGATGCTCACGATACGGGTTACTGATGATGAACATGCCCGGTTACTGGAACGTTGTGAGGGTAAACAACTGGCGGTATGGATGCGGCGGGACC
AGAGAAAAATCACTCAGGGTCAATGCCAGCGCTTCGTTAATACAGATGTAGGTGTTCCACAGGGTAGCCAGCAGCATCCTGCGATGCAGATCC
GGAACATAATGGTGCAGGGCGCTGACTTCCGCGTTTCCAGACTTTACGAAACACGGAAACCGAAGACCATTCATGTTGTTGCTCAGGTCGCAG
ACGTTTTGCAGCAGCAGTCGCTTCACGTTCGCTCGCGTATCGGTGATTCATTCTGCTAACCAGTAAGGCAACCCCGCCAGCCTAGCCGGGTCC
TCAACGACAGGAGCACGATCATGCGCACCCGTGGCCAGGACCCAACGCTGCCCGAGATGCGCCGCGTGCGGCTGCTGGAGATGGCGGACGCGA
TGGATATGTTCTGCCAAGGGTTGGTTTGCGCATTCACAGTTCTCCGCAAGAATTGATTGGCTCCAATTCTTGGAGTGGTGAATCCGTTAGCGA
GGTGCCGCCGGCTTCCATTCAGGTCGAGGTGGCCCGGCTCCATGCACCGCGACGCAACGCGGGGAGGCAGACAAGGTATAGGGCGGCGCCTAC
AATCCATGCCAACCCGTTCCATGTGCTCGCCGAGGCGGCATAAATCGCCGTGACGATCAGCGGTCCAGTGATCGAAGTTAGGCTGGTAAGAGC
CGCGAGCGATCCTTGAAGCTGTCCCTGATGGTCGTCATCTACCTGCCTGGACAGCATGGCCTGCAACGCGGGCATCCCGATGCCGCCGGAAGC
GAGAAGAATCATAATGGGGAAGGCCATCCAGCCTCGCGTCGCGAACGCCAGCAAGACGTAGCCCAGCGCGTCGGCCGCCATGCCGGCGATAAT
GGCCTGCTTCTCGCCGAAACGTTTGGTGGCGGGACCAGTGACGAAGGCTTGAGCGAGGGCGTGCAAGATTCCGAATACCGCAAGCGACAGGCC
GATCATCGTCGCGCTCCAGCGAAAGCGGTCCTCGCCGAAAATGACCCAGAGCGCTGCCGGCACCTGTCCTACGAGTTGCATGATAAAGAAGAC
AGTCATAAGTGCGGCGACGATAGTCATGCCCCGCGCCCACCGGAAGGAGCTGACTGGGTTGAAGGCTCTCAAGGGCATCGGTCGAGATCCCGG
TGCCTAATGAGTGAGCTAACTTACATTAATTGCGTTGCGCTCACTGCCCGCTTTCCAGTCGGGAAACCTGTCGTGCCAGCTGCATTAATGAAT
CGGCCAACGCGCGGGGAGAGGCGGTTTGCGTATTGGGCGCCAGGGTGGTTTTTCTTTTCACCAGTGAGACGGGCAACAGCTGATTGCCCTTCA
CCGCCTGGCCCTGAGAGAGTTGCAGCAAGCGGTCCACGCTGGTTTGCCCCAGCAGGCGAAAATCCTGTTTGATGGTGGTTAACGGCGGGATAT
AACATGAGCTGTCTTCGGTATCGTCGTATCCCACTACCGAGATATCCGCACCAACGCGCAGCCCGGACTCGGTAATGGCGCGCATTGCGCCCA
GCGCCATCTGATCGTTGGCAACCAGCATCGCAGTGGGAACGATGCCCTCATTCAGCATTTGCATGGTTTGTTGAAAACCGGACATGGCACTCC
AGTCGCCTTCCCGTTCCGCTATCGGCTGAATTTGATTGCGAGTGAGATATTTATGCCAGCCAGCCAGACGCAGACGCGCCGAGACAGAACTTA
ATGGGCCCGCTAACAGCGCGATTTGCTGGTGACCCAATGCGACCAGATGCTCCACGCCCAGTCGCGTACCGTCTTCATGGGAGAAAATAATAC
TGTTGATGGGTGTCTGGTCAGAGACATCAAGAAATAACGCCGGAACATTAGTGCAGGCAGCTTCCACAGCAATGGCATCCTGGTCATCCAGCG
GATAGTTAATGATCAGCCCACTGACGCGTTGCGCGAGAAGATTGTGCACCGCCGCTTTACAGGCTTCGACGCCGCTTCGTTCTACCATCGACA
CCACCACGCTGGCACCCAGTTGATCGGCGCGAGATTTAATCGCCGCGACAATTTGCGACGGCGCGTGCAGGGCCAGACTGGAGGTGGCAACGC
CAATCAGCAACGACTGTTTGCCCGCCAGTTGTTGTGCCACGCGGTTGGGAATGTAATTCAGCTCCGCCATCGCCGCTTCCACTTTTTCCCGCG
TTTTCGCAGAAACGTGGCTGGCCTGGTTCACCACGCGGGAAACGGTCTGATAAGAGACACCGGCATACTCTGCGACATCGTATAACGTTACTG
GTTTCACATTCACCACCCTGAATTGACTCTCTTCCGGGCGCTATCATGCCATACCGCGAAAGGTTTTGCGCCATTCGATGGTGTCCGGGATCT
CGACGCTCTCCCTTATGCGACTCCTGCATTAGGAAGCAGCCCAGTAGTAGGTTGAGGCCGTTGAGCACCGCCGCCGCAAGGAATGGTGCATGC
AAGGAGATGGCGCCCAACAGTCCCCCGGCCACGGGGCCTGCCACCATACCCACGCCGAAACAAGCGCTCATGAGCCCGAAGTGGCGAGCCCGA
TCTTCCCCATCGGTGATGTCGGCGATATAGGCGCCAGCAACCGCACCTGTGGCGCCGGTGATGCCGGCCACGATGCGTCCGGCGTAGAGGATC
GAGATCTCGATCCCGCGAAATTAATACGACTCACTATAGGGGAATTGTGAGCGGATAACAATTCCCCTCTAGAAATAATTTTGTTTAACTTTA
AGAAGGAGATATACATATGCATGAAAACCTCAATAAATCGGAAATAAGCCAAGTGTTTGAAATTGCGCTGAAGCGGAATTTGCCTGTGAATTT
TGAGGTGGCCCGGGAGAGTGGCCCACCACACATGAAGAACTTTGTGACCAGGGTTTCAGTTGGGGAATTTGTAGGGGAAGGAGAAGGGAAAAG
CAAGAAGATCTCCAAGAAGAATGCGGCCAGGGCTGTTCTGGAGCAGCTTAGGAGGCTGCCACTTAAGACATCCTTTAAAATCGCATTCATTCA
GGCCCGCTGGCACGCCGACATCGTTGACGAAGCGCGCAAAAGCTTTGTCGCCGAACTGGCCGCAAAGACGGGTGGCAGCGTCGAGGTAGAGAT
ATTCGACGTGCCGGGTGCATATGAAATTCCCCTTCACGCCAAGACATTGGCCAGAACCGGGCGCTATGCAGCCATCGTCGGTGCGGCCTTCGT
GATCGACGGCGGCATCTATCGTCATGATTTCGTGGCGACGGCCGTTATCAACGGCATGATGCAGGTGCAGCTTGAAACGGAAGTGCCGGTGCT
GAGCGTCGTGCTGACGCCGCACCATTTCCATGAAAGCAAGGAGCATCACGACTTCTTCCATGCTCATTTCAAGGTGAAGGGCGTGGAAGCGGC
CCATGCCGCCTTGCAGATCGTGAGCGAGCGCAGCCGCATCGCGCTTGTCTGAGCTAGCATGACTGGTGGACAGCAAATGGGTCGCGGATCCGG
CTGCTAACAAAGCCCGAAAGGAAGCTGAGTTGGCTGCTGCCACCGCTGAGCAATAACTAGCATAACCCCTTGGGGCCTCTAAACGGGTCTTGA
GGGGTTTTTTGCTGAAAGGAGGAACTATATCCGGATATCCCGCAAGAGGCCCGGCAGTACCGGCATAACCAAGCCTATGCCTACAGCATCCAG
GGTGACGGTGCCGAGGATGACGATGAGCGCATTGTTAGATTTCATACACGGTGCCTGACTGCGTTAGCAATTTAACTGTGATAAACTACCGCA
TTAAAGCTTATCGATGATAAGCTGTCAAACATGAGAA

Figure 20B

Nucleotide sequence (SEQ ID NO:22):
ATGCATGAAAACCTCAATAAATCGGAAATAAGCCAAGTGTTTGAAATTGCGCTGAAGCGGAATTTGCCTGTGAA
TTTTGAGGTGGCCCGGGAGAGTGGCCCACCACACATGAAGAACTTTGTGACCAGGGTTTCAGTTGGGGAATTTG
TAGGGGAAGGAGAAGGGAAAAGCAAGAAGATCTCCAAGAAGAATGCGGCCAGGGCTGTTCTGGAGCAGCTTAGG
AGGCTGCCACTTAAGACATCCTTTAAAATCGCATTCATTCAGGCCCGCTGGCACGCCGACATCGTTGACGAAGC
GCGCAAAAGCTTTGTCGCCGAACTGGCCGCAAAGACGGGTGGCAGCGTCGAGGTAGAGATATTCGACGTGCCGG
GTGCATATGAAATTCCCCTTCACGCCAAGACATTGGCCAGAACCGGGCGCTATGCAGCCATCGTCGGTGCGGCC
TTCGTGATCGACGGCGGCATCTATCGTCATGATTTCGTGGCGACGGCCGTTATCAACGGCATGATGCAGGTGCA
GCTTGAAACGGAAGTGCCGGTGCTGAGCGTCGTGCTGACGCCGCACCATTTCCATGAAAGCAAGGAGCATCACG
ACTTCTTCCATGCTCATTTCAAGGTGAAGGGCGTGGAAGCGGCCCATGCCGCCTTGCAGATCGTGAGCGAGCGC
AGCCGCATCGCGCTTGTC Aminoacid sequence (SEQ ID NO:11):

MHENLNKSEISQVFEIALKRNLPVNFEVARESGPPHMKNFVTRVSVGEFVGEGEGKSKKISKKNAARAVLEQLR
RLPLKTSFKIAFIQARWHADIVDEARKSFVAELAAKTGGSVEVEIFDVPGAYEIPLHAKTLARTGRYAAIVGAA
FVIDGGIYDHDFVATAVINGMMQVQLETEVPVLSVVLTPHHFHESKEHHDFFHAHFKVKGVEAAHAALQIVSER
SRIALV

Figure 23

Anti-RBD3 Reactivity

Figure 26A
Figure 26B
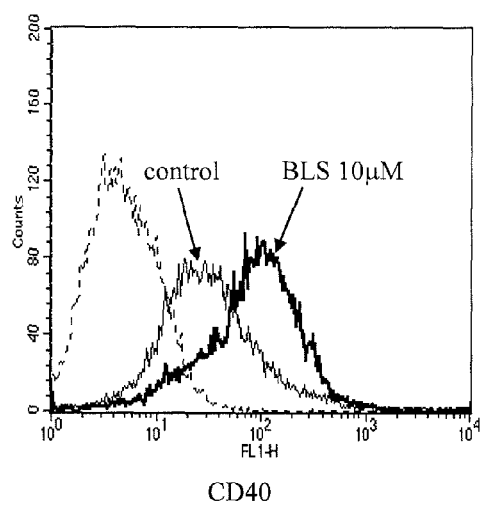
CD40
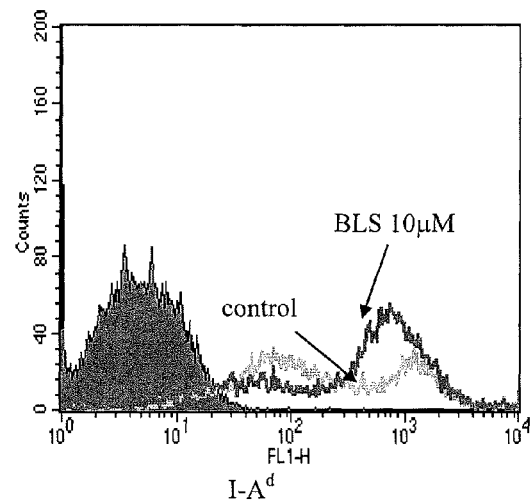
I-A$^d$

Figure 27
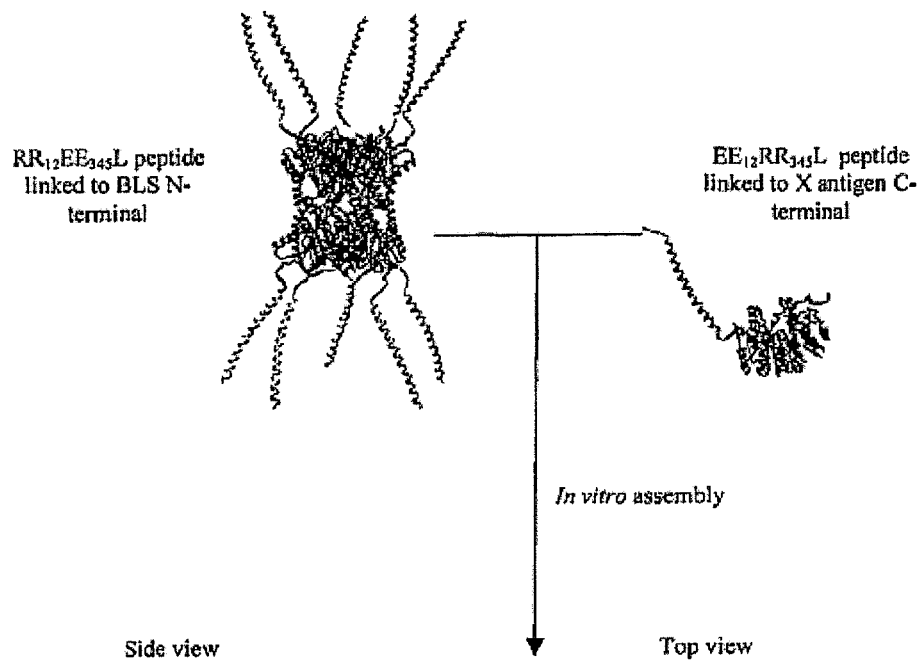
RR$_{12}$EE$_{345}$L peptide linked to BLS N-terminal
EE$_{12}$RR$_{345}$L peptide linked to X antigen C-terminal
*In vitro* assembly
Side view
Top view
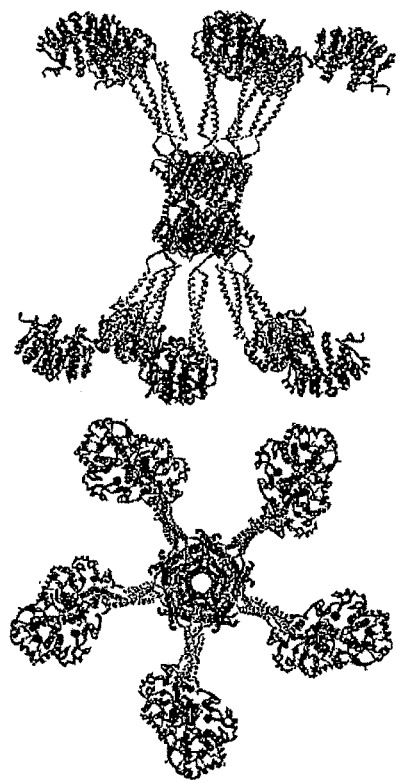

Figure 28A

```
ttcttgaagacgaaagggcctcgtgatacgcctattttttataggttaatgtcatgataataatggtttcttagacgtcaggtg
gcacttttcggggaaatgtgcgcggaaccccctatttgtttatttttctaaatacattcaaatatgtatccgctcatgagacaa
taaccctgataaatgcttcaataatattgaaaaaggaagagtatgagtattcaacatttccgtgtcgcccttattcccttttt
tgcggcatttttgccttcctgttttttgctcacccagaaacgctggtgaaagtaaaagatgctgaagatcagttgggtgcacgag
tgggttacatcgaactggatctcaacagcggtaagatccttgagagttttcgccccgaagaacgttttccaatgatgagcact
tttaaagttctgctatgtggcgcggtattatcccgtgttgacgccgggcaagagcaactcggtcgccgcatacactattctca
gaatgacttggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccacgat
gcctgcagcaatggcaacaacgttgcgcaaactattaactggcgaactacttactctagcttcccggcaacaattaatagact
ggatggaggcggataaagttgcaggaccacttctgcgctcggcccttccggctggctggtttattgctgataaatctggagcc
ggtgagcgtgggtctcgcggtatcattgcagcactggggccagatggtaagccctcccgtatcgtagttatctacacgacggg
gagtcaggcaactatggatgaacgaaatagacagatcgctgagataggtgcctcactgattaagcattggtaactgtcagacc
aagtttactcatatatactttagattgatttaaaacttcattttttaatttaaaaggatctaggtgaagatcctttttgataat
ctcatgaccaaaatcccttaacgtgagttttcgttccactgagcgtcagaccccgtagaaaagatcaaaggatcttcttgaga
tcctttttttctgcgcgtaatctgctgcttgcaaacaaaaaaaccaccgctaccagcggtggtttgtttgccggatcaagagc
taccaactctttttccgaaggtaactggcttcagcagagcgcagataccaaatactgtccttctagtgtagccgtagttaggc
caccacttcaagaactctgtagcaccgcctacatacctcgctctgctaatcctgttaccagtggctgctgccagtggcgataa
gtcgtgtcttaccgggttggactcaagacgatagttaccggataaggcgcagcggtcgggctgaacggggggttcgtgcacac
agcccagcttggagcgaacgacctacaccgaactgagatacctacagcgtgagctatgagaaagcgccacgcttcccgaaggg
agaaaggcggacaggtatccggtaagcggcagggtcggaacaggagagcgcacgagggagcttccaggggaaacgcctggta
tctttatagtcctgtcgggtttcgccacctctgacttgagcgtcgatttttgtgatgctcgtcagggggcggagcctatgga
aaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagt
gagcgaggaagcggaagagcgcctgatgcggtattttctccttacgcatctgtgcggtatttcacaccgcatatatggtgcac
tctcagtacaatctgctctgatgccgcatagttaagccagtatacactccgctatcgctacgtgactgggtcatggctgcgcc
ccgacacccgccaacacccgctgacgcgccctgacgggcttgtctgctcccggcatccgcttacagacaagctgtgaccgtct
ccgggagctgcatgtgtcagaggttttcaccgtcatcaccgaaacgcgcgaggcagctgcggtaaagctcatcagcgtggtcg
tgaagcgattcacagatgtctgcctgttcatccgcgtccagctcgttgagtttctccagaagcgttaatgtctggcttctgat
aaagcgggccatgttaagggcggttttttcctgtttggtcactgatgcctccgtgtaaggggggatttctgttcatgggggtaa
tgataccgatgaaacgagagaggatgctcacgatacgggttactgatgatgaacatgcccggttactggaacgttgtgagggt
aaacaactggcggtatggatgcggcgggaccagagaaaaatcactcaggggtcaatgccagcgcttcgttaatacagatgtagg
tgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgc
tcgcgtatcggtgattcattctgctaaccagtaaggcaaccccgccagcctagccgggtcctcaacgacaggagcacgatcat
gcgcacccgtggccaggacccaacgctgcccgagatgcgccgcgtgcggctgctggagatggcggacgcgatggatatgttct
gccaagggttggtttgcgcattcacagttctccgcaagaattgattggctccaattcttggagtggtgaatccgttagcgagg
tgccgccggcttccattcaggtcgaggtggcccggctccatgcaccgcgacgcaacgcggggaggcagacaaggtataggcg
gcgcctacaatccatgccaaccgttccatgtgctcgccgaggcggcataaatcgccgtgacgatcagcggtccagtgatcga
agttaggctggtaagagccgcgagcgatccttgaagctgtccctgatggtcgtcatctacctgcctggacagcatggcctgca
acgcgggcatcccgatgccgccggaagcgagaagaatcataatggggaaggccatccagcctcgcgtcgcgaacgccagcaag
acgtagcccagcgcgtcggccgccatgccggcgataatggcctgcttctcgccgaaacgtttggtggcgggaccagtgacgaa
ggcttgagcgagggcgtgcaagattccgaataccgcaagcgacaggccgatcatcgtcgcgctccagcgaaagcggtcctcgc
cgaaaatgacccagagcgctgccggcacctgtcctacgagttgcatgataaagaagacagtcataagtgcggcgacgatagtc
atgcccgcgcccaccggaaggagctgactgggttgaaggctctcaagggcatcggtcgagatcccgtgcctaatgagtgag
ctaacttacattaattgcgttgcgctcactgcccgctttccagtcgggaaacctgtcgtgccagctgcattaatgaatcggcc
aacgcgcggggagaggcggtttgcgtattgggcgccagggtggttttctttttcaccagtgagacgggcaacagctgattgcc
cttcaccgcctggccctgagagagttgcagcaagcggtccacgctggtttgccccagcaggcgaaaatcctgtttgatggtgg
ttaacggcgggatataacatgagctgtcttcggtatcgtcgtatcccactaccgagatatccgcaccaacgcgcagcccggac
tcggtaatggcgcgcattgcgcccagcgccatctgatcgttggcaacagcatcgcagtgggaacgatgccctcattcagcat
ttgcatggtttgttgaaaaccggacatggcactccagtcgccttcccgttccgctatcggctgaatttgattgcgagtgagat
atttatgccagccagccagacgcagacgcgccgagacagaacttaatgggcccgctaacagcgcgatttgctggtgacccaat
gcgaccagatgctccacgcccagtcgcgtaccgtcttcatgggagaaaataatactgttgatgggtgtctggtcagagacatc
aagaaataacgccggaacattagtgcaggcagcttccacagcaatggcatcctggtcatccagcggatagttaatgatcagcc
cactgacgcgttgcgcgagaagattgtgcaccgccgctttacaggcttcgacgccgcttcgttctaccatcgacaccaccacg
ctggcacccagttgatcggcgcgagatttaatgccgcgacaatttgcgacggcgcgtgcagggccagactggaggtggcaac
gccaatcagcaacgactgtttgcccgccagttgttgtgccacgcggttgggaatgtaattcagctccgccatcgccgcttcca
cttttttcccgcgttttcgcagaaacgtggctggcctggttcaccacgcgggaaacggtctgataagagacaccggcatactct
gcgacatcgtataacgttactggtttcacattcaccaccctgaattgactctcttccgggcgctatcatgccataccgcgaaa
ggttttgcgccattcgatggtgtccgggatctcgacgctctcccttatgcgactctgcattaggaagcagcccagtagtagg
ttgaggccgttgagcaccgccgccgcaaggaatggtgcatgcaaggagatggcgcccaacagtccccggccacggggcctgc
caccataccacgccgaaacaagcgctcatgagcccgaagtggcgaccgcgatcttccccatcggtgatgtcggcgatatagg
cgccagcaaccgcacctgtggcgccggtgatgccggccacgatgcgtccggcgtagaggatcgagatctcgatcccgcgaaat
taatacgactcactataggggaattgtgagcggataacaattcccctctagaaataattttgtttaactttaagaaggagata
```

FIGURE 28B

```
tacatatgcatctggaaatccgtgcggcgttcctgcgtcagcgtaacaccgcgctgcgtaccgaagttgcggaactggaacag
gaagttcagcgtctggaaaacgaagtttctcagtacgaaacccgttacggtccgctgggtggtggttctcttaagacatcctt
taaaatcgcattcattcaggcccgctggcacgccgacatcgttgacgaagcgcgcaaaagctttgtcgccgaactggccgcaa
agacgggtggcagcgtcgaggtagagatattcgacgtgccgggtgcatatgaaattcccttcacgccaagacattggccaga
accgggcgctatgcagccatcgtcggtgcggccttcgtgatcgacggcggcatctatcgtcatgatttcgtggcgacggccgt
tatcaacggcatgatgcaggtgcagcttgaaacggaagtgccggtgctgagcgtcgtgctgacgccgcaccatttccatgaaa
gcaaggagcatcacgacttcttccatgctcatttcaaggtgaagggcgtggaagcggcccatgccgccttgcagatcgtgagc
gagcgcagccgcatcgcgcttgtctgagctagcatgactggtggacagcaaatgggtcgcggatccggctgctaacaaagccc
gaaaggaagctgagttggctgctgccaccgctgagcaataactagcataacccttggggcctctaaacgggtcttgagggggt
tttttgctgaaaggaggaactatatccggatatcccgcaagaggcccggcagtaccggcataaccaagcctatgcctacagca
tccagggtgacggtgccgaggatgacgatgagcgcattgttagatttcatacacggtgcctgactgcgttagcaatttaactg
tgataaactaccgcattaaagcttatcgatgataagctgtcaaacatgagaa
```

Figure 29

Nucleotide sequence (SEQ ID NO:19):

```
atgcatctgg aaatccgtgc ggcgttcctg cgtcagcgta acaccgcgct gcgtaccgaa
gttgcggaac tggaacagga agttcagcgt ctggaaaacg aagtttctca gtacgaaacc
cgttacggtc cgctgggtgg tggttctctt aagacatcct ttaaaatcgc attcattcag
gcccgctggc acgccgacat cgttgacgaa gcgcgcaaaa gctttgtcgc cgaactggcc
gcaaagacgg gtggcagcgt cgaggtagag atattcgacg tgccgggtgc atatgaaatt
ccccttcacg ccaagacatt ggccagaacc gggcgctatg cagccatcgt cggtgcggcc
ttcgtgatcg acggcggcat ctatcgtcat gatttcgtgg cgacggccgt tatcaacggc
atgatgcagg tgcagcttga aacggaagtg ccggtgctga gcgtcgtgct gacgccgcac
catttccatg aaagcaagga gcatcacgac ttcttccatg ctcatttcaa ggtgaagggc
gtggaagcgg cccatgccgc cttgcagatc gtgagcgagc gcagccgcat cgcgcttgtc
tga
```

Amino Acid Sequence (SEQ ID NO:8):

```
MHLEIRAAFL RQRNTALRTE VAELEQEVQR LENEVSQYET RYGPLGGGKL KTSFKIAFIQ
ARWHADIVDE ARKSFVAELA AKTGGSVEVE IFDVPGAYEI PLHAKTLART GRYAAIVGAA
FVIDGGIYDH DFVATAVING MMQVQLETEV PVLSVVLTPH HFHESKEHHD FFHAHFKVKG
VEAAHAALQI VSERSRIAL V
```

Figure 32

ACGTTATCGACTGCACGGTGCACCAATGCTTCTGGCGTCAGGCAGCCATCGGAAGCTGTGGTATGGCTGTGCAGGTCGTAAATCACTGCATAA
TTCGTGTCGCTCAAGGCGCACTCCCGTTCTGGATAATGTTTTTTGCGCCGACATCATAACGGTTCTGGCAAATATTCTGAAATGAGCTGTTGA
CAATTAATCATCGGCTCGTATAATGTGTGGAATTGTGAGCGGATAACAATTTCACACAGGAAACAGTATTCATGTCCCCTATACTAGGTTATT
GGAAAATTAAGGGCCTTGTGCAACCCACTCGACTTCTTTTGGAATATCTTGAAGAAAAATATGAAGAGCATTTGTATGAGCGCGATGAAGGTG
ATAAATGGCGAAACAAAAAGTTTGAATTGGGTTTGGAGTTTCCCAATCTTCCTTATTATATTGATGGTGATGTTAAATTAACACAGTCTATGG
CCATCATACGTTATATAGCTGACAAGCACAACATGTTGGGTGGTTGTCCAAAAGAGCGTGCAGAGATTTCAATGCTTGAAGGAGCGGTTTTGG
ATATTAGATACGGTGTTTCGAGAATTGCATATAGTAAAGACTTTGAAACTCTCAAAGTTGATTTTCTTAGCAAGCTACCTGAAATGCTGAAAA
TGTTCGAAGATCGTTTATGTCATAAAACATATTTAAATGGTGATCATGTAACCCATCCTGACTTCATGTTGTATGACGCTCTTGATGTTGTTT
TATACATGGACCCAATGTGCCTGGATGCGTTCCCAAAATTAGTTTGTTTTAAAAAACGTATTGAAGCTATCCCACAAATTGATAAGTACTTGA
AATCCAGCAAGTATATAGCATGGCCTTTGCAGGGCTGGCAAGCCACGTTTGGTGGTGGCGACCATCCTCCAAAATCGGATCTGGTTCCGCGTG
GATCCCTGGAAATCGAAGCGGCGTTCCTGGAACGTGAAAACACCGCGCTGGAAACCCGTGTTGCGGAACTGCGTCAGCGTGTTCAGCGTCTGC
GTAACCGTGTTTCTCAGTACCGTACCCGTTACGGTCCGCTGGGTGGTGGTAAATGATTCTCCTGAATTCCCGGGTCGACTCGAGCGGCCGCAT
CGTGACTGACTGACGATCTGCCTCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCCGCGTCAGCGGGTGTTGGCGGGTGTCGGGCGCAGCCATGACCCAGTCACGTAGCGAT
AGCGGAGTGTATAATTCTTGAAGACGAAAGGGCCTCGTGATACGCCTATTTTTATAGGTTAATGTCATGATAATAATGGTTTCTTAGACGTCA
GGTGGCACTTTTCGGGGAAATGTGCGCGGAACCCCTATTTGTTTATTTTTCTAAATACATTCAAATATGTATCCGCTCATGAGACAATAACCC
TGATAAATGCTTCAATAATATTGAAAAAGGAAGAGTATGAGTATTCAACATTTCCGTGTCGCCCTTATTCCCTTTTTTGCGGCATTTTGCCTT
CCTGTTTTTGCTCACCCAGAAACGCTGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCTGCTATGTGGCGCGGTATTATCCCGT
GTTGACGCCGGGCAAGAGCAACTCGGTCGCCGCATACACTATTCTCAGAATGACTTGGTTGAGTACTCACCAGTCACAGAAAAGCATCTTACG
GATGGCATGACAGTAAGAGAATTATGCAGTGCTGCCATAACCATGAGTGATAACACTGCGGCCAACTTACTTCTGACAACGATCGGAGGACCG
AAGGAGCTAACCGCTTTTTTGCACAACATGGGGGATCATGTAACTCGCCTTGATCGTTGGGAACCGGAGCTGAATGAAGCCATACCAAACGAC
GAGCGTGACACCACGATGCCTGCAGCAATGGCAACAACGTTGCGCAAACTATTAACTGGCGAACTACTTACTCTAGCTTCCCGGCAACAATTA
ATAGACTGGATGGAGGCGGATAAAGTTGCAGGACCACTTCTGCGCTCGGCCCTTCCGGCTGGCTGGTTTATTGCTGATAAATCTGGAGCCGGT
GAGCGTGGGTCTCGCGGTATCATTGCAGCACTGGGGCCAGATGGTAAGCCCTCCCGTATCGTAGTTATCTACACGACGGGGAGTCAGGCAACT
ATGGATGAACGAAATAGACAGATCGCTGAGATAGGTGCCTCACTGATTAAGCATTGGTAACTGTCAGACCAAGTTTACTCATATATACTTTAG
ATTGATTTAAAACTTCATTTTTAATTTAAAAGGATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTTCTGCGCGTAATCTGCTGCTTGCAAACAAAAAAA
CCACCGCTACCAGCGGTGGTTTGTTTGCCGGATCAAGAGCTACCAACTCTTTTTCCGAAGGTAACTGGCTTCAGCAGAGCGCAGATACCAAAT
ACTGTCCTTCTAGTGTAGCCGTAGTTAGGCCACCACTTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGCACGAGGGAGCTTCCAGGGGGAAACGCCTGGTATCTTTATAGT
CCTGTCGGGTTTCGCCACCTCTGACTTGAGCGTCGATTTTTGTGATGCTCGTCAGGGGGGCGGAGCCTATGGAAAAACGCCAGCAACGCGGCC
TTTTTACGGTTCCTGGCCTTTTGCTGGCCTTTTGCTCACATGTTCTTTCCTGCGTTATCCCCTGATTCTGTGGATAACCGTATTACCGCCTTT
GAGTGAGCTGATACCGCTCGCCGCAGCCGAACGACCGAGCGCAGCGAGTCAGTGAGCGAGGAAGCGGAAGAGCGCCTGATGCGGTATTTTCTC
CTTACGCATCTGTGCGGTATTTCACACCGCATAAATTCCGACACCATCGAATGGTGCAAAACCTTTCGCGGTATGGCATGATAGCGCCCGGAA
GAGAGTCAATTCAGGGTGGTGAATGTGAAACCAGTAACGTTATACGATGTCGCAGAGTATGCCGGTGTCTCTTATCAGACCGTTTCCCGCGTG
GTGAACCAGGCCAGCCACGTTTCTGCGAAAACGCGGGAAAAAGTGGAAGCGGCGATGGCGGAGCTGAATTACATTCCCAACCGCGTGGCACAA
CAACTGGCGGGCAAACAGTCGTTGCTGATTGGCGTTGCCACCTCCAGTCTGGCCCTGCACGCGCCGTCGCAAATTGTCGCGGCGATTAAATCT
CGCGCCGATCAACTGGGTGCCAGCGTGGTGGTGTCGATGGTAGAACGAAGCGGCGTCGAAGCCTGTAAAGCGGCGGTGCACAATCTTCTCGCG
CAACGCGTCAGTGGGCTGATCATTAACTATCCGCTGGATGACCAGGATGCCATTGCTGTGGAAGCTGCCTGCACTAATGTTCCGGCGTTATTT
CTTGATGTCTCTGACCAGACACCCATCAACAGTATTATTTTCTCCCATGAAGACGGTACGCGACTGGGCGTGGAGCATCTGGTCGCATTGGGT
CACCAGCAAATCGCGCTGTTAGCGGGCCCATTAAGTTCTGTCTCGGCGCGTCTGCGTCTGGCTGGCTGGCATAAATATCTCACTCGCAATCAA
ATTCAGCCGATAGCGGAACGGGAAGGCGACTGGAGTGCCATGTCCGGTTTTCAACAAACCATGCAAATGCTGAATGAGGGCATCGTTCCCACT
GCGATGCTGGTTGCCAACGATCAGATGGCGCTGGGCGCAATGCGCGCCATTACCGAGTCCGGGCTGCGCGTTGGTGCGGATATCTCGGTAGTG
GGATACGACGATACCGAAGACAGCTCATGTTATATCCCGCCGTTAACCACCATCAAACAGGATTTTCGCCTGCTGGGGCAAACCAGCGTGGAC
CGCTTGCTGCAACTCTCTCAGGGCCAGGCGGTGAAGGGCAATCAGCTGTTGCCCGTCTCACTGGTGAAAAGAAAAACCACCCTGGCGCCCAAT
ACGCAAACCGCCTCTCCCCGCGCGTTGGCCGATTCATTAATGCAGCTGGCACGACAGGTTTCCCGACTGGAAAGCGGGCAGTGAGCGCAACGC
AATTAATGTGAGTTAGCTCACTCATTAGGCACCCCAGGCTTTACACTTTATGCTTCCGGCTCGTATGTTGTGTGGAATTGTGAGCGGATAACA
ATTTCACACAGGAAACAGCTATGACCATGATTACGGATTCACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGCCCGCACCGATCGCCCTTCCCAACAGTTGCGCAGCCTGA
ATGGCGAATGGCGCTTTGCCTGGTTTCCGGCACCAGAAGCGGTGCCGGAAAGCTGGCTGGAGTGCGATCTTCCTGAGGCCGATACTGTCGTCG
TCCCCTCAAACTGGCAGATGCACGGTTACGATGCGCCCATCTACACCAACGTAACCTATCCCATTACGGTCAATCCGCCGTTTGTTCCCACGG
AGAATCCGACGGGTTGTTACTCGCTCACATTTAATGTTGATGAAAGCTGGCTACAGGAAGGCCAGACGCGAATTATTTTTGATGGCGTTGGAA
TT

Figure 33

Nucleotide sequence:

ATGTCCCCTATACTAGGTTATTGGAAAATTAAGGGCCTTGTGCAACCCACTCGACTTCTTTTGGAATATCTTGAAGAAAAATATGAAGAGCAT
TTGTATGAGCGCGATGAAGGTGATAAATGGCGAAACAAAAAGTTTGAATTGGGTTTGGAGTTTCCCAATCTTCCTTATTATATTGATGGTGAT
GTTAAATTAACACAGTCTATGGCCATCATACGTTATATAGCTGACAAGCACAACATGTTGGGTGGTTGTCCAAAAGAGCGTGCAGAGATTTCA
ATGCTTGAAGGAGCGGTTTTGGATATTAGATACGGTGTTTCGAGAATTGCATATAGTAAAGACTTTGAAACTCTCAAAGTTGATTTTCTTAGC
AAGCTACCTGAAATGCTGAAAATGTTCGAAGATCGTTTATGTCATAAAACATATTTAAATGGTGATCATGTAACCCATCCTGACTTCATGTTG
TATGACGCTCTTGATGTTGTTTTATACATGGACCCAATGTGCCTGGATGCGTTCCCAAAATTAGTTTGTTTTAAAAAACGTATTGAAGCTATC
CCACAAATTGATAAGTACTTGAAATCCAGCAAGTATATAGCATGGCCTTTGCAGGGCTGGCAAGCCACGTTTGGTGGTGGCGACCATCCTCCA
AAATCGGATCTGGTTCCGCGTGGATCCCTGGAAATCGAAGCGGCGTTCCTGGAACGTGAAAACACCGCTGGAAACCCGTGTTGCGGAACTG
CGTCAGCGTGTTCAGCGTCTGCGTAACCGTGTTTCTCAGTACCGTACCCGTTACGGTCCGCTGGGTGGTGGTAAATGA

Amino Acid Sequence:

MSPILGYWKIKGLVQPTRLLLEYLEEKYEEHLYERDEGDKWRNKKFELGLEFPNLPYYIDGDVKLTQSMAIIRYIADKHNMLGGCPKERAEIS
MLEGAVLDIRYGVSRIAYSKDFETLKVDFLSKLPEMLKMFEDRLCHKTYLNGDHVTHPDFMLYDALDVVLYMDPMCLDAFPKLVCFKKRIEAI
PQIDKYLKSSKYIAWPLQGWQATFGGGDHPPKSDLVPRGSLEIEAAFLERENTALETRVAELRQRVQRLRNRVSQYRTRYGPLGGGK

SEQUENCE LISTING

```
<160> NUMBER OF SEQ ID NOS: 36

<210> SEQ ID NO 1
<211> LENGTH: 159
<212> TYPE: PRT
<213> ORGANISM: Artificial Sequence
<220> FEATURE:
<223> OTHER INFORMATION: synthetic lumazine synthase

<400> SEQUENCE: 1

Met His Ser Asn Gln Ser Cys Pro Leu Lys Thr Ser Phe Lys Ile Ala
1               5                   10                  15

Phe Ile Gln Ala Arg Trp His Ala Asp Ile Val Asp Glu Ala Arg Lys
            20                  25                  30

Ser Phe Val Ala Glu Leu Ala Ala Lys Thr Gly Gly Ser Val Glu Val
        35                  40                  45

Glu Ile Phe Asp Val Pro Gly Ala Tyr Glu Ile Pro Leu His Ala Lys
    50                  55                  60

Thr Leu Ala Arg Thr Gly Arg Tyr Ala Ala Ile Val Gly Ala Ala Phe
65                  70                  75                  80

Val Ile Asp Gly Gly Ile Tyr Asp His Asp Phe Val Ala Thr Ala Val
                85                  90                  95

Ile Asn Gly Met Met Gln Val Gln Leu Glu Thr Glu Val Pro Val Leu
            100                 105                 110

Ser Val Val Leu Thr Pro His His Phe His Glu Ser Lys Glu His His
        115                 120                 125
```

```
Asp Phe Phe His Ala His Phe Lys Val Lys Gly Val Glu Ala Ala His
            130                 135                 140
Ala Ala Leu Gln Ile Val Ser Glu Arg Ser Arg Ile Ala Leu Val
145                 150                 155
```

<210> SEQ ID NO 2
<211> LENGTH: 158
<212> TYPE: PRT
<213> ORGANISM: Artificial Sequence
<220> FEATURE:
<223> OTHER INFORMATION: synthetic lumazine synthase

<400> SEQUENCE: 2

```
Met His Ser Asn Gln Ser Cys Leu Lys Thr Ser Phe Lys Ile Ala Phe
1               5                   10                  15
Ile Gln Ala Arg Trp His Ala Asp Ile Val Asp Glu Ala Arg Lys Ser
            20                  25                  30
Phe Val Ala Glu Leu Ala Ala Lys Thr Gly Gly Ser Val Glu Val Glu
        35                  40                  45
Ile Phe Asp Val Pro Gly Ala Tyr Glu Ile Pro Leu His Ala Lys Thr
    50                  55                  60
Leu Ala Arg Thr Gly Arg Tyr Ala Ala Ile Val Gly Ala Ala Phe Val
65                  70                  75                  80
Ile Asp Gly Gly Ile Tyr Asp His Asp Phe Val Ala Thr Ala Val Ile
                85                  90                  95
Asn Gly Met Met Gln Val Gln Leu Glu Thr Glu Val Pro Val Leu Ser
            100                 105                 110
Val Val Leu Thr Pro His His Phe His Glu Ser Lys Glu His His Asp
        115                 120                 125
Phe Phe His Ala His Phe Lys Val Lys Gly Val Glu Ala Ala His Ala
    130                 135                 140
Ala Leu Gln Ile Val Ser Glu Arg Ser Arg Ile Ala Leu Val
145                 150                 155
```

<210> SEQ ID NO 3
<211> LENGTH: 157
<212> TYPE: PRT
<213> ORGANISM: Artificial Sequence
<220> FEATURE:
<223> OTHER INFORMATION: synthetic lumazine synthase

<400> SEQUENCE: 3

```
Met His Ser Asn Gln Ser Leu Lys Thr Ser Phe Lys Ile Ala Phe Ile
1               5                   10                  15
Gln Ala Arg Trp His Ala Asp Ile Val Asp Glu Ala Arg Lys Ser Phe
            20                  25                  30
Val Ala Glu Leu Ala Ala Lys Thr Gly Gly Ser Val Glu Val Glu Ile
        35                  40                  45
Phe Asp Val Pro Gly Ala Tyr Glu Ile Pro Leu His Ala Lys Thr Leu
    50                  55                  60
Ala Arg Thr Gly Arg Tyr Ala Ala Ile Val Gly Ala Ala Phe Val Ile
65                  70                  75                  80
Asp Gly Gly Ile Tyr Asp His Asp Phe Val Ala Thr Ala Val Ile Asn
                85                  90                  95
Gly Met Met Gln Val Gln Leu Glu Thr Glu Val Pro Val Leu Ser Val
            100                 105                 110
Val Leu Thr Pro His His Phe His Glu Ser Lys Glu His His Asp Phe
        115                 120                 125
```

```
Phe His Ala His Phe Lys Val Lys Gly Val Glu Ala Ala His Ala Ala
        130                 135                 140

Leu Gln Ile Val Ser Glu Arg Ser Arg Ile Ala Leu Val
145                 150                 155

<210> SEQ ID NO 4
<211> LENGTH: 156
<212> TYPE: PRT
<213> ORGANISM: Artificial Sequence
<220> FEATURE:
<223> OTHER INFORMATION: synthetic lumazine synthase

<400> SEQUENCE: 4

Met His Ser Asn Gln Leu Lys Thr Ser Phe Lys Ile Ala Phe Ile Gln
1               5                   10                  15

Ala Arg Trp His Ala Asp Ile Val Asp Glu Ala Arg Lys Ser Phe Val
            20                  25                  30

Ala Glu Leu Ala Ala Lys Thr Gly Gly Ser Val Glu Val Glu Ile Phe
        35                  40                  45

Asp Val Pro Gly Ala Tyr Glu Ile Pro Leu His Ala Lys Thr Leu Ala
    50                  55                  60

Arg Thr Gly Arg Tyr Ala Ala Ile Val Gly Ala Ala Phe Val Ile Asp
65                  70                  75                  80

Gly Gly Ile Tyr Asp His Asp Phe Val Ala Thr Ala Val Ile Asn Gly
                85                  90                  95

Met Met Gln Val Gln Leu Glu Thr Glu Val Pro Val Leu Ser Val Val
            100                 105                 110

Leu Thr Pro His His Phe His Glu Ser Lys Glu His His Asp Phe Phe
        115                 120                 125

His Ala His Phe Lys Val Lys Gly Val Glu Ala Ala His Ala Ala Leu
    130                 135                 140

Gln Ile Val Ser Glu Arg Ser Arg Ile Ala Leu Val
145                 150                 155

<210> SEQ ID NO 5
<211> LENGTH: 155
<212> TYPE: PRT
<213> ORGANISM: Artificial Sequence
<220> FEATURE:
<223> OTHER INFORMATION: synthetic lumazine synthase

<400> SEQUENCE: 5

Met His Ser Asn Leu Lys Thr Ser Phe Lys Ile Ala Phe Ile Gln Ala
1               5                   10                  15

Arg Trp His Ala Asp Ile Val Asp Glu Ala Arg Lys Ser Phe Val Ala
            20                  25                  30

Glu Leu Ala Ala Lys Thr Gly Gly Ser Val Glu Val Glu Ile Phe Asp
        35                  40                  45

Val Pro Gly Ala Tyr Glu Ile Pro Leu His Ala Lys Thr Leu Ala Arg
    50                  55                  60

Thr Gly Arg Tyr Ala Ala Ile Val Gly Ala Ala Phe Val Ile Asp Gly
65                  70                  75                  80

Gly Ile Tyr Asp His Asp Phe Val Ala Thr Ala Val Ile Asn Gly Met
                85                  90                  95

Met Gln Val Gln Leu Glu Thr Glu Val Pro Val Leu Ser Val Val Leu
            100                 105                 110

Thr Pro His His Phe His Glu Ser Lys Glu His His Asp Phe Phe His
        115                 120                 125
```

Ala His Phe Lys Val Lys Gly Val Glu Ala Ala His Ala Ala Leu Gln
        130                 135                 140

Ile Val Ser Glu Arg Ser Arg Ile Ala Leu Val
145                 150                 155

<210> SEQ ID NO 6
<211> LENGTH: 154
<212> TYPE: PRT
<213> ORGANISM: Artificial Sequence
<220> FEATURE:
<223> OTHER INFORMATION: synthetic lumazine synthase

<400> SEQUENCE: 6

Met His Ser Leu Lys Thr Ser Phe Lys Ile Ala Phe Ile Gln Ala Arg
1               5                   10                  15

Trp His Ala Asp Ile Val Asp Glu Ala Arg Lys Ser Phe Val Ala Glu
            20                  25                  30

Leu Ala Ala Lys Thr Gly Gly Ser Val Glu Val Glu Ile Phe Asp Val
        35                  40                  45

Pro Gly Ala Tyr Glu Ile Pro Leu His Ala Lys Thr Leu Ala Arg Thr
    50                  55                  60

Gly Arg Tyr Ala Ala Ile Val Gly Ala Ala Phe Val Ile Asp Gly Gly
65                  70                  75                  80

Ile Tyr Asp His Asp Phe Val Ala Thr Ala Val Ile Asn Gly Met Met
                85                  90                  95

Gln Val Gln Leu Glu Thr Glu Val Pro Val Leu Ser Val Val Leu Thr
            100                 105                 110

Pro His His Phe His Glu Ser Lys Glu His His Asp Phe Phe His Ala
        115                 120                 125

His Phe Lys Val Lys Gly Val Glu Ala Ala His Ala Ala Leu Gln Ile
    130                 135                 140

Val Ser Glu Arg Ser Arg Ile Ala Leu Val
145                 150

<210> SEQ ID NO 7
<211> LENGTH: 153
<212> TYPE: PRT
<213> ORGANISM: Artificial Sequence
<220> FEATURE:
<223> OTHER INFORMATION: synthetic lumazine synthase

<400> SEQUENCE: 7

Met His Leu Lys Thr Ser Phe Lys Ile Ala Phe Ile Gln Ala Arg Trp
1               5                   10                  15

His Ala Asp Ile Val Asp Glu Ala Arg Lys Ser Phe Val Ala Glu Leu
            20                  25                  30

Ala Ala Lys Thr Gly Gly Ser Val Glu Val Glu Ile Phe Asp Val Pro
        35                  40                  45

Gly Ala Tyr Glu Ile Pro Leu His Ala Lys Thr Leu Ala Arg Thr Gly
    50                  55                  60

Arg Tyr Ala Ala Ile Val Gly Ala Ala Phe Val Ile Asp Gly Gly Ile
65                  70                  75                  80

Tyr Asp His Asp Phe Val Ala Thr Ala Val Ile Asn Gly Met Met Gln
                85                  90                  95

Val Gln Leu Glu Thr Glu Val Pro Val Leu Ser Val Val Leu Thr Pro
            100                 105                 110

His His Phe His Glu Ser Lys Glu His His Asp Phe Phe His Ala His
        115                 120                 125

Phe Lys Val Lys Gly Val Glu Ala Ala His Ala Ala Leu Gln Ile Val
            130                 135                 140

Ser Glu Arg Ser Arg Ile Ala Leu Val
145                 150

<210> SEQ ID NO 8
<211> LENGTH: 200
<212> TYPE: PRT
<213> ORGANISM: Artificial Sequence
<220> FEATURE:
<223> OTHER INFORMATION: synthetic chimeric protein

<400> SEQUENCE: 8

Met His Leu Glu Ile Arg Ala Ala Phe Leu Arg Gln Arg Asn Thr Ala
1               5                   10                  15

Leu Arg Thr Glu Val Ala Glu Leu Glu Gln Glu Val Gln Arg Leu Glu
            20                  25                  30

Asn Glu Val Ser Gln Tyr Glu Thr Arg Tyr Gly Pro Leu Gly Gly Gly
        35                  40                  45

Lys Leu Lys Thr Ser Phe Lys Ile Ala Phe Ile Gln Ala Arg Trp His
    50                  55                  60

Ala Asp Ile Val Asp Glu Ala Arg Lys Ser Phe Val Ala Glu Leu Ala
65                  70                  75                  80

Ala Lys Thr Gly Gly Ser Val Glu Val Glu Ile Phe Asp Val Pro Gly
                85                  90                  95

Ala Tyr Glu Ile Pro Leu His Ala Lys Thr Leu Ala Arg Thr Gly Arg
            100                 105                 110

Tyr Ala Ala Ile Val Gly Ala Ala Phe Val Ile Asp Gly Gly Ile Tyr
        115                 120                 125

Asp His Asp Phe Val Ala Thr Ala Val Ile Asn Gly Met Met Gln Val
    130                 135                 140

Gln Leu Glu Thr Glu Val Pro Val Leu Ser Val Leu Thr Pro His His
145                 150                 155                 160

His Phe His Glu Ser Lys Glu His His Asp Phe Phe His Ala His Phe
                165                 170                 175

Lys Val Lys Gly Val Glu Ala Ala His Ala Ala Leu Gln Ile Val Ser
            180                 185                 190

Glu Arg Ser Arg Ile Ala Leu Val
        195                 200

<210> SEQ ID NO 9
<211> LENGTH: 180
<212> TYPE: PRT
<213> ORGANISM: Artificial Sequence
<220> FEATURE:
<223> OTHER INFORMATION: synthetic chimeric protein

<400> SEQUENCE: 9

Met His Asn Ala Gly Tyr Ala Gly Gly Lys Phe Lys His Pro Phe Ser
1               5                   10                  15

Ser Phe Asp Lys Glu Asp Asn Glu Gln Val Ser Gly Ser Leu Lys Thr
            20                  25                  30

Ser Phe Lys Ile Ala Phe Ile Gln Ala Arg Trp His Ala Asp Ile Val
        35                  40                  45

Asp Glu Ala Arg Lys Ser Phe Val Ala Glu Leu Ala Ala Lys Thr Gly
    50                  55                  60

Gly Ser Val Glu Val Glu Ile Phe Asp Val Pro Gly Ala Tyr Glu Ile
65                  70                  75                  80

Pro Leu His Ala Lys Thr Leu Ala Arg Thr Gly Arg Tyr Ala Ala Ile
            85                  90                  95

Val Gly Ala Ala Phe Val Ile Asp Gly Ile Tyr Asp His Asp Phe
            100                 105                 110

Val Ala Thr Ala Val Ile Asn Gly Met Met Gln Val Gln Leu Glu Thr
            115                 120                 125

Glu Val Pro Val Leu Ser Val Val Leu Thr Pro His His Phe His Glu
130                 135                 140

Ser Lys Glu His His Asp Phe Phe His Ala His Phe Lys Val Lys Gly
145                 150                 155                 160

Val Glu Ala Ala His Ala Ala Leu Gln Ile Val Ser Glu Arg Ser Arg
            165                 170                 175

Ile Ala Leu Val
            180

<210> SEQ ID NO 10
<211> LENGTH: 167
<212> TYPE: PRT
<213> ORGANISM: Artificial Sequence
<220> FEATURE:
<223> OTHER INFORMATION: synthetic chimeric protein

<400> SEQUENCE: 10

Met His Ala Pro Met Ser Thr Pro Ser Ala Thr Ser Val Arg Gly Ser
1               5                   10                  15

Leu Lys Thr Ser Phe Lys Ile Ala Phe Ile Gln Ala Arg Trp His Ala
            20                  25                  30

Asp Ile Val Asp Glu Ala Arg Lys Ser Phe Val Ala Glu Leu Ala Ala
            35                  40                  45

Lys Thr Gly Gly Ser Val Glu Val Glu Ile Phe Asp Val Pro Gly Ala
        50                  55                  60

Tyr Glu Ile Pro Leu His Ala Lys Thr Leu Ala Arg Thr Gly Arg Tyr
65                  70                  75                  80

Ala Ala Ile Val Gly Ala Ala Phe Val Ile Asp Gly Gly Ile Tyr Asp
                85                  90                  95

His Asp Phe Val Ala Thr Ala Val Ile Asn Gly Met Met Gln Val Gln
            100                 105                 110

Leu Glu Thr Glu Val Pro Val Leu Ser Val Val Leu Thr Pro His His
            115                 120                 125

Phe His Glu Ser Lys Glu His His Asp Phe Phe His Ala His Phe Lys
        130                 135                 140

Val Lys Gly Val Glu Ala Ala His Ala Ala Leu Gln Ile Val Ser Glu
145                 150                 155                 160

Arg Ser Arg Ile Ala Leu Val
                165

<210> SEQ ID NO 11
<211> LENGTH: 228
<212> TYPE: PRT
<213> ORGANISM: Artificial Sequence
<220> FEATURE:
<223> OTHER INFORMATION: synthetic chimeric protein

<400> SEQUENCE: 11

Met His Glu Asn Leu Asn Lys Ser Glu Ile Ser Gln Val Phe Glu Ile
1               5                   10                  15

Ala Leu Lys Arg Asn Leu Pro Val Asn Phe Glu Val Ala Arg Glu Ser
            20                  25                  30

```
Gly Pro Pro His Met Lys Asn Phe Val Thr Arg Val Ser Val Gly Glu
            35                  40                  45

Phe Val Gly Glu Gly Glu Gly Lys Ser Lys Lys Ile Ser Lys Lys Asn
 50                  55                  60

Ala Ala Arg Ala Val Leu Glu Gln Leu Arg Arg Leu Pro Leu Lys Thr
 65                  70                  75                  80

Ser Phe Lys Ile Ala Phe Ile Gln Ala Arg Trp His Ala Asp Ile Val
                 85                  90                  95

Asp Glu Ala Arg Lys Ser Phe Val Ala Glu Leu Ala Ala Lys Thr Gly
                100                 105                 110

Gly Ser Val Glu Val Glu Ile Phe Asp Val Pro Gly Ala Tyr Glu Ile
            115                 120                 125

Pro Leu His Ala Lys Thr Leu Ala Arg Thr Gly Arg Tyr Ala Ala Ile
        130                 135                 140

Val Gly Ala Ala Phe Val Ile Asp Gly Gly Ile Tyr Asp His Asp Phe
145                 150                 155                 160

Val Ala Thr Ala Val Ile Asn Gly Met Met Gln Val Gln Leu Glu Thr
                165                 170                 175

Glu Val Pro Val Leu Ser Val Leu Thr Pro His His Phe His Glu
            180                 185                 190

Ser Lys Glu His His Asp Phe Phe His Ala His Phe Lys Val Lys Gly
        195                 200                 205

Val Glu Ala Ala His Ala Ala Leu Gln Ile Val Ser Glu Arg Ser Arg
    210                 215                 220

Ile Ala Leu Val
225
```

<210> SEQ ID NO 12
<211> LENGTH: 480
<212> TYPE: DNA
<213> ORGANISM: Artificial Sequence
<220> FEATURE:
<223> OTHER INFORMATION: synthetic BLSm cassette

<400> SEQUENCE: 12

```
atgcatagca accaaagctg tccgcttaag acatccttta aaatcgcatt cattcaggcc      60
cgctggcacg ccgacatcgt tgacgaagcg cgcaaaagct tgtcgccga actggccgca     120
aagacgggtg gcagcgtcga ggtagagata ttcgacgtgc cgggtgcata tgaaattccc     180
cttcacgcca agacattggc cagaaccggg cgctatgcag ccatcgtcgg tgcggccttc     240
gtgatcgacg gcggcatcta cgtcatgat tcgtggcga cggccgttat caacggcatg      300
atgcaggtgc agcttgaaac ggaagtgccg gtgctgagcg tcgtgctgac gccgcaccat     360
ttccatgaaa gcaaggagca tcacgacttc ttccatgctc atttcaaggt gaagggcgtg     420
gaagcggccc atgccgcctt gcagatcgtg agcgagcgca gccgcatcgc gcttgtctga     480
```

<210> SEQ ID NO 13
<211> LENGTH: 477
<212> TYPE: DNA
<213> ORGANISM: Artificial Sequence
<220> FEATURE:
<223> OTHER INFORMATION: synthetic mutated BLS

<400> SEQUENCE: 13

```
atgcatagca accaaagctg tcttaagaca tcctttaaaa tcgcattcat tcaggcccgc      60
tggcacgccg acatcgttga cgaagcgcgc aaaagctttg tcgccgaact ggccgcaaag     120
acgggtggca gcgtcgaggt agagatattc gacgtgccgg gtgcatatga aattcccctt     180
```

```
cacgccaaga cattggccag aaccgggcgc tatgcagcca tcgtcggtgc ggccttcgtg      240
atcgacggcg gcatctatcg tcatgatttc gtggcgacgg ccgttatcaa cggcatgatg      300
caggtgcagc ttgaaacgga agtgccggtg ctgagcgtcg tgctgacgcc gcaccatttc      360
catgaaagca aggagcatca cgacttcttc catgctcatt tcaaggtgaa gggcgtggaa      420
gcggcccatg ccgccttgca gatcgtgagc gagcgcagcc gcatcgcgct tgtctga         477
```

<210> SEQ ID NO 14
<211> LENGTH: 474
<212> TYPE: DNA
<213> ORGANISM: Artificial Sequence
<220> FEATURE:
<223> OTHER INFORMATION: synthetic mutated BLS

<400> SEQUENCE: 14

```
atgcatagca accaaagcct taagacatcc tttaaaatcg cattcattca ggcccgctgg      60
cacgccgaca tcgttgacga agcgcgcaaa agctttgtcg ccgaactggc cgcaaagacg      120
ggtggcagcg tcgaggtaga gatattcgac gtgccgggtg catatgaaat tccccttcac      180
gccaagacat tggccagaac cgggcgctat gcagccatcg tcggtgcggc cttcgtgatc      240
gacggcggca tctatcgtca tgatttcgtg gcgacggccg ttatcaacgg catgatgcag      300
gtgcagcttg aaacggaagt gccggtgctg agcgtcgtgc tgacgccgca ccatttccat      360
gaaagcaagg agcatcacga cttcttccat gctcatttca aggtgaaggg cgtggaagcg      420
gcccatgccg ccttgcagat cgtgagcgag cgcagccgca tcgcgcttgt ctga           474
```

<210> SEQ ID NO 15
<211> LENGTH: 471
<212> TYPE: DNA
<213> ORGANISM: Artificial Sequence
<220> FEATURE:
<223> OTHER INFORMATION: synthetic mutated BLS

<400> SEQUENCE: 15

```
atgcatagca accaacttaa gacatccttt aaaatcgcat tcattcaggc ccgctggcac      60
gccgacatcg ttgacgaagc gcgcaaaagc tttgtcgccg aactggccgc aaagacgggt      120
ggcagcgtcg aggtagagat attcgacgtg ccgggtgcat atgaaattcc ccttcacgcc      180
aagacattgg ccagaaccgg gcgctatgca gccatcgtcg gtgcggcctt cgtgatcgac      240
ggcggcatct atcgtcatga tttcgtggcg acggccgtta tcaacggcat gatgcaggtg      300
cagcttgaaa cggaagtgcc ggtgctgagc gtcgtgctga cgccgcacca tttccatgaa      360
agcaaggagc atcacgactt cttccatgct catttcaagg tgaagggcgt ggaagcggcc      420
catgccgcct tgcagatcgt gagcgagcgc agccgcatcg cgcttgtctg a              471
```

<210> SEQ ID NO 16
<211> LENGTH: 468
<212> TYPE: DNA
<213> ORGANISM: Artificial Sequence
<220> FEATURE:
<223> OTHER INFORMATION: synthetic mutated BLS

<400> SEQUENCE: 16

```
atgcatagca accttaagac atcctttaaa atcgcattca ttcaggcccg ctggcacgcc      60
gacatcgttg acgaagcgcg caaaagcttt gtcgccgaac tggccgcaaa gacgggtggc      120
agcgtcgagg tagagatatt cgacgtgccg ggtgcatatg aaattcccct tcacgccaag      180
acattggcca gaaccgggcg ctatgcagcc atcgtcggtg cggccttcgt gatcgacggc      240
```

```
ggcatctatc gtcatgattt cgtggcgacg gccgttatca acggcatgat gcaggtgcag    300
cttgaaacgg aagtgccggt gctgagcgtc gtgctgacgc cgcaccattt ccatgaaagc    360
aaggagcatc acgacttctt ccatgctcat ttcaaggtga agggcgtgga agcggcccat    420
gccgccttgc agatcgtgag cgagcgcagc cgcatcgcgc ttgtctga               468

<210> SEQ ID NO 17
<211> LENGTH: 465
<212> TYPE: DNA
<213> ORGANISM: Artificial Sequence
<220> FEATURE:
<223> OTHER INFORMATION: synthetic mutated BLS

<400> SEQUENCE: 17
atgcatagcc ttaagacatc ctttaaaatc gcattcattc aggcccgctg gcacgccgac     60
atcgttgacg aagcgcgcaa aagctttgtc gccgaactgg ccgcaaagac gggtggcagc    120
gtcgaggtag agatattcga cgtgccgggt gcatatgaaa ttccccttca cgccaagaca    180
ttggccagaa ccgggcgcta tgcagccatc gtcggtgcgg ccttcgtgat cgacggcggc    240
atctatcgtc atgatttcgt ggcgacggcc gttatcaacg gcatgatgca ggtgcagctt    300
gaaacggaag tgccggtgct gagcgtcgtg ctgacgccgc accatttcca tgaaagcaag    360
gagcatcacg acttcttcca tgctcatttc aaggtgaagg gcgtggaagc ggcccatgcc    420
gccttgcaga tcgtgagcga gcgcagccgc atcgcgcttg tctga                   465

<210> SEQ ID NO 18
<211> LENGTH: 462
<212> TYPE: DNA
<213> ORGANISM: Artificial Sequence
<220> FEATURE:
<223> OTHER INFORMATION: synthetic mutated BLS

<400> SEQUENCE: 18
atgcatctta agacatcctt taaatcgca ttcattcagg cccgctggca cgccgacatc      60
gttgacgaag cgcgcaaaag ctttgtcgcc gaactggccg caaagacggg tggcagcgtc    120
gaggtagaga tattcgacgt gccgggtgca tatgaaattc ccttcacgc caagacattg    180 gccagaaccg ggcgctatgc agccatcgtc ggtgcggcct tcgtgatcga cggcggcatc    240
tatcgtcatg atttcgtggc gacggccgtt atcaacggca tgatgcaggt gcagcttgaa    300
acggaagtgc cggtgctgag cgtcgtgctg acgccgcacc atttccatga agcaaggag    360 catcacgact tcttccatgc tcatttcaag gtgaagggcg tggaagcggc ccatgccgcc    420
ttgcagatcg tgagcgagcg cagccgcatc gcgcttgtct ga                     462

<210> SEQ ID NO 19
<211> LENGTH: 603
<212> TYPE: DNA
<213> ORGANISM: Artificial Sequence
<220> FEATURE:
<223> OTHER INFORMATION: synthetic lumazine synthase

<400> SEQUENCE: 19
atgcatctgg aaatccgtgc ggcgttcctg cgtcagcgta acaccgcgct gcgtaccgaa     60
gttgcggaac tggaacagga agttcagcgt ctggaaaacg aagtttctca gtacgaaacc    120
cgttacggtc cgctgggtgg tggttctctt aagacatcct ttaaaatcgc attcattcag    180
gcccgctggc acgccgacat cgttgacgaa gcgcgcaaaa gctttgtcgc cgaactggcc    240
gcaaagacgg gtggcagcgt cgaggtagag atattcgacg tgccgggtgc atatgaaatt    300
```

-continued

```
cccccttcacg ccaagacatt ggccagaacc gggcgctatg cagccatcgt cggtgcggcc    360
ttcgtgatcg acggcggcat ctatcgtcat gatttcgtgg cgacggccgt tatcaacggc    420
atgatgcagg tgcagcttga aacggaagtg ccggtgctga cgtcgtgct gacgccgcac     480 catttccatg aaagcaagga gcatcacgac ttcttccatg ctcatttcaa ggtgaagggc    540
gtggaagcgg cccatgccgc cttgcagatc gtgagcgagc gcagccgcat cgcgcttgtc    600
tga                                                                  603
```

<210> SEQ ID NO 20
<211> LENGTH: 543
<212> TYPE: DNA
<213> ORGANISM: Artificial Sequence
<220> FEATURE:
<223> OTHER INFORMATION: synthetic BLS-OMP31 chimera

<400> SEQUENCE: 20

```
atgcataacg ccggttacgc aggcggcaag ttcaagcatc attttctag ctttgacaag      60 gaagacaacg aacaggtttc cggttcgctt aagacatcct ttaaaatcgc attcattcag    120
gcccgctggc acgccgacat cgttgacgaa gcgcgcaaaa gctttgtcgc cgaactggcc    180
gcaaagacgg gtggcagcgt cgaggtagag atattcgacg tgccgggtgc atatgaaatt    240 cccccttcacg ccaagacatt ggccagaacc gggcgctatg cagccatcgt cggtgcggcc   300
ttcgtgatcg acggcggcat ctatcgtcat gatttcgtgg cgacggccgt tatcaacggc    360
atgatgcagg tgcagcttga aacggaagtg ccggtgctga cgtcgtgct gacgccgcac     420 catttccatg aaagcaagga gcatcacgac ttcttccatg ctcatttcaa ggtgaagggc    480
gtggaagcgg cccatgccgc cttgcagatc gtgagcgagc gcagccgcat cgcgcttgtc    540
tga                                                                  543
```

<210> SEQ ID NO 21
<211> LENGTH: 504
<212> TYPE: DNA
<213> ORGANISM: Artificial Sequence
<220> FEATURE:
<223> OTHER INFORMATION: synthetic BLS-KETc1 chimera

<400> SEQUENCE: 21

```
atgcatgccc cgatgagcac gccgagcgcc acgagcgtcc gcggtagcct taagacatcc     60
tttaaaatcg cattcattca ggcccgctgg cacgccgaca tcgttgacga agcgcgcaaa    120
agctttgtcg ccgaactggc cgcaaagacg ggtggcagcg tcgaggtaga gatattcgac    180
gtgccgggtg catatgaaat tccccttcac gccaagacat tggccagaac cgggcgctat    240
gcagccatcg tcggtgcggc cttcgtgatc gacggcggca tctatcgtca tgatttcgtg    300
gcgacggccg ttatcaacgg catgatgcag gtgcagcttg aaacggaagt gccggtgctg    360
agcgtcgtgc tgacgccgca ccatttccat gaaagcaagg agcatcacga cttcttccat    420
gctcatttca aggtgaaggg cgtggaagcg gcccatgccg ccttgcagat cgtgagcgag    480
cgcagccgca tcgcgcttgt ctga                                           504
```

<210> SEQ ID NO 22
<211> LENGTH: 687
<212> TYPE: DNA
<213> ORGANISM: Artificial Sequence
<220> FEATURE:
<223> OTHER INFORMATION: synthetic BLS-RBD3 chimera

<400> SEQUENCE: 22

```
atgcatgaaa acctcaataa atcggaaata agccaagtgt ttgaaattgc gctgaagcgg      60
aatttgcctg tgaattttga ggtggcccgg gagagtggcc caccacacat gaagaacttt     120
gtgaccaggg tttcagttgg ggaatttgta ggggaaggag aagggaaaag caagaagatc     180
tccaagaaga atgcggccag ggctgttctg gagcagctta ggaggctgcc acttaagaca     240
tcctttaaaa tcgcattcat tcaggcccgc tggcacgccg acatcgttga cgaagcgcgc     300
aaaagctttg tcgccgaact ggccgcaaag acgggtggca gcgtcgaggt agagatattc     360
gacgtgccgg gtgcatatga aattccccct cacgccaaga cattggccag aaccgggcgc     420
tatgcagcca tcgtcggtgc ggccttcgtg atcgacggcg catctatcg tcatgatttc      480 gtggcgacgg ccgttatcaa cggcatgatg caggtgcagc ttgaaacgga agtgccggtg     540
ctgagcgtcg tgctgacgcc gcaccatttc catgaaagca aggagcatca cgacttcttc     600
catgctcatt tcaaggtgaa gggcgtggaa gcggcccatg ccgccttgca gatcgtgagc     660
gagcgcagcc gcatcgcgct tgtctga                                         687
```

<210> SEQ ID NO 23  
<211> LENGTH: 6166  
<212> TYPE: DNA  
<213> ORGANISM: Artificial Sequence  
<220> FEATURE:  
<223> OTHER INFORMATION: synthetic pBLS-OMP31 plasmid
<400> SEQUENCE: 23

```
ttcttgaaga cgaaagggcc tcgtgatacg cctatttta taggttaatg tcatgataat       60 aatggttttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240 tcccttttttt gcggcattttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt ttttctgcg    1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
```

```
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560 gggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggccttt tacggttcct    1860 ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccggagct gcatgtgtca gaggttttca ccgtcatcac     2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460 tgtaagggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga aagaatcat    3360 aatggggaag gccatccagc ctcgcgtcgc gaacgccagc aagacgtagc ccagcgcgtc   3420
ggccgccatg ccgcgataa tggcctgctt ctcgccgaaa cgtttggtgg cgggaccagt    3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccga aaggagctga ctgggttgaa ggctctcaag gcatcggtc gagatcccgg    3720 tgcctaatga gtgagctaac ttacattaat tgcgttgcgc tcactgcccg ctttccagtc   3780
```

```
gggaaacctg tcgtgccagc tgcattaatg aatcggccaa cgcgcgggga gaggcggttt    3840
gcgtattggg cgccagggtg gttttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatgcgc    4080 gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat cgatggtgt    4920 ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg    5100 aagtggcgag cccgatcttc cccatcggtg atgtcggcga tataggcgcc agcaaccgca    5160
cctgtggcgc cggtgatgcc ggccacgatg cgtccgcgct agaggatcga gatctcgatc    5220
ccgcgaaatt aatacgactc actatagggg aattgtgagc ggataacaat tcccctctag    5280
aaataatttt gtttaacttt aagaaggaga tatacatatg cataacgccg gttacgcagg    5340
cggcaagttc aagcatccat tttctagctt tgacaaggaa gacaacgaac aggtttccgg    5400
ttcgcttaag acatccttta aaatcgcatt cattcaggcc cgctggcacg ccgacatcgt    5460
tgacgaagcg cgcaaaagct tgtcgccga actggccgca aagacgggtg gcagcgtcga    5520
ggtagagata ttcgacgtgc cgggtgcata tgaaattccc cttcacgcca agacattggc    5580
cagaaccggg cgctatgcag ccatcgtcgg tgcggccttc gtgatcgacg gcggcatcta    5640
tcgtcatgat ttcgtggcga cggccgttat caacggcatg atgcaggtgc agcttgaaac    5700
ggaagtgccg gtgctgagcg tcgtgctgac gccgcaccat ttccatgaaa gcaaggagca    5760
tcacgacttc ttccatgctc atttcaaggt gaagggcgtg gaagcggccc atgccgcctt    5820
gcagatcgtg agcgagcgca gccgcatcgc gcttgtctga gctagcatga ctggtggaca    5880
gcaaatgggt cgcggatccg gctgctaaca aagcccgaaa ggaagctgag ttggctgctg    5940
ccaccgctga gcaataacta gcataacccc ttggggcctc taaacgggtc ttgaggggtt    6000
ttttgctgaa aggaggaact atatccggat atcccgcaag aggcccggca gtaccggcat    6060
aaccaagcct atgcctacag catccagggt gacggtgccg aggatgacga tgagcgcatt    6120
gttagatttc atacacggtg cctgactgcg ttagcaattt aactgt              6166
```

<210> SEQ ID NO 24
<211> LENGTH: 48
<212> TYPE: DNA
<213> ORGANISM: Artificial Sequence
<220> FEATURE:
<223> OTHER INFORMATION: synthetic BLS gene fragment

<400> SEQUENCE: 24
ggagatatac atatggctag caaccaaagc tgtccgaaca agacatcc 48

<210> SEQ ID NO 25
<211> LENGTH: 48
<212> TYPE: DNA
<213> ORGANISM: Artificial Sequence
<220> FEATURE:
<223> OTHER INFORMATION: synthetic BLS gene fragment

<400> SEQUENCE: 25
ggagatatac atatgcatag caaccaaagc tgtccgctta agacatcc 48

<210> SEQ ID NO 26
<211> LENGTH: 174
<212> TYPE: DNA
<213> ORGANISM: Artificial Sequence
<220> FEATURE:
<223> OTHER INFORMATION: synthetic oligonucleotide for BLS-OMP31 chimera production

<400> SEQUENCE: 26
taacgccggt tacgcaggcg gcaagttcaa gcatccattt tctagctttg acaaggaaga 60
caacgaacag gtttccggtt cgcacgtatt gcggccaatg cgtccgccgt tcaagttcgt 120
aggtaaaaga tcgaaactgt tccttctgtt gcttgtccaa aggccaagcg aatt 174

<210> SEQ ID NO 27
<211> LENGTH: 27
<212> TYPE: PRT
<213> ORGANISM: Artificial Sequence
<220> FEATURE:
<223> OTHER INFORMATION: synthetic fragment of BLS-OMP31 chimera

<400> SEQUENCE: 27

Asn Ala Gly Tyr Ala Gly Gly Lys Phe Lys His Pro Phe Ser Ser Phe
1 5 10 15

Asp Lys Glu Asp Asn Glu Gln Val Ser Gly Ser
20 25

<210> SEQ ID NO 28
<211> LENGTH: 96
<212> TYPE: DNA
<213> ORGANISM: Artificial Sequence
<220> FEATURE:
<223> OTHER INFORMATION: synthetic oligonucleotide for BLS-KETc1 chimera generation

<400> SEQUENCE: 28
tgccccgatg agcacgccga gcgccacgag cgtccgcggt agccacgtac ggggctactc 60
gtgcggctcg cggtgctcgc aggcgccatc ggaatt 96

<210> SEQ ID NO 29
<211> LENGTH: 6127
<212> TYPE: DNA
<213> ORGANISM: Artificial Sequence
<220> FEATURE:
<223> OTHER INFORMATION: synthetic pET11a vector with cloned BLS-KETc1

<400> SEQUENCE: 29

```
ttcttgaaga cgaaagggcc tcgtgatacg cctattttta taggttaatg tcatgataat      60
aatggtttct tagacgtcag gtggcacttt tcggggaaat gtgcgcggaa ccccctatttg    120
tttattttc taaatacatt caaatatgta tccgctcatg agacaataac cctgataaat     180
gcttcaataa tattgaaaaa ggaagagtat gagtattcaa catttccgtg tcgcccttat     240
tcccttttt gcggcatttt gccttcctgt ttttgctcac ccagaaacgc tggtgaaagt      300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga acgatcgg aggaccgaag gagctaaccg cttttttgca      660
caacatgggg gatcatgtaa ctcgccttga tcgttggga ccggagctga atgaagccat      720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttgata atctcatgac caaaatccct taacgtgagt tttcgttcca    1200
ctgagcgtca gacccgtag aaaagatcaa aggatcttct tgagatcctt ttttctgcg     1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatgaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
```

```
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca gacccaacg ctgcccgaga   2940 tgcgccgcgt gcggctgctg agatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg ccccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga agaatcat   3360 aatgggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg cgacgatag tcatgccccg   3660 cgcccaccgg aaggagctga ctgggttgaa ggctctcaag ggcatcggtc gagatcccgg   3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg ttttttcttt tcaccagtga gacgggcaac agctgattgc   3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
gcgccgagac agaacttaat gggcccgcta acagcgcgat ttgctggtga cccaatgcga   4320
ccagatgctc cacgcccagt cgcgtaccgt cttcatggga gaaataata ctgttgatgg   4380 gtgtctggtc agagacatca agaaataacg ccggaacatt agtgcaggca gcttccacag   4440
caatggcatc ctggtcatcc agcggatagt taatgatcag cccactgacg cgttgcgcga   4500
gaagattgtg caccgccgct ttacaggctt cgacgccgct tcgttctacc atcgacacca   4560
ccacgctggc acccagttga tcggcgcgag atttaatcgc cgcgacaatt tgcgacggcg   4620
cgtgcagggc cagactggag gtggcaacgc caatcagcaa cgactgtttg cccgccagtt   4680
gttgtgccac gcggttggga atgtaattca gctccgccat cgccgcttcc acttttttccc   4740
```

```
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg      5100 aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tatacatatg catgccccga tgagcacgcc    5340
gagcgccacg agcgtccgcg gtagccttaa gacatccttt aaaatcgcat tcattcaggc    5400
ccgctggcac gccgacatcg ttgacgaagc gcgcaaaagc tttgtcgccg aactggccgc    5460
aaagacgggt ggcagcgtcg aggtagagat attcgacgtg ccgggtgcat atgaaattcc    5520
ccttcacgcc aagacattgg ccagaaccgg gcgctatgca gccatcgtcg gtgcggcctt    5580
cgtgatcgac ggcggcatct atcgtcatga tttcgtggcg acggccgtta tcaacggcat    5640
gatgcaggtg cagcttgaaa cggaagtgcc ggtgctgagc gtcgtgctga cgccgcacca    5700
tttccatgaa agcaaggagc atcacgactt cttccatgct catttcaagg tgaagggcgt    5760
ggaagcggcc catgccgcct tgcagatcgt gagcgagcgc agccgcatcg cgcttgtctg    5820
agctagcatg actggtggac agcaaatggg tcgcggatcc ggctgctaac aaagcccgaa    5880
aggaagctga gttggctgct gccaccgctg agcaataact agcataaccc cttggggcct    5940
ctaaacgggt cttgaggggt tttttgctga aggaggaac tatatccgga tatccgcaa     6000 gaggcccggc agtaccggca taaccaagcc tatgcctaca gcatccaggg tgacggtgcc    6060
gaggatgacg atgagcgcat tgttagattt catacacggt gcctgactgc gttagcaatt    6120
taactgt                                                              6127
```

<210> SEQ ID NO 30
<211> LENGTH: 6361
<212> TYPE: DNA
<213> ORGANISM: Artificial Sequence
<220> FEATURE:
<223> OTHER INFORMATION: synthetic BLS-RBD3-expressing vector

<400> SEQUENCE: 30

```
ttcttgaaga cgaaagggcc tcgtgatacg cctatttta taggttaatg tcatgataat     60
aatggtttct tagacgtcag gtggcacttt tcggggaaat gtgcgcggaa cccctatttg    120 tttattttc taaatacatt caaatatgta tccgctcatg agacaataac cctgataaat    180
gcttcaataa tattgaaaaa ggaagagtat gagtattcaa catttccgtg tcgcccttat    240 tcccttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540 tacgatggc atgacagtaa gagaattatg cagtgctgcc ataaccatga gtgataacac    600
tgcggccaac ttacttctga caacgatcgg aggaccgaag gagctaaccg cttttttgca    660
```

```
caacatgggg gatcatgtaa ctcgccttga tcgttgggaa ccggagctga atgaagccat    720
accaaacgac gagcgtgaca ccacgatgcc tgcagcaatg caacaacgt tgcgcaaact     780 attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttttgata atctcatgac caaaatccct taacgtgagt tttcgttcca   1200
ctgagcgtca gaccccgtag aaaagatcaa aggatcttct tgagatcctt ttttctgcg     1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacataccct gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct cccgaaggg agaaaggcgg acaggtatcc     1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtatttc tccttacgca    2040 tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca gacccaacg ctgcccgaga    2940 tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
```

```
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat     3360 aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacgggcc tgccaccata cccacgccga acaagcgct catgagcccg      5100 aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tatacatatg catgaaaacc tcaataaatc    5340
ggaaataagc caagtgtttg aaattgcgct gaagcggaat ttgcctgtga attttgaggt    5400
ggcccgggag agtggcccac cacacatgaa gaactttgtg accagggttt cagttgggga    5460
```

```
atttgtaggg gaaggagaag ggaaaagcaa aagaagatctcc aagaagaatg cggccagggc   5520
tgttctggag cagcttagga ggctgccact taagacatcc tttaaaatcg cattcattca   5580
ggcccgctgg cacgccgaca tcgttgacga agcgcgcaaa agctttgtcg ccgaactggc   5640
cgcaaagacg ggtggcagcg tcgaggtaga gatattcgac gtgccgggtg catatgaaat   5700
tccccttcac gccaagacat tggccagaac cgggcgctat gcagccatcg tcggtgcggc   5760
cttcgtgatc gacggcggca tctatcgtca tgatttcgtg gcgacggccg ttatcaacgg   5820
catgatgcag gtgcagcttg aaacggaagt gccggtgctg agcgtcgtgc tgacgccgca   5880
ccatttccat gaaagcaagg agcatcacga cttcttccat gctcatttca aggtgaaggg   5940
cgtggaagcg gccatgccg ccttgcagat cgtgagcgag cgcagccgca tcgcgcttgt   6000
ctgagctagc atgactggtg gacagcaaat gggtcgcgga tccggctgct aacaaagccc   6060
gaaaggaagc tgagttggct gctgccaccg ctgagcaata actagcataa ccccttgggg   6120
cctctaaacg ggtcttgagg ggttttttgc tgaaaggagg aactatatcc ggatatcccg   6180
caagaggccc ggcagtaccg gcataaccaa gcctatgcct acagcatcca gggtgacggt   6240
gccgaggatg acgatgagcg cattgttaga tttcatacac ggtgcctgac tgcgttagca   6300
atttaactgt gataaactac cgcattaaag cttatcgatg ataagctgtc aaacatgaga   6360
a                                                                   6361

<210> SEQ ID NO 31
<211> LENGTH: 6277
<212> TYPE: DNA
<213> ORGANISM: Artificial Sequence
<220> FEATURE:
<223> OTHER INFORMATION: synthetic pET11a with BLS gene inserted

<400> SEQUENCE: 31
ttcttgaaga cgaaagggcc tcgtgatacg cctatttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
```

```
ggtgaagatc cttttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga agaatcat    3360 aatggggaag ccatccagcc tcgcgtcgc gaacgccagc aagacgtagc ccagcgcgtc   3420
ggccgccatg ccgcgataa tggcctgctt ctcgccgaaa cgtttggtgg cgggaccagt   3480
gacgaaggct tgagcgaggg cgtgcaagat tccgaatacc gcaagcgaca ggccgatcat   3540
```

```
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga cgggcaac agctgattgc       3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggg acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740
gcgttttcgc agaaacgtgg ctggcctggt tcaccacgcg ggaaacggtc tgataagaga    4800
caccggcata ctctgcgaca tcgtataacg ttactggttt cacattcacc ccctgaatt     4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg      5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actataggggg aattgtgagc ggataacaat tcccctctag   5280
aaataatttt gtttaacttt aagaaggaga tatacatatg catctggaaa tccgtgcggc    5340
gttcctgcgt cagcgtaaca ccgcgctgcg taccgaagtt gcggaactgg aacaggaagt    5400
tcagcgtctg gaaaacgaag tttctcagta cgaaacccgt tacggtccgc tgggtggtgg    5460
ttctcttaag acatccttta aaatcgcatt cattcaggcc cgctggcacg ccgacatcgt    5520
tgacgaagcg cgcaaaagct tgtcgccga actggccgca aagacgggtg gcagcgtcga    5580
ggtagagata ttcgacgtgc cgggtgcata tgaaattccc cttcacgcca agacattggc    5640
cagaaccggg cgctatgcag ccatcgtcgg tgcggccttc gtgatcgacg gcggcatcta    5700
tcgtcatgat ttcgtggcga cggccgttat caacggcatg atgcaggtgc agcttgaaac    5760
ggaagtgccg gtgctgagcg tcgtgctgac gccgcaccat ttccatgaaa gcaaggagca    5820
tcacgacttc ttccatgctc atttcaaggt gaagggcgtg gaagcggccc atgccgcctt    5880
gcagatcgtg agcgagcgca ccgcatcgc gcttgtctga gctagcatga ctggtggaca     5940
```

```
gcaaatgggt cgcggatccg gctgctaaca aagcccgaaa ggaagctgag ttggctgctg    6000
ccaccgctga gcaataacta gcataacccc ttggggcctc taaacgggtc ttgaggggtt    6060
ttttgctgaa aggaggaact atatccggat atcccgcaag aggcccggca gtaccggcat    6120
aaccaagcct atgcctacag catccagggt gacggtgccg aggatgacga tgagcgcatt    6180
gttagatttc atacacggtg cctgactgcg ttagcaattt aactgtgata aactaccgca    6240
ttaaagctta tcgatgataa gctgtcaaac atgagaa                             6277

<210> SEQ ID NO 32
<211> LENGTH: 5117
<212> TYPE: DNA
<213> ORGANISM: Artificial Sequence
<220> FEATURE:
<223> OTHER INFORMATION: synthetic pGEX-4T1 with BLS gene inserted

<400> SEQUENCE: 32
acgttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag ggccttgtgc     300
aacccactcg acttcttttg gaatatcttg aagaaaaata tgaagagcat ttgtatgagc     360
gcgatgaagg tgataaatgg cgaaacaaaa gtttgaattg ggtttggag tttcccaatc     420 ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caaagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg gttccgcgtg gatccctgga aatcgaagcg gcgttcctgg     960
aacgtgaaaa caccgcgctg gaaacccgtt tgcggaact gcgtcagcgt gttcagcgtc    1020
tgcgtaaccg tgtttctcag taccgtaccc gttacggtcc gctgggtggt ggtaaatgat    1080
tctcctgaat tcccgggtcg actcgagcgg ccgcatcgtg actgactgac gatctgcctc    1140
gcgcgtttcg gtgatgacgg tgaaaacctc tgacacatgc agctcccgga gacggtcaca    1200
gcttgtctgt aagcggatgc cgggagcaga caagcccgtc agggcgcgtc agcgggtgtt    1260
ggcgggtgtc ggggcgcagc catgacccag tcacgtagcg atagcggagt gtataattct    1320
tgaagacgaa agggcctcgt gatacgccta tttttatagg ttaatgtcat gataataatg    1380
gtttcttaga cgtcaggtgg cacttttcgg ggaaatgtgc gcggaacccc tatttgttta    1440
tttttctaaa tacattcaaa tatgtatccg ctcatgagac aataaccctg ataaatgctt    1500
caataatatt gaaaaaggaa gagtatgagt attcaacatt tccgtgtcgc ccttattccc    1560
ttttttgcgg cattttgcct tcctgttttt gctcacccag aaacgctggt gaaagtaaaa    1620
gatgctgaag atcagttggg tgcacgagtg ggttacatcg aactggatct caacagcggt    1680
aagatccttg agagttttcg ccccgaagaa cgttttccaa tgatgagcac ttttaaagtt    1740
```

```
ctgctatgtg gcgcggtatt atcccgtgtt gacgccgggc aagagcaact cggtcgccgc    1800
atacactatt ctcagaatga cttggttgag tactcaccag tcacagaaaa gcatcttacg    1860
gatggcatga cagtaagaga attatgcagt gctgccataa ccatgagtga taacactgcg    1920
gccaacttac ttctgacaac gatcggagga ccgaaggagc taaccgcttt tttgcacaac    1980
atggggatc atgtaactcg ccttgatcgt tgggaaccgg agctgaatga agccatacca    2040
aacgacgagc gtgacaccac gatgcctgca gcaatggcaa caacgttgcg caaactatta    2100
actggcgaac tacttactct agcttcccgg caacaattaa tagactggat ggaggcggat    2160
aaagttgcag gaccacttct gcgctcggcc cttccggctg gctggtttat tgctgataaa    2220
tctggagccg gtgagcgtgg gtctcgcggt atcattgcag cactgggcc agatggtaag    2280
ccctcccgta tcgtagttat ctacacgacg gggagtcagg caactatgga tgaacgaaat    2340
agacagatcg ctgagatagg tgcctcactg attaagcatt ggtaactgtc agaccaagtt    2400
tactcatata ctttagat tgatttaaaa cttcattttt aatttaaaag gatctaggtg    2460
aagatccttt ttgataatct catgaccaaa atcccttaac gtgagttttc gttccactga    2520
gcgtcagacc ccgtagaaaa gatcaaagga tcttcttgag atcctttttt tctgcgcgta    2580
atctgctgct tgcaaacaaa aaaaccaccg ctaccagcgg tggtttgttt gccggatcaa    2640
gagctaccaa ctctttttcc gaaggtaact ggcttcagca gagcgcagat accaaatact    2700
gtccttctag tgtagccgta gttaggccac cacttcaaga actctgtagc accgcctaca    2760
tacctcgctc tgctaatcct gttaccagtg gctgctgcca gtggcgataa gtcgtgtctt    2820
accgggttgg actcaagacg atagttaccg gataaggcgc agcggtcggg ctgaacgggg    2880
ggttcgtgca cacagcccag cttggagcga acgacctaca ccgaactgag atacctacag    2940
cgtgagctat gagaaagcgc cacgcttccc gaagggagaa aggcggacag gtatccggta    3000
agcggcaggg tcgaacagg agagcgcacg agggagcttc caggggggaaa cgcctggtat    3060
ctttatagtc ctgtcgggtt tcgccacctc tgacttgagc gtcgatttt gtgatgctcg    3120
tcagggggc ggagcctatg gaaaaacgcc agcaacgcgg cctttttacg gttcctggcc    3180
ttttgctggc cttttgctca catgttcttt cctgcgttat cccctgattc tgtggataac    3240
cgtattaccg cctttgagtg agctgatacc gctcgccgca gccgaacgac cgagcgcagc    3300
gagtcagtga gcgaggaagc ggaagagcgc ctgatgcggt attttctcct tacgcatctg    3360
tgcggtattt cacaccgcat aaattccgac accatcgaat ggtgcaaaac ctttcgcggt    3420
atggcatgat agcgcccgga agagagtcaa ttcagggtgg tgaatgtgaa accagtaacg    3480
ttatacgatg tcgcagagta tgccggtgtc tcttatcaga ccgtttcccg cgtggtgaac    3540
caggccagcc acgtttctgc gaaaacgcgg gaaaagtgg aagcggcgat ggcggagctg    3600
aattacattc ccaaccgcgt ggcacaacaa ctggcgggca aacagtcgtt gctgattggc    3660
gttgccacct ccagtctggc cctgcacgcg ccgtcgcaaa ttgtcgcggc gattaaatct    3720
cgcgccgatc aactgggtgc cagcgtggtg gtgtcgatgg tagaacgaag cggcgtcgaa    3780
gcctgtaaag cggcggtgca caatcttctc gcgcaacgcg tcagtgggct gatcattaac    3840
tatccgctgg atgaccagga tgccattgct gtggaagctg cctgcactaa tgttccggcg    3900
ttatttcttg atgtctctga ccagacaccc atcaacagta ttattttctc ccatgaagac    3960
ggtacgcgac tgggcgtgga gcatctggtc gcattgggtc accagcaaat cgcgctgtta    4020
gcgggcccat taagttctgt ctcggcgcgt ctgcgtctgg ctggctggca taaatatctc    4080
actcgcaatc aaattcagcc gatagcggaa cgggaaggcg actggagtgc catgtccggt    4140
```

```
tttcaacaaa ccatgcaaat gctgaatgag ggcatcgttc ccactgcgat gctggttgcc      4200
aacgatcaga tggcgctggg cgcaatgcgc gccattaccg agtccgggct gcgcgttggt      4260
gcggatatct cggtagtggg atacgacgat accgaagaca gctcatgtta tatcccgccg      4320
ttaaccacca tcaaacagga ttttcgcctg ctggggcaaa ccagcgtgga ccgcttgctg      4380
caactctctc agggccaggc ggtgaagggc aatcagctgt tgcccgtctc actggtgaaa      4440
agaaaaacca ccctggcgcc caatacgcaa accgcctctc cccgcgcgtt ggccgattca      4500
ttaatgcagc tggcacgaca ggtttcccga ctggaaagcg ggcagtgagc gcaacgcaat      4560
taatgtgagt tagctcactc attaggcacc ccaggcttta cactttatgc ttccggctcg      4620
tatgttgtgt ggaattgtga gcggataaca atttcacaca ggaaacagct atgaccatga      4680
ttacggattc actggccgtc gttttacaac gtcgtgactg ggaaaaccct ggcgttaccc      4740
aacttaatcg ccttgcagca catccccctt cgccagctg gcgtaatagc gaagaggccc       4800
gcaccgatcg cccttcccaa cagttgcgca gcctgaatgg cgaatggcgc tttgcctggt      4860
ttccggcacc agaagcggtg ccggaaagct ggctggagtg cgatcttcct gaggccgata      4920
ctgtcgtcgt cccctcaaac tggcagatgc acggttacga tgcgcccatc tacaccaacg      4980
taacctatcc cattacggtc aatccgccgt ttgttcccac ggagaatccg acgggttgtt      5040
actcgctcac atttaatgtt gatgaaagct ggctacagga aggccagacg cgaattattt      5100
ttgatggcgt tggaatt                                                    5117

<210> SEQ ID NO 33
<211> LENGTH: 822
<212> TYPE: DNA
<213> ORGANISM: Artificial Sequence
<220> FEATURE:
<223> OTHER INFORMATION: nucleotide sequence of synthetic BLS gene

<400> SEQUENCE: 33 atgtcccta tactaggtta ttggaaaatt aagggccttg tgcaacccac tcgacttctt        60
ttggaatatc ttgaagaaaa atatgaagag catttgtatg agcgcgatga aggtgataaa       120
tggcgaaaca aaaagtttga attgggtttg gagtttccca atcttcctta ttatattgat       180
ggtgatgtta aattaacaca gtctatggcc atcatacgtt atatagctga caagcacaac       240
atgttgggtg ttgtccaaa agagcgtgca gagatttcaa tgcttgaagg agcggttttg       300
gatattagat acggtgtttc gagaattgca tatagtaaag actttgaaac tctcaaagtt       360
gattttctta gcaagctacc tgaaatgctg aaaatgttcg aagatcgttt atgtcataaa       420
acatatttaa atggtgatca tgtaacccat cctgacttca tgttgtatga cgctcttgat       480
gttgttttat acatggaccc aatgtgcctg gatgcgttcc caaaattagt ttgttttaaa       540
aaacgtattg aagctatccc acaaattgat aagtacttga atccagcaa gtatatagca       600 tggcctttgc agggctggca agccacgttt ggtggtggcg accatcctcc aaaatcggat       660
ctggttccgc gtggatccct ggaaatcgaa gcggcgttcc tggaacgtga aacaccgcg       720 ctggaaaccc gtgttgcgga actgcgtcag cgtgttcagc gtctgcgtaa ccgtgtttct       780
cagtaccgta cccgttacgg tccgctgggt ggtggtaaat ga                         822

<210> SEQ ID NO 34
<211> LENGTH: 273
<212> TYPE: PRT
<213> ORGANISM: Artificial Sequence
```

-continued

<220> FEATURE:
<223> OTHER INFORMATION: amino acid sequence of synthetic BLS protein

<400> SEQUENCE: 34

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Leu Glu Ile Glu Ala Ala Phe Leu Glu Arg Glu Asn Thr Ala
225                 230                 235                 240

Leu Glu Thr Arg Val Ala Glu Leu Arg Gln Arg Val Gln Arg Leu Arg
                245                 250                 255

Asn Arg Val Ser Gln Tyr Arg Thr Arg Tyr Gly Pro Leu Gly Gly Gly
            260                 265                 270

Lys

<210> SEQ ID NO 35
<211> LENGTH: 35
<212> TYPE: DNA
<213> ORGANISM: Artificial Sequence
<220> FEATURE:
<223> OTHER INFORMATION: synthetic oligonucleotide primer for amplifying
      BLS-OMP31

<400> SEQUENCE: 35
taagaagaat ccaccaccat gcataccgcc ggtta                             35

<210> SEQ ID NO 36
<211> LENGTH: 37
<212> TYPE: DNA
<213> ORGANISM: Artificial Sequence
<220> FEATURE:
<223> OTHER INFORMATION: synthetic oligonucleotide primer for amplifying
      BLS-OMP31

-continued

```
<400> SEQUENCE: 36
tgtccaccag tcatgctagc tcagacaagc gcgatgc                                    37
```

ISOLATED CHIMERIC PROTEINS OF MODIFIED LUMAZINE SYNTHASE This application claims priority from PCT Application No. PCT/US2005/019289, filed Jun. 3, 2005, and from Argentine Patent Application No. P 04 01 01923, filed Jun. 3, 2004, which applications are incorporated herein by reference.

TECHNICAL DESCRIPTION OF THE INVENTION

Isolated chimeric proteins including up to ten copies of peptides, polypeptides or protein domains inserted in the amino termini of the *Brucella* spp. lumazine synthase enzyme. Isolated nucleotides sequences codifying the chimeric proteins. Vectors, plasmids and transformed cells used for expressing the proteins. Monoclonal and polyclonal antibodies produced by such chimeric proteins. Hybridomas producing monoclonal antibodies. Vaccines and pharmaceutical compounds including the chimeric proteins, nucleotide sequences and antibodies. A method to induce an immune response in higher organisms including the administration of effective amounts of the vaccines and pharmaceutical compounds. Biosensors including the chimeric proteins. Protein conjugates formed by the chimeric proteins and a ligand bound by means of covalent and noncovalent bonds. Uses of the chimeric proteins, nucleotide sequences, vectors, plasmids, transformed cells, antibodies, hybridomas, conjugates, biosensors, vaccines and pharmaceutical compounds. The quaternary structure of the chimeric proteins.

TECHNICAL FIELD OF THE INVENTION

The present invention relates to chimeric proteins formed by modified proteins derived from the lumazine synthase enzyme of *Brucella* spp., linked to peptides, polypeptides or proteins domains. The chimeric proteins are useful for inducing immune responses in higher animals and for other purposes. The present invention relates also to pharmaceutical compounds including antigens or antibodies, or segments of antigens or antibodies, bound to the modified proteins.

BACKGROUND OF THE INVENTION

The massive application of live-attenuated vaccines offer several economic and health inconveniences. When live vaccines are attenuated their immunogenic capability is often reduced. See Leclerc, et al., *Immunol. Today,* 19(7):300-302, (1998); Nieba, et al., *Mod. Asp. Immunobiol.,* 1(2):36-39 (2000). Another inconvenience is the possibility that the attenuation be reverted and that the microorganism regain its disease inducing properties. See Redfield, N., *N. Eng. J. Med.,* 316:673-678 (1998). Hence, during the past years, the trend has been to formulate acellular vaccines, based on individual compounds isolated from bacteria or virus. In general, these individual compounds, like proteins typical of a microorganism, have low immunogenicity. This limitation has been overcome by using adjuvant substances. However, there are proteins that even in the presence of adjuvant substances continue showing low immunogenicity. Several protein engineering strategies have been proposed to overcome these difficulties. See Leclerc, et al., *Immunol. Today,* 19(7):300-302 (1998).

Viral capsid proteins are able to form tridimensionally ordered particles, called "virus-like particles". These particles have the same size and shape as whole viruses. However, they are empty inside and without genetic material rendering then incapable of producing infections. Their great size and order provide them with a marked immunogenicity. See Bachmann, et al., *Science,* 262:1448-1451 (1993). The recombinant vaccine against hepatitis B, widely accepted in the market, is based on this concept. The "virus-like particles" have been used as a vehicle for inserting peptides characteristic of certain pathogens with the aim of producing vaccines against such pathogenic microorganisms. See WO0032227 (Renner, et al.); WO0185208 (Bachmann, et al.). A favored strategy has been the insertion of multiple copies of a peptide in a very immunogenic vehicle, in order to provide a peptide with the adjuvant property of the carrier. However, this approach has encountered many difficulties: owing to the huge size of these particles, any insertion of a peptide in its compounding protein obstructs its proper folding and, in many cases, decreases its stability. Moreover, there are few sites able to accept peptide insertions without changing their general structure. See Nieba, et al. *Mod. Asp. Immunobiol,* 1(2):36-39 (2000).

Some bacterial proteins have been postulated as vehicles for developing chimeric vaccines. See Leclerc, et al., *Immunol. Today,* 19(7):300-302 (1998). The subunit B of the cholera toxin is a stable pentameric protein that has been used to obtain an immune response from the mucosa against inserted peptides. This strategy has been successful due to this toxin capacity to penetrate the gastric mucosa. See Arakawa, et al. *Nature Biotech.,* 16:934-938 (1998). The dihydrolipoyl dehydrogenase enzyme of the *Bacillus steearothermophilus* has also been postulated as a proteic vehicle because it forms a complex and very stable polymeric structure. See Domingo, et al., *J. Mol. Biol.,* 305:259-267 (2001); WO0142439 (Domingo, et al.).

The lumazine synthase enzyme catalyzes the penultimate step in the riboflavin biosynthetic route. See Goldbaum, et al., *J. Med. Microbiol.,* 48:833-839 (1999). Its active site is located in the interphase among monomers, making this protein to have a very stable polymeric order. See Ritsert, et al. *J. Mol. Biol.,* 253:151-167 (1995). These orders vary between proteins forming pentameric and icosahedric particles. See Braden, et al., *J. Mol. Biol.,* 297:1031-1036 (2000). The icosahedric structure of the lumazine synthase of *B. subtilis* has been postulated as a vehicle for inserting peptides and developing vaccines. See WO0053229 (Bacher, et al.).

The lumazine synthase of *Brucella* spp. is a highly stable protein. It has been demonstrated that this 18-kDa protein is a useful marker for the serological diagnosis of human and animal brucellosis. See Goldbaum, et al., *J. Clin. Microbiol.,* 30:604-607 (1992); Goldbaum, et al., *J. Clin. Microbiol.,* 31:2141-2145 (1993); Baldi, et al., *Clin. Diag. Lab. Immunol.,* 3 (4):472-476 (1996). According to immunochemical enzymatic function and tridimensional structure by X-ray crystallography analyses the original and modified protein shows the same when expressed recombinantly as the native protein. See Braden, et al. *J. Mol. Biol.,* 297:1031-1036 (2000); Goldbaum, et al., *J. Med. Microbiol.,* 48:833-839 (1999); Goldbaum, et al., *J. Struct. Biol.,* 123:175-178 (1998). The structure shows that this 18-kDa protein behaves as a 180-kDa decamer in solution, becoming a new type of quaternary arrangement of the lumazine synthase. See Zylberman, et al., *J. Biol. Chem.,* 279(9):8093-8101 (2004).

It has been postulated that the immunogenicity of the lumazine synthase of *Brucella* spp. derives mainly from its polymeric character. See Baldi, et al., *Braz. J. Med. Biol. Res.,* 33:741-747 (2000). The structure also shows that the amino termini end of 10 aminoacids is involved neither in the general folding nor in the contacts among monomers. See Braden, et al. *J. Mol. Biol.,* 297:1031-1036 (2000). The lumazine synthase of *Brucella* spp. is a powerful immunogen capable of producing a high humoral and cellular immune response in the murine model. This capability has been verified when the immunization is induced with the recombinant and modified protein and with a plasmid that codifies for the protein (gene therapy, DNA vaccination). See Velikovsky, et al., *J. Immunol. Meth.,* 244(1-2):1-7 (2000). It is possible to modulate the response by changing the immunization route and the adjuvant used. See Velikovsky, et al., *Infec. Immun.,* 70(5):2507-11 (2002). Particularly, it is possible to create a strong response of the $T_H1$ type, which would be the response with the highest protecting capacity in brucellosis. See Velikovsky, et al. *Infec. Immun.,* 70(5):2507-11 (2002).

However, it is still a need in the art for new vehicles with smaller stable structures useful for displaying peptides, polypeptides and proteins, in general, and antigens or immune response-inducing agents, in particular. The development and use of the lumazine synthase decameric structure as a vector of this type have not been described in the art.

Deposit of Microorganisms

The pBLS-OMP31 plasmid was deposited on Apr. 1, 2004, under access number DSM 15546 in DSMZ—Deutsche Sammlung von Mikroorganismen und Zellkulturen, Mascheroder Weg 1B, D-38124 Braunschweig, Germany.

DIAGRAMS

FIG. 1 shows the nucleotide and amino acid sequence of the 5' end of the gene of the cloned BLS gene in the expression vector pET11a (Novagen, USA) and the generated cassette (SEQ ID NOs: 24 and 25). The section in bold case shows the codifying region. The section in red case shows the mutated bases in the cassette. Section highlighted in yellow shows the new restriction sites.

FIG. 2 shows the oligonucleotides used to generate the BLS-OMP31 chimera (SEQ ID NO: 26). Their annealing produces the appearance of cohesive sites corresponding to the NsiI (5' end) and AflII (3' end) restriction enzymes, the sequence of 27 aminoacids inserted in the chimera (below, in bold case) being located among them (SEQ ID NO: 27). The theoretical molecular weight of the resulting protein monomer (19,977.5 Daltons) and the theoretical isoelectric point (pI=6.00) of the inserted peptide are also shown.

FIG. 3 shows: a) the pET11a plasmid scheme including the BLS-OMP31 chimera sequence, showing the restriction sites used when cloning, b) the complete nucleotide sequence of the pET11a plasmid including the BLS-OMP31 chimera and c) the open reading frame of the BLS-OMP31 chimera, and its amino acid sequence.

FIG. 4 describes the expression of BLS-OMP31 analyzed by SDS-PAGE in 17% acrylamide. MW. Molecular Weight Markers in KiloDaltons, 1: purified BLS, 2 and 3: aliquots of expression cultures of two BLS-OMP31 clones. The protein migrates like a 20-KDa monomer because the gel is denaturalizing.

FIG. 5 describes the expression of BLS-OMP31 analyzed by SDS-PAGE in 17% acrylamide. 1: culture without induction, 2: culture induced with 1 mM IPTG, 3: cytoplasmatic fraction, 4: fraction of inclusion bodies resuspended in 8M urea. The arrows show the bands corresponding to a BLS-OMP31. (LMWM=low molecular weight markers, weight indicated in kilodaltons).

FIG. 6 shows the chromatogram corresponding to the elution of the BLS-OMP31 in the Superdex 200 (Pharmacia, USA) column. The peaks were analyzed afterwards by gel and are numbered. See FIG. 7.

FIG. 7 shows the purification data of BLS-OMP31 analyzed by SDS-PAGE in 17% acrylamide. 1 and 2: peaks obtained by gradient of BLS-OPM31 elution of the Q-Sepharose (Pharmacia, USA) column. 4 and 5: the numbering of the peaks correlates to the peaks in FIG. 6. (LMWM=low molecular weight markers, weight indicated in kilodaltons).

FIG. 8 shows the circular dichroism spectra of BLS and the BLS-OMP31 chimera. The molar elipticity of a 1.0-μM solution of protein between 190 and 260 nm was monitored in a spectropolarimeter (Jasco, UK).

FIG. 9 describes a comparative analysis of the stability of the BLS-OMP31 chimera in relation to the native protein. The curves show the sensitivity to unfolding in the presence of growing concentrations of the denaturalizing guanidine hydrochloride chemical agent, evaluated by the elipticity developed by the protein in a spectropolarimeter at 222 nm.

FIG. 10 shows the antigenicity of BLS-OMP32 by ELISA. 1 ug, 0.25 ug, 0.1 ug and 20 ng of BLS-OMP31 and BLS were used as antigens. Anti-BLS Mab (1/1000) and Anti-OMP31 Mab (1/1000) were used as antibodies.

FIG. 11 shows the immunogenicity of BLS-OMP31 analyzed by ELISA. The reactivity of 1/100 dilutions of sera from mice immunized with BLS-OMP31 with adjuvant (“AF”) or without adjuvant (“PBS”) against OMP31 are shown. Sera of each group were ordered per decreasing reactivity. The reactivity of a pre-immune serum (negative control) is illustrated by a dot line. A mouse from the AF group died before the extraction.

FIG. 12 shows the titration results of an ELISA test of sera from anti BLS-OMP31 rabbit. The reactivity of the three sera against OMP31 was assayed. A 1/100 dilution of a serum of anti BLS-WT rabbit was used as a negative serum. The reactivity of this serum is illustrated by a dot line.

FIG. 13 describes the reactivity of an anti BLS-OMP31 rabbit serum (4° dose) against smooth or rough *B. melitensis* H38 whole bacteria. The reactivity corresponding to a rabbit anti native BLS serum, tittered simultaneously against both antigens, was substracted from the values shown. The errors correspond to the sum of mean standard errors.

FIG. 14 shows the kinetics of total anti-OMP31 IgG antibodies in mice batches BALB/c (8 per group) immunized in 4 occasions by intramuscular and intradermal route with 100 μg of pCI-BLS-OMP31. Antibodies levels were analyzed by ELISA every 15 days. The values represent the mean value of the 8 animals ±S.D. The arrows show the time of the immunization. Sera of pCI mice (control) showed n DO values similar to or lower than the “cut-off” criteria.

FIG. 15 describes: a) the oligonucleotide sequence used to obtain the BLS-KETc1 chimera (SEQ ID NO: 28), b) the complete nucleotide sequences of the pET11a plasmid including the BLS-KETc1 chimera and c) the open reading frame of the BLS-KETc1 chimera and its amino acid sequence.

FIG. 16 shows the general strategic scheme to produce mixed chimeras.

FIG. 17 shows the purification results and analysis of mixed chimeras created between the BLS-OMP31 and BLS-KETc1 chimeras. A: analysis by anionic interchange chromatography in MonoQ column of BLS-OMP31 (peak 3) and BLS-KETc1 (peak 1) refolded chimeras and the stoichiometric mixture of both (peak 2), B1: analysis through SDS-PAGE of peaks 1, 2 and 3 obtained in the anionic interchange chromatography, B2: Analysis through native PAGE of pure BLS-OMP31 and BLS-KETc1 chimeras and of peak 2 corresponding to the mixed chimeras.

Figure 18:
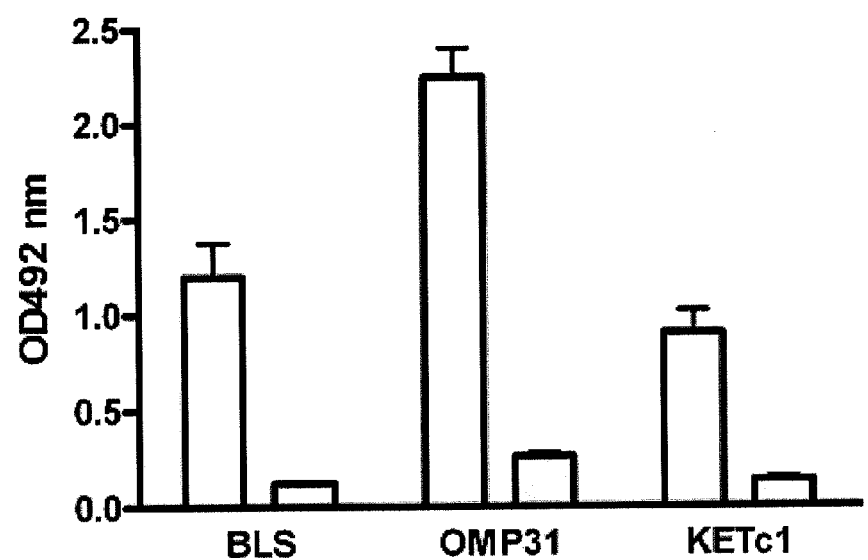

FIG. 18 shows the immunogenicity of the BLS-OMP31-KETc1 mixed chimera analyzed by ELISA. Reactivity of 1/100 dilutions of sera from mice immunized with BLS-OMP31-KETc1 (empty bars) against BLS and against OMP31 and KETc1 synthetic peptides. The reactivity of a pre-immune serum (negative control) against the same antigens is indicated in gray bars.

FIG. 19 shows the in vitro proliferation of splenocytes induced by the immunization with BLS-KETc1. It indicates the average plus 1 standard deviation of the titrated (in cpm) timidine incorporation after the in vitro stimulations of splenocytes from mice previously immunized with KETc1 peptide or BLS-KETc1 emulsified in saponin. *Significant increase in cpm in respect of splenocytes incubated with a culture medium ($P<0.05$).

FIG. 20A and FIG. 20B describe the nucleotide and aminoacid sequence of the BLS-RBD3 chimera. The codifying sequence of domain RBD3 of the murine protein Staufen-1 is shown in red case. The codifying sequence of the truncated BLS in the first 8 residues of its amino termini is shown in black case.

Figure 21A:
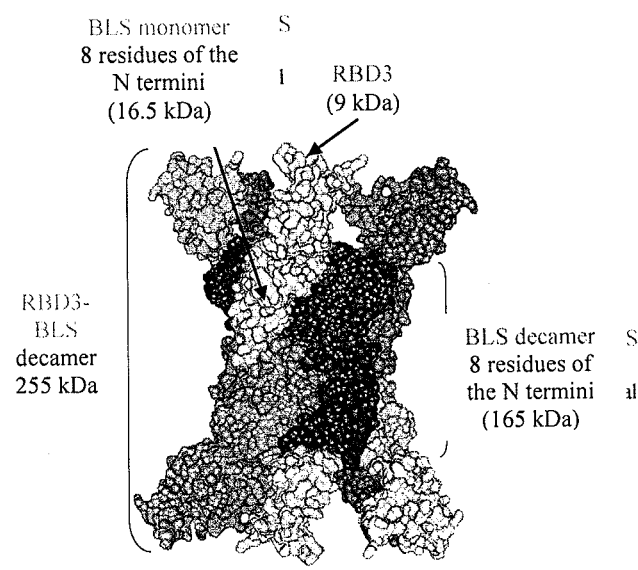
Figure 21B:
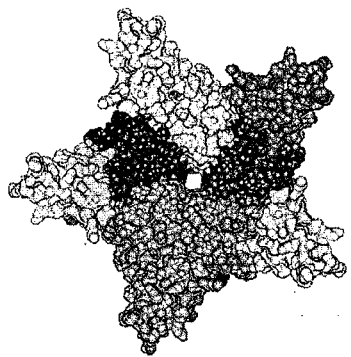
Figure 22A:
Figure 22B:
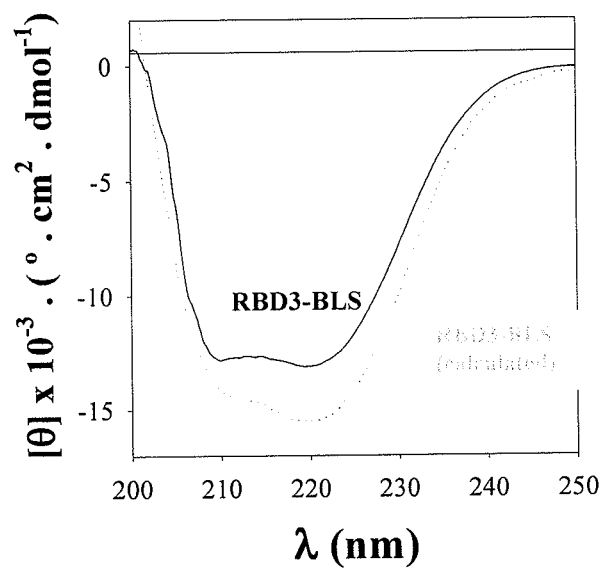
Figure 22C:
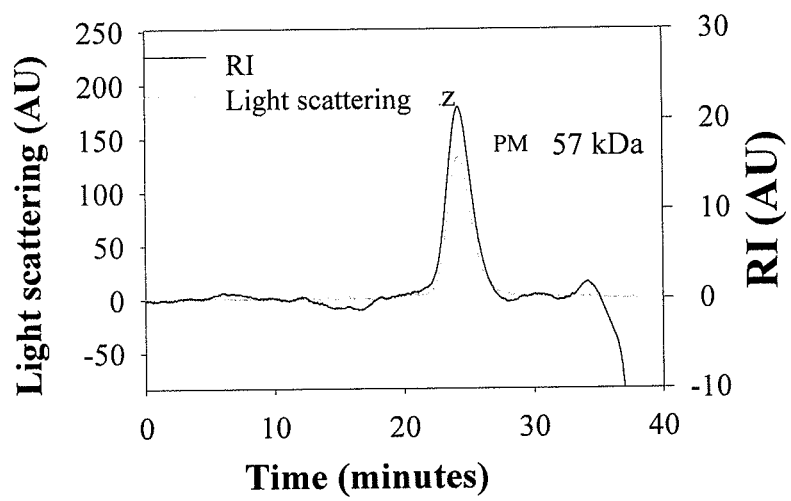

FIG. 21 shows the structure of the BLS-RBD3 chimera (panel A: side view, panel B: upper view). The structure was designed with the MacroModel program merging the C-terminal end with the theoretical structure of the domain RBD3 of the murine protein Staufen-1 (shown in a blue range of colors) with the N-terminal end of the BLS crystallographic structure (Protein DataBank file pdb: 1DIO) (shown in a red range of colors). The theoretical structure of domain RBD3 of the murine protein Staufen-1 was built by means of homology modeling with the structure of the domain RBD3 of the protein Staufen of *Drosophila melaganoster* (pdb: 1EKZ). The figure was built with the CHIMERA program.

FIG. 22 shows: A: the separation of the BLS-RBD3 chimera by SDS-PAGE in a 15% polyacrilamid gel (P/V), various molecular weight markers were run in the right pathway. B: the circular dichroism spectrum in the UV far from the BLS-RBD3 chimera. The figure comparatively shows the chimera spectrum measured experimentally (in a continuous line) and its theoretical spectrum (in a dot line), calculated from the combination of the spectra corresponding to BLS protein and RBD3 domain of the murine protein Staufen-1 in isolation. The measurement was performed in a 50 mM Tris/HCl, 1.2 M NaCl, pH 8 buffer, at 4° C. C: the assessment of molecular weight of the BLS-RBD3 chimera by using a light scattering detector connected in series to the outlet of a molecular filtering column and an refraction index (RI) detector. BLS-RBD3 was run in a Superdex-200 column and eluted with a 50 mM Tris/HCl, 3 M urea, 1 M NaCl, pH 8 buffer, at a flow of 0.5 ml/min. The elution was monitored by measuring its light scattering signal at 90 degrees and light refraction (LR). The sample molecular weight was calculated by comparing the relationship of its light scattering and refraction signals with those of a bovine seroalbumin sample used as a reference pattern (BSA molecular weight: 66.5 kDa).

FIG. 23 shows the optical density obtained at 492 nm of the 1/100 dilution of sera analyzed for each mice of each investigational group. The result at 30-day interval after the second immunization is shown as a representative example. The horizontal line represents the mean value of each group.

FIG. 24 shows the results of an anti-OMP31 Mab ELISA test.

FIG. 25 shows the detection of anti-OMP31, AcMo37F7 monoclonal antibody, using a biosensor formed by derivatization with the BLS-OMP31 chimeric protein.

FIG. 26 shows the expression of costimulating molecules in dendritic cells stimulated with BLS. Dendritic cells, derived from the bone marrow, were incubated during 18 hs with BSL (BLS 10 μM) or with medium only (control). The expression of CD40 in $CD11c^+$ cells (A) and of $I\text{-}A^d$ in $CD11c^+$ (B) is shown. The isotype controls are shown to the left of each graph.

FIG. 27 shows the strategy followed to form molecular assemblies with complementary heterodimeric peptides incorporated into the modified BLS protein and a theoretical X antigen target. See Braden, et al., supra. A Swisspdbviewer modeling software was used.

FIG. 28A and FIG. 28B show the nucleotide sequence of the BLS-$RR_{12}EE_{345}L$ insert gene cloned in the expression vector pET11a (Novagen, USA) (SEQ ID NO: 31). The section in red case shows the codifying region of the BLS-$RR_{12}EE_{345}L$ insert peptide. The section in black case shows the codifying region for the modified BLS protein.

FIG. 29 describes the nucleotide and amino acid sequences of the BLS-$RR_{12}EE_{345}L$ fusion protein (SEQ ID NOs: 19 and 8, respectively). The section in red case shows the codifying region of the $RR_{12}EE_{345}L$ peptide. The section in black case shows the codifying region for the modified BLS protein. The section in green case shows the position of $K_{49}$ residue substituted with serine.

FIG. 30 shows the separation of the BLS-$RR_{12}EE_{345}L$ fusion protein by SDS-PAGE in a 17% polyacrylamide gel. 1: molecular weight markers, 2: irrelevant sample, 3: fusion protein BLS-$RR_{12}EE_{345}L$.

FIG. 31 shows the assessment of molecular weight of the BLS-$RR_{12}EE_{345}L$ chimera by using a light scattering detector serially connected to the outlet of a molecular filtering column and a refraction index (RI) detector. BLS-$RR_{12}EE_{345}L$ was run in a Superdex-200 column and eluted with a 50 mM Tris/HCl, 3 M urea, 0.1 M NaCl, pH 8 buffer, at a flow of 0.5 ml/min. The elution was monitored by measuring its light scattering signal at 90 degrees and light refraction (LR). The sample molecular weight was calculated by comparing the relationship of its light scattering and refraction signals with those of a bovine seroalbumin sample used as a reference pattern (BSA molecular weight: 66.5 kDa).

FIG. 32 shows the nucleotide sequence of the peptide $EE_{12}RR_{345}L$ insert gene cloned in the expression vector pGEX-4T1 (Novagen, USA) (SEQ ID NO: 32). The sequence is inserted between the BamH1 y EcoR1 restriction sites of the vector. The section in black case shows the codifying region for GST protein. The section in red case shows the codifying region for the peptide $EE_{12}RR_{345}L$.

FIG. 33 shows the nucleotide sequence of the peptide GST-$EE_{12}RR_{345}L$ insert gene cloned in the expression vector pGEX-4T1 (Novagen, USA) and the corresponding amino acid sequence (SEQ ID NOs: 33 and 34, respectively).

FIG. 34 shows the molecular assembly between fusion protein BLS-$RR_{12}EE_{345}L$ and peptide $EE_{12}RR_{345}L$.

FIG. 35 shows 10 $EE_{12}RR_{345}L$ peptides coupled to the BLS-$RR_{12}EE_{345}L$ decamer.

DESCRIPTION OF THE INVENTION

The present invention describes chimeric proteins useful, in general, for displaying peptides, polypeptides and proteins. The peptides, polypeptides and proteins shown herein may induce an immune response or be suitable for other useful purposes.

The present invention also describes pharmaceutical compounds and vaccines of high immunogenic value and efficacy. These compounds and vaccines include chimeric proteins generated by using the lumazine synthase enzyme of *Brucella* spp. (BLS) as an immunogenic vehicle.

The chimeric proteins described in this application can display peptides, polypeptides, proteins or molecules of other distinctive pathogens and non-pathogens types.

More specifically, the chimeric proteins described in this application can be useful for the treatment and prevention of human diseases. These entities can be used for the inoculation of antigens, toxins and protein domains with low or without immunogenic activity. Examples of these indications would be vaccination against common measles, German measles (rubella), hepatitis, tetanus, pertussis, poliomyelitis, diphtheria, mumps, meningitis and rabies, in infants. Other examples of these indications are the vaccination against hepatitis A, B and C, influenza, encephalitis, rabies, typhoid fever, yellow fever, herpes simplex, varicella zoster, dengue, human papillomavirus, cholera, malaria, tuberculosis and mumps in adults. Other examples of these indications are vaccines useful to counteract bioterrorism, for the following pathogens: *Botulinum toxin, Bacillus anthracis, Clostridium perfringens, Bacillus subtilus, Bacillus thuringiensis,* hemorrhagic conjunctivitis virus (Enterovirus 70) and rotavirus.

These entities can also be used for the treatment of chronic conditions, such as Alzheimer's disease, Parkinson's disease and rheumatoid arthritis or other conditions, such as allergies and tumors. An example of the latter could consist of a chimeric protein simultaneously including antibodies or fragment of antibodies against tumoral markers or radioactive elements for radiotherapy. The chimeric proteins developed according to the present invention, and the antibodies derived from them, could also be used for the diagnosis of fertility and pregnancy, or of diseases such as colon, lung, breast and prostate cancer. These entities could also be used to monitor and control drug abuse or the progress for therapeutic treatments.

The chimeric proteins described in the present invention also have multiple uses for the breeding domestic animals, farm animals and fish. These entities may be used to prepare vaccines against *Brucella* spp., a bacterial agent that causes many problems in cattle, or against *Piscirickettsia salmonis*, which mainly affects the commercial breeding of salmon. Moreover, these entities can be useful to administer antibacterial agents, such as penicillin, amoxicillin or other penicillin subproducts, alone or in combination with specific antibodies to domesticated animals, like cats and dogs, or farming animals, like cattle.

Other possible uses of the chimeric proteins described in this application are the preparation of vaccines against *Mycoplasma hyopneumoniae*, a pneumonic agent that produces great losses in pigs, and administration of parasiticides, like albendazole, fenbendazole and ivermectin against *Ostertagia ostertagi*, to calves and cattle in general. It would also be possible to use these new entities to administer parasiticides, like abamectine and praziquantel, to horses and to vaccination with epitopes of antigens or viral protein domains, like poultry influenza, to birds. In all cases, the chimeric protein can simultaneously contain the parasiticide agent and the specific antibodies against the involved parasite. An additional therapeutical use of the new entities would be the administration of antiinflammatory agents, like carprofen to domesticated animals, like dogs and cats.

The chimeric proteins according to the present invention could also have different indications for the control of pathogens. These entities could be used to modify the expression of certain hormones to accelerate the growth rate and increase the production of milk, in farming animals or make their meat leaner. An example of these non-conventional indications would be the use of these entities for immunocastration of farming animals, like pigs.

The chimeric proteins described in this application can also be used for the large-scale production of vaccines and antibodies in molecular farming. Under this approach, the vaccine or antibody will be expressed firstly in a suitable plant. The vaccine or antibody will then be extracted and purified to prepare a pharmaceutical formulation. Another possibility would be to feed animals with plants so transformed with the entities described herein to immunize via their food intake (edible vaccines).

A particular advantage of the present invention is that the vehicles described herein are able to carry peptides larger than other vehicles known in the art, such as the "virus like particles". This advantage is due to their small size and higher stability. This antigenic display system of the vehicles described herein has the additional advantage of displaying peptides, polypeptides and proteins inserted repeatedly and ordered spatially, increasing their stability and half-life. The carrier protein (BLS) also has a considerable adjuvant effect on peptides, polypeptides and proteins inserted thus enhancing the immune response effectiveness.

Another advantage of the present invention is that the carrier protein BLS induces an immune response by itself without the presence of additional adjuvants. This characteristic facilitates the administration of vaccines prepared according to the present invention by various routes of administration (e.g., intravenous, nasal, oral, needle-free) with or without adjuvants.

The pharmaceutical compounds and vaccines described in this application are characterized by their high stability at room temperature. This characteristic would likely preserve the compound or vaccine without keeping a strict cold chain of storage.

The creation of mixed chimeras with multiple peptides inserted in the different ends of the carrier protein BLS is also useful to design multivalent vaccines or vaccines aimed at different routes of immune response. The prevailing opinion in the art at present is that a vaccine should not contain more than 10 immune response-inducing agents. It is also the prevailing opinion in the art that the vaccine should contain 5 or less inducing agents to achieve optimal results.

The chimeric proteins described in this application are useful for the production of antibodies. These antibodies and their associated entities could be used in diagnosis. It is also possible to develop kits for the diagnosis of diseases using the above-mentioned antibodies and associated entities.

Several of these entities developed according to the present invention could be also used to display peptides and build protein libraries and their associated applications (e.g., combinational biology applied to the identification of molecules for the development of drugs or the identification of polypeptide sequences binding preferably inorganic compounds, for nanobiological applications). Some of these new entities could also be used for the production and assembly of nanotechnologic devices or for the conduction of nanotechnologic processes.

The chimeric proteins according to the present invention could be used in the construction and development of biosensors applied to the analytical detection of several substances and molecules (e.g., detection of contaminants or toxins in water, soil or air, detection of residues of drugs, herbicides and pesticides in food).

Another advantage of the entities described in this present application is its easy and low-cost production. The chimeric proteins described in this application are obtained in high amounts from a model of transformed strains from *E. coli*, a microorganism of well-known management and culture. The proteins of interest obtained according to this method are easily purified from the culture medium.

In a version of this present invention, the isolated chimeric proteins claimed herein are formed by a peptide, polypeptide or protein linked to a protein mutated from the lumazine synthase of *Brucella* spp. whose codifying nucleotide sequence has been modified in its first 8 residues as its N-termini to allow its cleavage by restriction enzymes that do not cleave naturally the codifying nucleotide sequence of the native lumazine synthase protein of *Brucella* spp. Preferably, the codifying nucleotide sequence of the mutated lumazine synthase of *Brucella* spp. protein has been modified for the first 8 residues at its N-termini in order to allow its cleavage with the Nsi I and Afl II restriction enzymes. More preferably the mutated lumazine synthase proteins used according to the present invention have the amino acid sequences SEQ ID NO:1, SEQ ID NO:2, SEQ ID NO:3, SEQ ID NO:4, SEQ ID NO:5, SEQ ID NO:6, SEQ ID NO:7. The linked peptide, polypeptide or protein can be homologous or heterologous. In a version of the present invention, the peptide linked to the mutated protein is a heterodimerization domain. Preferably, this heterodimerization domain is a "leucine zipper" domain. The chimeric proteins thus obtained include, but are not limited to, the amino acid sequence SEQ ID NO:8 and are used preferably for the coupling of protein domains, complete proteins or other non-protein entities. In another version of this invention, the combinations of isolated chimeric proteins described in this present application are also claimed. The uses of these isolated chimeric proteins and of their combinations are also claimed.

In another embodiment of the present invention, the isolated codifying nucleotide sequences for the chimeric proteins described in this application are claimed. These sequences can be of RNA, genomic DNA or copy DNA. In another embodiment of the present invention, the codifying sequence for the linked peptide, polypeptide or protein is located in the 5' region of the codifying nucleotide sequence for the mutated lumazine synthase protein of *Brucella* spp. In another embodiment of the present invention, the codifying sequence for the linked peptide, polypeptide or protein is operatively linked to the 5' region of the codifying nucleotide sequence for the mutated lumazine synthase protein of *Brucella* spp. Preferably the following DNA sequences utilized are: SEQ ID NO:12, SEQ ID NO:13, SEQ ID NO:14, SEQ ID NO:15, SEQ ID NO:16, SEQ ID NO:17, SEQ ID NO:18 and SEQ ID NO:19. Specific instances of the mutated protein sequences used in the present invention include, but are not limited to, the framework nucleotide sequences: a) BLS-OMP31 b) BLS-KETc1 and c) BLS-RBD3, used in Examples 1, 5 and 8, respectively. In another embodiment of this invention, the combinations of isolated nucleotide sequences described in this present application are claimed. The uses of these isolated nucleotide sequences and their combinations are also claimed.

In another embodiment of the present invention, the combinations of isolated chimeric proteins and the isolated nucleotide sequences described in the present invention are claimed.

In another embodiment of the present invention, the vectors including the codifying sequences for the chimeric proteins described herein are claimed. These vectors can be bacterial, viral or other origin, and are able to express, or facilitate the expression of the chimeric proteins described in the present application. Specific instances of these vectors are pBLS-OMP31, pBLS-KETc1 and pBLS-RBD3 plasmids, used in Examples 1, 5 and 8, respectively. Preferably, the pBLS-OMP31, DSM 15546 plasmid is used as a vector and as a precursor for the generation of plasmids expressing the chimeric proteins described in the present application. The uses of these vectors are also claimed.

In another embodiment of the present invention, the cells or microorganisms transformed with the vectors described in this application are claimed. These microorganisms could be of prokaryote, eukaryote or other origin. Specific instances of the cells that can be transformed with the vectors described in the present invention include, but are not limited to, insect cells, bacteria, such as *Escherichia coli*, and mammal cells, such as CHO, COS, BHK, Namalwa and HeLa. More preferably, competent strains of *Escherichia coli* are used for such transformations. The uses of these cells are also claimed.

In a version of present invention, the isolated chimeric proteins described herein are able to induce an immune response in a eukaryote organism. These chimeric proteins can induce cellular or humoral responses in the treated organism. In these cases, the response could be against the same antigen, toxin, protein domain or inducing agent or against different antigens, toxins, protein domains or inducing agents. The antigens, toxins, protein domains or agents used according to the present invention could be of bacterial, parasitic, viral or other origin, and be able to induce an immune response. Specific instances of these inducing agents include, but are not limited to the: a) the 27 amino acid sequence of the OMP31 protein of *Brucella mellitus*, b) the 14 amino acid sequence of the KETc1 protein of *Tenia solium* and c) the 75 amino acid sequence of the RBD3 domain of murine protein Staufen, used in Examples 1, 5 and 8, respectively. In general, the treated eukaryote organisms are birds, fish or mammals. Preferably, these organisms are from a murine, rabbit or human origin. More preferably, the organism is of human origin. The uses of these chimeric proteins able to induce an immune response are also claimed.

In a version of present invention, the codifying nucleotide sequences for the isolated chimeric proteins described herein are able to induce an immune response in an eukaryote organism. These nucleotide sequences can induce cellular or humoral responses in the treated organism. In these cases, the response can be against the same antigen, toxin, protein domain or inducing agent or against different antigens, toxins, protein domains or inducing agents. The antigens, toxins, protein domains or inducing gents used according to the present invention can be of bacterial, parasitic, viral or other origin, and are able to induce an immune response. Specific instances of these inducing agents include, but are not limited to, the codifying nucleotide sequences for: a) the 27 amino acids of the OMP31 protein of *Brucella melitensis*, b) the 14 amino acids of the KETc1 protein of *Tenia solium* and c) the 75 amino acids of the RBD3 domain of murine protein Staufen, used in Examples 1, 5 and 8, respectively. In general, the treated eukaryotic organisms are birds, fish or mammals. Preferably, these organisms are from a murine, rabbit or human origin. More preferably, the organism is of human origin. The uses of these nucleotide sequences able to induce an immune response are also claimed.

In a version of the present invention, pharmaceutical compound or vaccines including the following are claimed: 1) at least one type of the chimeric proteins described in this application, 2) at least one type of the codifying nucleotide sequences for the chimeric proteins described in this application or 3) a combination of 1 and 2).

The pharmaceutical formulations or vaccines claimed for in the present application can be in a liquid state or in any other pharmaceutical form known in the art, such as injectable emulsions. The pharmaceutical compounds or vaccines described in the present invention can also be in tablets, liquid solutions, suspensions or elixirs for oral administration or in sterile liquids such as solutions or suspensions. Preferably an inert medium is used, such as saline media, phosphate-saline buffers and any other medium where the chimeric proteins, nucleotide sequences or segments thereof have a proper solubility.

The active agents of the pharmaceutical compounds or vaccines claimed in this invention are present in effective physiological doses. These active agents can be administered alone or in combination with acceptable pharmaceutical excipients, such as adjuvants, in order to increase the production of antibodies.

The pharmaceutical compounds or vaccines according to the present invention include, but are not limited to, several oily formulations such the Freund adjuvant, tyrosin stearate, MDP dipeptide, saponin, aluminum hydroxide (alum), lymph cytokines, the native protein of the lumazine synthase of *Brucella* spp. and proteins mutated from the lumazine synthase of *Brucella* spp. described herein. See U.S. Pat. No. 4,258,029 (Moloney, et al.); U.S. Pat. No. 5,057,540 (Kensil, et al.). Preferably tyrosin stearate, aluminum hydroxide, the native protein of the lumazine synthase of *Brucella* spp. and the mutated proteins described herein are used in the case of human beings. The Freund adjuvant, though powerful, is not used usually in human beings. The pharmaceutical compound or vaccine can also be administered using slow releasing mechanisms, such as liposomes. See U.S. Pat. No. 4,235,877 (Fullerton, W.). The preparation of vaccines and pharmaceutical compounds for their use in higher organisms is known in the art. See Remington, et al., *Pharmaceutical Sciences*, Mack Publishing Co., Easton, Pa., 1980; Voller, et al., Eds., *New Trends and Developments in Vaccines*, University Park Press, Baltimore, Md., 1978.

In a version of the present invention, a method to induce an immune response in a eukaryotic organism is claimed. The method encompasses the administration to such organism of an effective amount of a pharmaceutical compound or vaccines including: 1) at least one type of the chimeric proteins described in this application, 2) at least one type of the codifying nucleotide sequences for the chimeric proteins described in this application or 3) a combination of 1 and 2). In a version of this invention, a humoral response is induced. In another embodiment of this invention, a cellular response is induced. In another embodiment of this invention, humoral or cellular responses are induced simultaneously or sequentially. In these cases, responses can be against the same antigen, toxin, protein domain or inducing agent or against different antigens, toxins, protein domains or inducing agents. The antigens, toxins, protein domains or agents used according to the present invention can be of bacterial, parasitic, viral or other origin, and are able to induce an immune response. Specific instances of these inducing agents include, but are not limited to, the nucleotide sequences codifying for or to the amino acid sequences of: a) the 27 amino acids of the OMP31 protein of *Brucella melitensis*, b) the 14 amino acids of the KETc1 protein of *Tenia solium* and c) the 75 amino acids of the RBD3 domain of murine Staufen protein, used in Examples 1, 5 and 8, respectively. Examples of organisms that may be treated with the vaccines and pharmaceutical compounds described in this application are birds, fish or mammals. Preferably, these organisms are from a murine, rabbit or human origin. More preferably, the organism is of human origin. The vaccines or pharmaceutical compounds described in the present invention can be administered in one or several doses. Preferably, the administration is performed in only one dose. The administration can also be performed by subcutaneous, intravenous, intramuscular, oral, nasal or needle-free route. Preferably, it is performed by subcutaneous or intramuscular route.

In another embodiment of the present invention, the monoclonal and polyclonal antibodies produced in response to the immunization with chimeric proteins and the nucleotide sequences described herein are claimed. The hybridomas developed for expressing and producing the antibodies described in this application are also claimed. The uses of these antibodies for their preventive, therapeutic, diagnostic and other purposes are claimed. The pharmaceutical compounds including the antibodies described herein and their uses are also claimed.

In another embodiment of the present invention, the protein conjugates formed between the chimeric proteins described herein and one ligand are claimed. In a version of this invention, the link between the chimeric protein and the ligand is covalent. In these cases, the link is preferably peptidic. In another embodiment of this invention, the link between the chimeric protein and the ligand is non-covalent. The uses of these protein conjugates are also claimed.

In another embodiment of the present invention, the typical quaternary structure of the chimeric proteins described herein is claimed.

As used herein, "active agent" is defined as: 1) genomic DNA, copy DNA, messenger RNA or segments thereof, codifying for the chimeric proteins, or fragments thereof, described in the present application and 2) the chimeric proteins, or segments thereof described in the present application, 3) the combinations of 1) and 2) or 4) the protein conjugates formed between the chimeric proteins described herein or segments thereof and other entities.

As used herein, the term "effective amount" is defined as a quantity sufficient to produce one or more of the following results: 1) induction of a proper immune response, whether humoral or cellular, including the production of antibodies against the inducing agent; 2) inhibition of the growth, development, size and motility of the cell or microorganism associated with the inducing agent. When the inducing agent is a tumor, the "effective amount" will be the quantity sufficient to reduce the size, to prevent growth, to inhibit the metastasis or tumor growth, or to relieve the discomfort caused by such tumor or to prolong the life of an individual suffering from such tumor.

As used herein, the term "mammal" is defined as a hot-blooded vertebrate animal whose descendants are fed with milk secreted by its mammal glands. The term "mammal" includes, but it is not limited to, rats, mice, rabbits, dogs, cats, goats, cows, sheep, pigs, primates and human beings.

As used herein, the term "pharmaceutical compound or vaccine" is defined as a diluent, adjuvant or excipient with which the active agent is administered jointly. It includes each and every solvent, dispersion media, aqueous and gaseous solutions, coatings, antibacterial and antifungal agents, isotonic agents, retardants or catalysts of absorption or similar substances. The use of such media and agents in the administration of active pharmaceutical substances is known in the art. The use of such conventional media with the active agent is indicated unless the active agent is rendered ineffective by the media. Supplementary active principles can also be incorporated into the active agents described in the present invention. The term "pharmaceutical compounds or vaccines" include, but are not limited to, inert solvents or excipients, sterile aqueous solutions and several non-toxic organic solvents. The "pharmaceutical compounds or vaccines" should neither react with nor otherwise reduce the efficacy or stability of the active agent. The acceptable pharmaceutical vehicles include, but are not limited to, water, ethanol, polyethileneglycol, mineral oil, petrolatum, propyleneglycol, lanolin and similar agents. The "pharmaceutical compounds or vaccines" for injectable use include sterile aqueous solutions (when soluble in water) or sterile dispersions and powders for preparing sterile injectable dispersions or solutions. In every case, the formulation should be sterile and preferably fluid in order to enable its dispensing through a syringe. It should also be stable under manufacturing and storing conditions and should be protected from the contaminating effect of microorganisms such as bacteria, virus and fungi.

As used herein, the term "preventive use" is defined the capacity to induce and generate an immune response against one or more antigens, toxins, protein domains or other inducing agents, or segments thereof.

As used herein, the term "sequential administration" means that: 1) the same active agent is administered in more than one occasion at consecutive periods of time or 2) two or more active agents are administered alternatively in more than one occasion at consecutive periods of time. When the administration is "sequential", the time difference between the administrations of active agents may be minutes, hours, days, weeks or months depending on whether the use is preventive or therapeutical and on the nature of the treated organism.

As used herein, the term "single or simultaneous administration" means that one or more active agents are administered in the same occasion at once.

As used herein, the term "therapeutic use" is defined to refer to every process, therapy or similar action, in which a higher organism, including a human being, is subject to medical care with the aim of improving such organism condition or resistance to diseases, whether directly or indirectly.

EXAMPLE 1

BLS-OMP31 Chimeric Gene Construction

This example describes the strategy used to insert the sequence corresponding to the 48 to 74 amino acids of the polypeptidic sequence of the OMP31 protein of *Brucella melitensis* into the 10 amino termini of the decamer forming the lumazine synthase of *Brucella* spp.

1. Mutation and Cloning

The pBLS-OMP31 plasmid, SEQ ID NO:23, was constructed through the following protocol:
a) To clone the codifying gene for the lumazine synthase of *Brucella* spp. (BLS), the BLS sequence was obtained by PCR amplification with specific primers from the genomic DNA of *B. abortus* and cloned in the pET11a vector (Novagen, USA). The pET11-BLS plasmid containing the open reading frame of the lumazine synthase of *Brucella* spp. was digested further with the Bam HI and XbaI restriction enzymes. The insert obtained was subcloned in the pALter-Ex1 vector (Promega, USA).
b) A directed mutagenesis was performed over the sequence codifying for the open reading frame of the lumazine synthase of *Brucella* spp. (BLS). This sequence was cloned in the pALter-Ex1 vector (Promega, USA) using the ALTERED sitesII kit (Promega, USA). In order to develop the cassette, two new restriction sites were inserted in the 5' region of the BLS gene: an Nsi site in the first two codons of the 5' end,
and one AFL II site in the two codons comprising the 8 and 9 residues of the native amino acids sequence of BLS. It was taken into consideration that these restriction sites do not occur in the native BLS gene or in the pET11a vector. See FIG. 1.
c) The mutation was checked afterwards by sequencing. The cassette including the mutated BLS sequence (SEQ ID NO:12), was subcloned in the pET11a vector (Novagen, USA), to obtain the plasmid called hereinafter pBSLm.
d) To insert the sequence corresponding to the OMP31 plasmid, two oligonucleotides were designed so that they form a double-stranded DNA and include the codifying sequence for the 48-74 aminoacids of the OMP31 protein of *Brucella melitensis* protected by the cohesive ends typical of the Nsi I and Afl II restriction enzymes when annealing. FIG. 2 shows the oligonucleotides designed for constructing the pBLS-OMP31 and the synthetic insert formed by these.
e) The pBLSm plasmid was digested with the Nsi I and Afl II restriction enzymes. The codifying sequence corresponding to the first 8 residues of the BLS was removed. The original BLS sequence was changed for the nucleotide sequence of the inserted OMP31 peptide in this case.
f) The synthetic insert of step d) above was linked to the open pBLSm cassette obtained in step e) by incubating overnight with DNA T4 ligase enzyme at 16° C. The insertion was confirmed by sequencing. Thus, a gene with the SEQ ID NO:20 sequence was obtained. The sequencing analysis showed that the first 8 aminoacids of the lumazine synthase of the *Brucella* spp. were replaced by the 27 aminoacids from the 48-74 sequence of the OMP31 protein of *Brucella melitensis*. This open reading frame was called BLS-OMP31 chimera, of SEQ ID NO:20. Its corresponding plasmid was called pBLS-OMP31, of SEQ ID NO:23. See FIGS. 3b and c.

This experiment was repeated using the DNA sequences of the mutated BLS SEQ ID NO:13, SEQ ID NO:14, SEQ ID NO:15, SEQ ID NO:16, SEQ ID NO:17 and SEQ ID NO:18. Similar results were obtained.

2. Transformation

Figure 4:
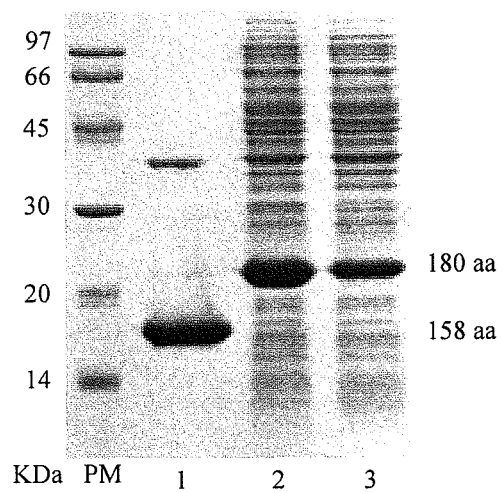

A competent strain of *E. coli* BL21 (DE3) bacteria was transformed by thermal shock with the pBLS-OMP31 plasmid obtained according to the protocol above. Afterwards, bacteria were cultured in agar plates including LB-agar/ampicilin to choose those transformed with the plasmid. 2 ml of a LB/ampicilin medium was inoculated to a colony extracted from agar plates for small-scale expression tests. The colony was shaked and incubated at 37° C. The saturated culture was induced with 2 µl of 1M.IPTG. Three hours later, 100 µl of culture was removed, centrifuged The resulting pellet was resuspended in 25 µl of sample buffer 1× for its analysis by SDS-PAGE 17%. See FIG. 4.

3. Expression and Purification of the BLS-OMP31 Chimeric Protein

A 5-ml preculture of the transformed strains was cultured to saturation according to the step above, with 500 ml of LB/ampicilin. The culture was incubated and shaked at 37° C. It was induced with 0.5 ml of IPTG (1M) to reach an optical density of 0.6-0.8 at 600 nm. The culture was removed three hours later and was centrifuged at 4000 g for 20 min. The pellet was suspended in 15 ml of suspension solution (50 mM Tris, 5 mM, EDTA, 1% Triton X-100, pH 8.0).

Figure 5:
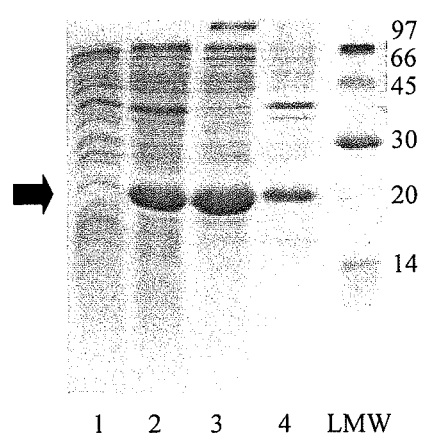

The suspension was sonicated at 1 minute intervals every minute for 5 minutes and was centrifuged at 20,000 g for 30 minutes. The pellet was resuspended in 15 ml of suspension solution without Triton X-100 and the sonicate process was repeated. The procedure was repeated for a third time. The chimera expressed in the cytoplasm was contained in three sonicate supernatants, while inclusions bodies were contained in the pellet. See FIG. 5.

The inclusion bodies were resuspended in PBS buffer with 8 M urea and were left overnight at room temperature. The resuspension was dialyzed against PBS for two days with a buffer change. The sample was centrifuged and the supernatant was dialyzed against buffer A (50 mM Tris/HCl, pH 8.5). The first purification step was performed by anionic interchange chromatography in a MonoQ or a Q-Sepharose (Pharmacia, USA) column in a FPLC equipment (Pharmacia, USA). The sample was injected in the balanced column with buffer A and was eluted by linear gradient up to 50% of buffer B (buffer A+1 M NaCl).

Figure 6:
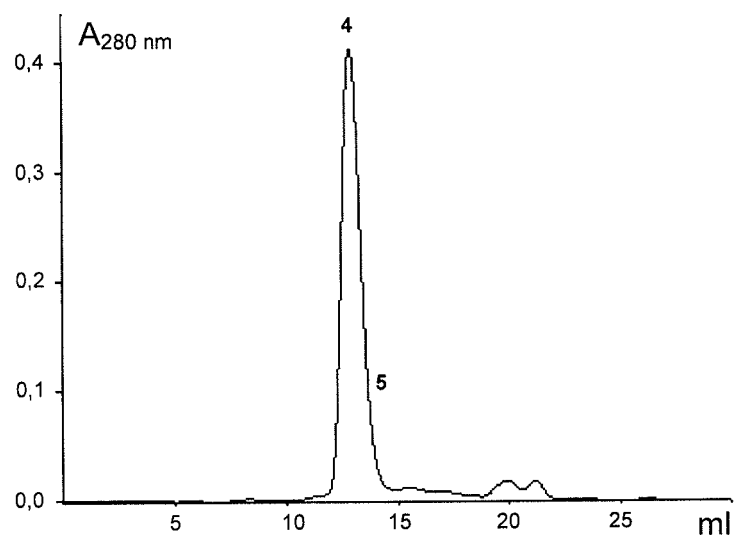
Figure 7:
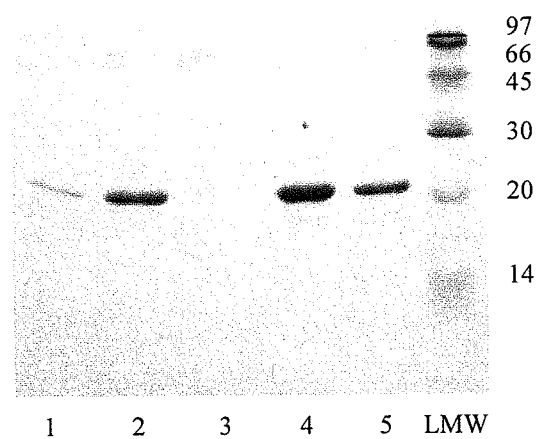
Figure 8:
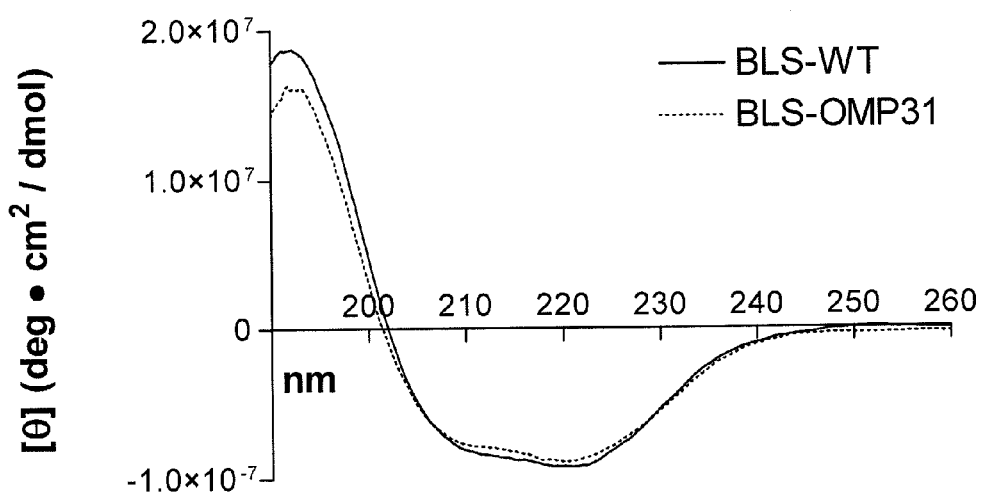
Figure 9:
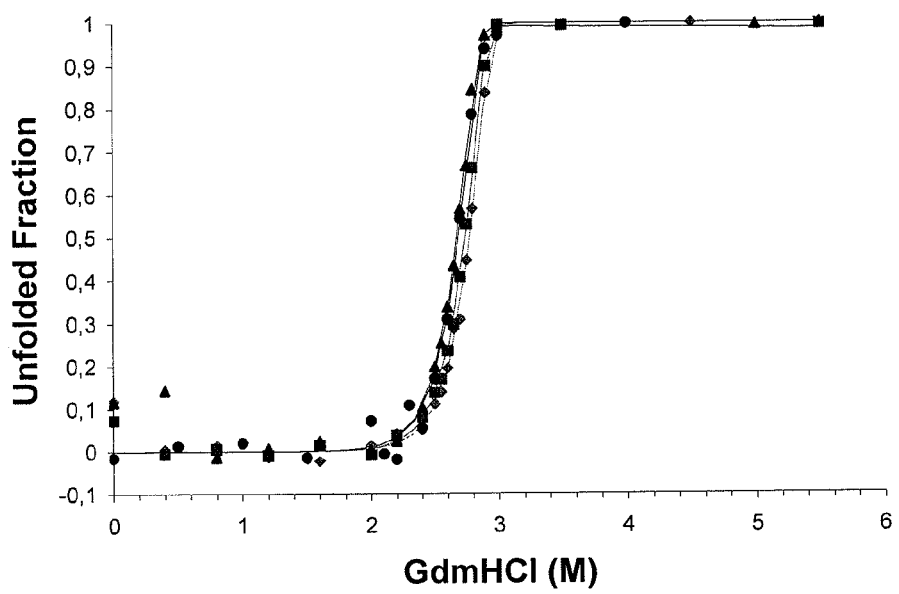
Figure 10:
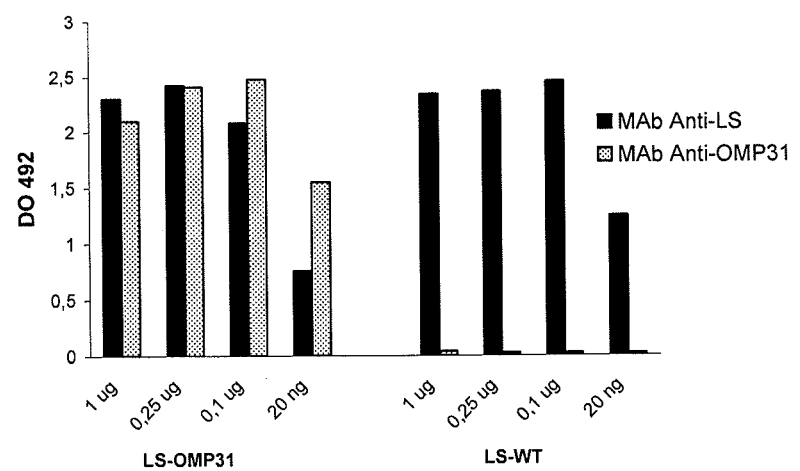

The purification second step was performed by chromatography in a Superdex 200 (Amersham, UK) molecular exclusion column. See FIGS. 6 and 7. For this, the chimera peak was concentrated in a Centriprep (Millipore, USA) tube and injected in the column for elution with PBS. The presence of the chimeric protein in the peaks was evaluated by SDS-PAGE.

Figure 11:
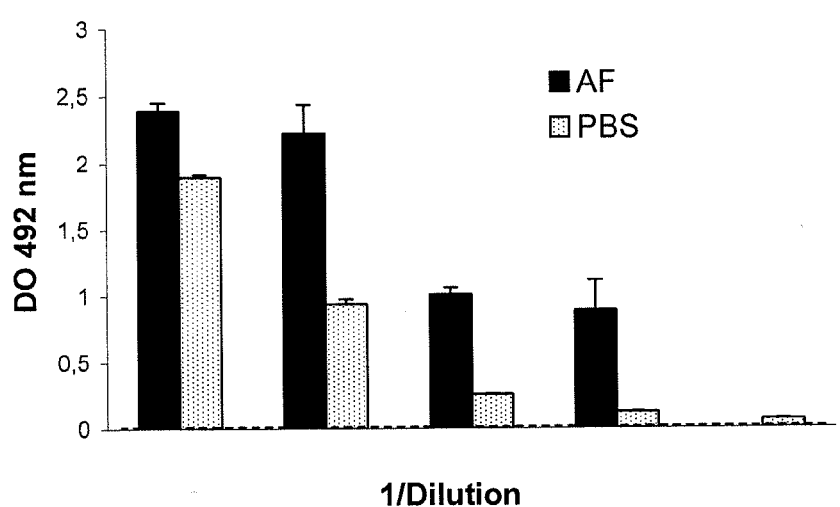

The construction of the BLS-OMP31 chimeric gene was performed by using molecular biology techniques known in the art. See Sambrook, et al., *Molecular Cloning: A Laboratory Manual*, Cold Spring Harbor Laboratory Press, New York, N.Y., 1989; Brown, *Gene Cloning*, Chapman & Hall, London, England, 1995; Watson, et al., *Recombinant DNA*, 2nd Ed., Scientific American Books, New York, N.Y., 1992 and Davis et al., *Basic Methods in Molecular Biology*, Elsevier Science Publishing Co., New York, N.Y., 1986, Alberts, et al., *Molecular Biology of the Cell,* $4^{th}$ Ed., Garland Science, New York, N.Y., 2002.

EXAMPLE 2

BLS-OMP31 Chimera Stability

The first proof that the BLS-OMP31 chimeric protein has adopted a decameric folding was obtained trough the light scattering technique. This procedure was used to calculate the molecular size of the proteins in solution. To conduct these assays, a molecular exclusion column was joined to a light scattering detector. As the protein eluted from the column its molecular weight was determined.

According to this method, the calculated BLS molecular weight was 163 kDa while that of the BLS-OMP31 chimera was 215 kDa. The theoretical molecular weights of the native BLS and BLS-OMP31 decamers were of 174.4 and 197.8 Kda, respectively. Taking to account that this method is 90% accurate, this result suggests that the BLS-OMP31 chimera forms a decamer very much alike the native BLS protein.

The folding chimeric proteins was studied through circular dichroism. The circular dichroism measurements were performed in the J-810 spectropolarimeter (Jasco, UK), set up at a reading speed of 100 nm/min, response time of 4 s and a band width of 1 nm. Quartz trays of 1, 2 or 5 mm (Hellma) were used. The samples were assayed in a 50 mM pH 7 phosphate buffer. The overlay of the circular dichroism spectra of the BLS-OMP31 chimera and native BLS showed that the general folding of both proteins were very similar. See FIG. 8. Thus, it was confirmed that the chimeric proteins folded properly like decamers, with a secondary structure comparable to that of the native protein.

Next, it was studied whether the substitutions at N-terminal of the chimeric proteins affected their stability. To this end, the induced denaturalization of the chimeras by guanidine hydrochloride (Gdm-HCl) and temperature was studied through circular dichroism.

From denaturalization-to-balance curves, it was possible to obtain several thermodynamic parameters, such as the change of free energy associated with unfolding. With this parameter, the conformational stability typical of a protein was evaluated. See Pace, et al, *Methods Enzymol.,* 131: 266-80 (1986). To assess the change of free energy associated with the unfolding of each protein, the research data was adjusted to a theoretical descriptive curve. This diagram depicted the correlation of the equilibrium constant between the folded and unfolded stages of the chimeric protein and varying concentrations of the denaturalizing agent.

To conduct these experiments, the same amount of protein (0.1 μM of decamer) was incubated with increasing concentrations of the denaturalizing agent. The solutions for each point of the curve were prepared from a matrix solution of 6 M guanidine-HCl (ICN, ultra pure), 50 mM phosphate, pH 7. The samples were incubated for three hours at room temperature and were centrifuged before measurement. The circular dichroism measurements were performed in trays of 5 mm at 25° C. The reversibility of the denaturalization by guanidine of the BLS native protein and the BLS-OMP31 chimeric protein was thus demonstrated.

The denaturalization-to-balance curves were adjusted to a two step dissociation model. According to this model the decamer separated firstly into two equal pentamers. In the second step of denaturalization, each of these pentamers dissociated further into five unfolded monomers. The formulas describing this transition were derived from those already proposed for monomeric proteins. See Zylberman, et al, *J. Biol. Chem.,* 279(9):8093-8101 (2004).

The thermodynamic values obtained for the native BLS and BLS-OMP31, show that the replacement of the BLS N-terminal end did not affect the decamer stability. See FIG. 9. Therefore, it was confirmed that the BLS chimeras form properly folded decamers and that their stability is similar to those of the native BLS.

EXAMPLE 3

BLS-OMP31 Chimera Antigenicity and Immunogenicity

The antigenicity of the BLS-OMP31 was studied by measuring its capacity to bind to a specific monoclonal antibody against the inserted peptide (A59/10F09/G10 monoclonal antibody) and to a specific monoclonal antibody against the native BLS protein (BI24 monoclonal antibody). See Vizcaíno, et al., *Infect. Immun.,* 69(11):7020-28, (2001); Goldbaum, et al., *J. Clin. Microbiol.,* 31:2141-2145 (1993). This procedure allows assaying the antigenicity of both the insert and the protein core. The antigenicity was assayed by ELISA. See FIG. 10.

The BLS-OMP31 was identified both by the monoclonal antibody against the native BLS and by the monoclonal antibody against the inserted peptide. The native BLS was only identified by the first antibody, as expected. This result indicates that the inserted peptide preserved its antigenic properties when displayed by the chimera. In addition, it was also showed that the folding of the chimera did not affect the affinity of anti-BLS antibody to the protein core. Both antibodies detected up to 20 ng of chimera per well.

Then, the BLS-OMP31 capacity to induce a specific humoral immune response against the inserted peptide was evaluated. This capacity was analyzed in mice with and without the assistance of adjuvants. The experiment was performed with two groups of five mice each. The "AF" group received three doses, by intraperitoneal route, of 25 ug of protein in emulsion with Freund adjuvant at 0, 20 and 40-day intervals. The first dose was administered with a complete Freund's adjuvant. The remaining doses were administered with an incomplete Freund's adjuvant. The "PBS" group had the same treatment but the chimeric protein was injected without adjuvant. Blood was drawn 7 days after the third immunization and the sera reactivity against the OMP31 membrane protein was assayed by ELISA. See FIG. 11.

A strong response against OMP31 was obtained in the mice immunized with the chimera and the adjuvant. The serologic response obtained from the mice immunized with the chimeric protein with and without the adjuvant was also relevant. These results show that mice immunized with the BLS-OMP31 chimera with or without adjuvant have specific immune responses against the inserted peptide.

A rabbit was injected with BLS-OMP31 chimera with adjuvant according to the following protocol:

First dose, day 0: 200 µg BLS-OMP31 in 1 ml of PBS+1 ml of complete Freund's adjuvant, by intramuscular injection.

Second dose, day 22: 200 µg BLS-OMP31 in 1 ml of PBS+1 ml of incomplete Freund's adjuvant (IFA), by subcutaneous injection.

Third dose, day 45: 200 µg BLS-OMP31 in 1 ml of PBS+1 ml of IFA, by intramuscular injection.

Fourth dose, day 155: 200 µg BLS-OMP31 in 1 ml of PBS+1 ml of IFA, by subcutaneous injection.

Blood samples were drawn at $31^{th}$, $52^{nd}$ and $180^{th}$ day. The samples were centrifuged and the serum was frozen.

Figure 12:
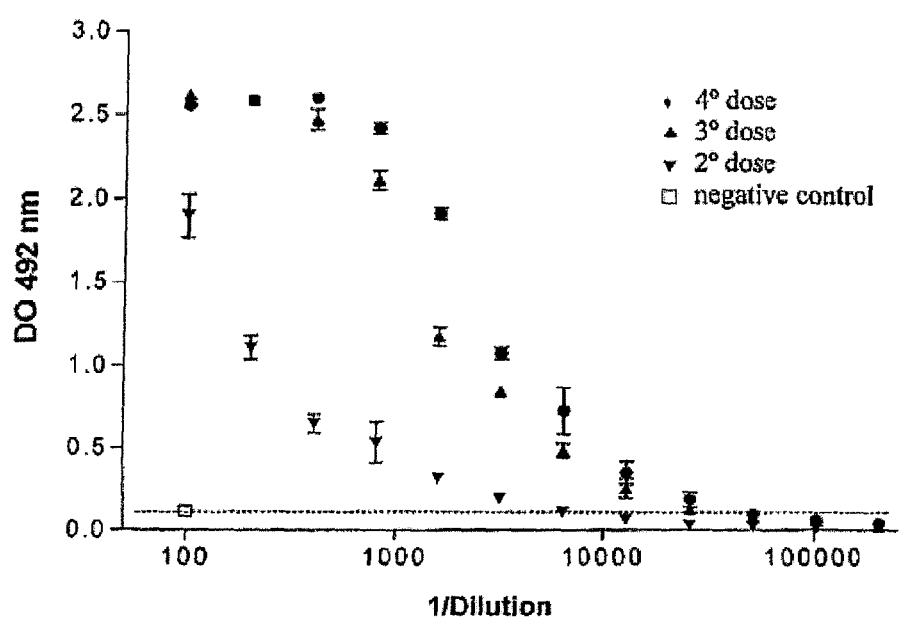
Figure 13:
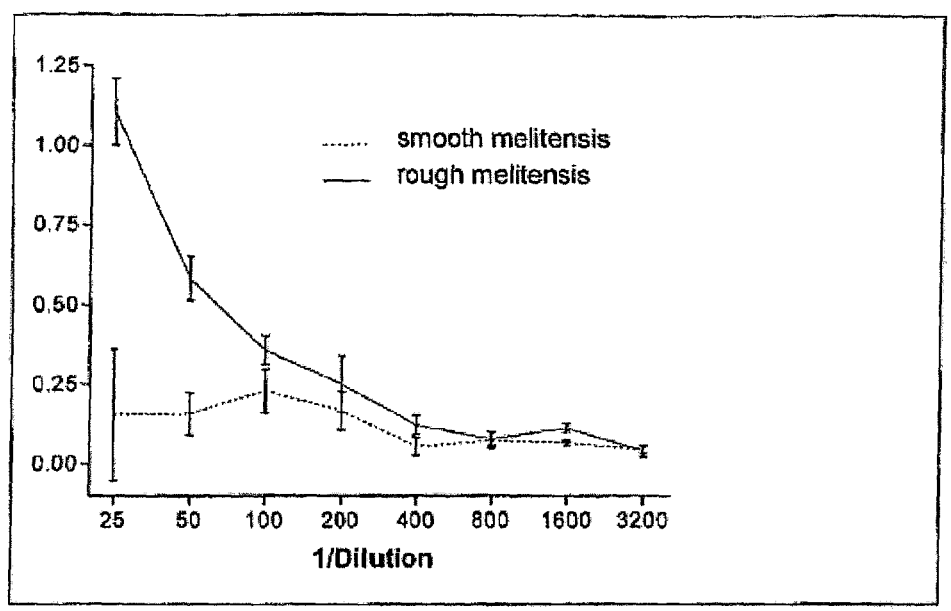

The antisera collected after the $2^{nd}$, $3^{rd}$ and $4^{th}$ doses of the antigen were titrated by ELISA against the OMP31 membrane protein. See FIG. 12. The assayed antisera titer was of 3,200, 12,800 and 25,600 for sera corresponding to the $2^{nd}$, $3^{rd}$ and $4^{th}$ doses, respectively. The base line was defined as the maximum dilution capable of identifying the antigen over the negative serum. The immunized rabbit showed a strong specific immune response against the OMP31. Since the anti native BLS serum did not identify the OMP31, this high reactivity was due to a response of specific antibodies against the peptide inserted in the chimera. See FIG. 13, negative control.

The OMP31 protein used in the ELISA assays was produced recombinantly in *E. coli*. Since this molecule is a membrane protein, it cannot be kept in an aqueous solution; and was, therefore, obtained under denaturalizing conditions. In the assays performed, it was not demonstrated that the antisera were able to identify the OMP31 chimera in its native conformation as a bacterial membrane protein. This property is important to evaluate the potential effectivity of the chimera as an immunogen capable of providing humoral immunity against *Brucella*. To assess this property, ELISA assays were performed using a smooth and a rough strain of *B. melitensis* H38, as antigens. See FIG. 13. The reactivity of a serum against whole bacteria is difficult to evaluate in general due to the complexity of the antigen used. However, the assay showed that the anti BLS-OMP31 serum specifically identified the OMP31 insert in the membrane of the rough strain. The reactivity of this serum against the smooth strain was not different from that shown by the anti native BLS serum. This result is completely consistent with the data published for the A59/10F09/G10 monoclonal antibody. See Vizcaíno, et al., supra. This antibody, specific for the insert included in the BLS-OMP31 chimera, has strong reactivity with the rough, but not the smooth *B. melitensis* H38.

EXAMPLE 4

BLS-OMP31 Immunogenicity, as a Vaccine, to DNA

The codifying sequence for the BLS-Omp31 was subcloned in the vector pCI-neo (Promega, USA), including the restriction sites in the 5' ends (framed) of the primers and the Kozak consensus sequence (underlined). Hence, the following oligonucleotides were built:

BLS-OMP31 "sense":
(SEQ ID NO: 35)
5'TAAGAA GAATCC <u>ACCACCATG</u> CAT ACC GCC GGT TA 3'.

BLS-OMP31 "anti-sense":
(SEQ ID NO: 36)
5'TGT CCA CCA GTC AT GCTAGCT CAG ACA AGC GCG ATG C 3'.

Such sequence was amplified by PCR using the pET-BLS-OMP31 plasmid as a template. The PCR product and the vector were digested with the corresponding restriction enzymes and then a ligation reaction was performed. The obtained construct was checked by sequencing. The pCI-BLS-OMP31 plasmid was amplified in *E. coli* JM109 cells and further purified by "mega prep" columns (Quiagen, UK). DNA purity and concentration were assessed by spectrophotometry at 260/280 nm. The plasmid preparation contained less than 0.05 units of endotoxin per 100 µg of DNA, determined by a limulus amebocyte lysate analysis kit (Sigma, USA).

Groups of—Balb/c mice were inoculated with 100 µg of pCI-BLSOMP31 plasmid and the control plasmid without insert (pCI) in physiological solution by intramuscular (im) and intradermal (id) route at weeks 0, 2, 4 and 6. The animals blood was extracted by retroorbital route at days 0, 15, 30, 45, 60 and 75 after the first immunization. The sera were kept at −20 C for the detection of specific antibodies.

Figure 14:
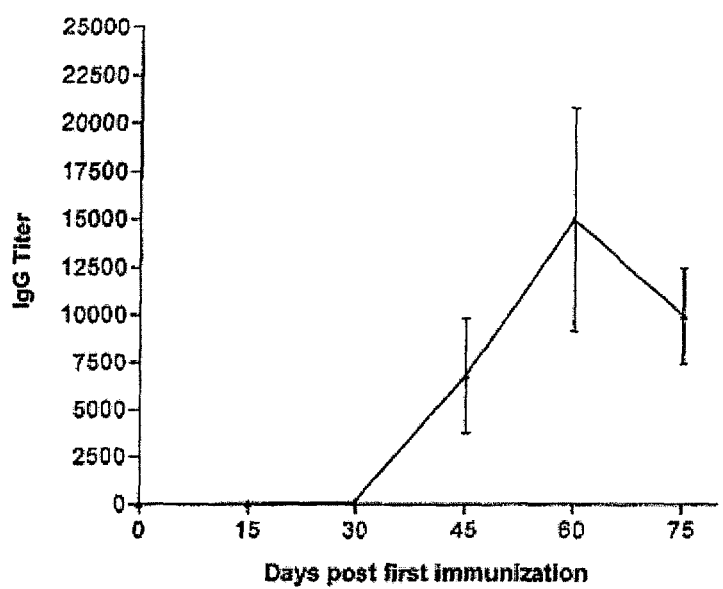

The anti-OMP31 humoral response induced by the immunization with the BLS-OMP31 DNA vaccine (pCI-BLSOMP31) was analyzed by indirect ELISA using the recombinant OMP31 protein as an antigen. After immunization, all animals developed a humoral immune response. A high level of the IgG isotype produced specifically against the Omp31 protein was observed. See FIG. 14.

The preparation, amplification, purification and use of pCI-BLS-OMP31 plasmid as a DNA vaccine was performed using molecular biology techniques and methods for the preparation and administration of pharmaceutical compounds known in the art. See Schleef, M, Ed, *Plasmids for Therapy and Vaccination*, Wiley-VCH Verlag GmbH, Weinheim, Germany, 2001.

EXAMPLE 5

Mixed BLS Chimeras

The fact that lumazine synthase of *Brucella* spp. dissociates reversibly when treated with high concentrations of guanidine chloride was used to construct mixed chimeras. See Zylberman, et al., J. Biol. Chem. 279 (9):8093-8101 Two chimeras with marked differences in their insert size and isoelectric points were constructed. This strategy was followed in order to distinguish more easily the decamers formed by the mixed chimeras.

To this end, the KETc1 peptide shown in FIG. 15 was used in addition to the OMP31 peptide already described. The KETc1 peptide derives from a protein of *Tenia solium* and has been described as highly protective against murine and pig neurocysticercosis. See Huerta, et al. *Vaccine* 20:62-266 (2001); Toledo, et al., *Infect. Immun.*, 69:1766-1773 (2001).

The BLS-KETc1 chimeric protein was obtained according to the following protocol:

1. Cloning
   a) The pBLS-OMP31 plasmid was digested with the Nsi I and Afl II restriction enzymes to remove the codifying sequence corresponding to the 27 amino acids from the 48-74 sequence of the OMP31 protein. The OMP31 protein codifying sequence was extracted.
   b) The codifying sequence for the 14 amino acids of the KETc1 peptide was linked to the open cassette in a) by incubation overnight of the open cassette of the pBLS-OMP31$^{-OMP31}$ plasmid with DNA T4 ligase enzyme at 16° C. The BLS-KETc1 reading frame was thus obtained. The insertion was confirmed by the sequencing of the reading frame. This reading frame was called BLS-KETc1 chimera, of SEQ ID NO:21, and the expression plasmid, pBLS-KETc1.

This procedure can also be performed following the protocol indicated in step 1) of Example I through the cleavage of BLSm cassette (SEQ ID NO:12) with the Nsi and Afl I restriction enzymes and its further linkage with the KETc1 insert. Thus, the BLS-KETc1 reading frame and the pBLS-KETc1 plasmid are also obtained.

This experience was repeated using the DNA sequences of the mutated BLS SEQ ID NO:13, SEQ ID NO:14, SEQ ID NO:15, SEQ ID NO:16, SEQ ID NO:17 and SEQ ID NO:18. Similar results were obtained.

2. Transformation

A competent strain of *E. coli* BL21 (DE3) bacteria was transformed by thermal shock with the pBLS-KETc1 plasmid obtained according to the protocol above. Afterwards, bacteria were cultured in agar plates including LB-agar/ampicilin to choose those transformed with the plasmid.

3. Expression and Purification of the BLS-KETc1 Chimeric Protein 2 ml of a LB/ampicilin medium was inoculated to a colony extracted from agar plates for small-scale expression tests. The colony was shaked and incubated at 37° C. The saturated culture was induced with 2 μl of 1M IPTG. Three hours later, 100 μl of culture was removed and centrifuged. The resulting pellet was resuspended in 25 μl of sample buffer 1× for its analysis by SDS-PAGE 17%

A 5-ml preculture of the transformed strains was cultured to saturation according to the step above with 500 ml of LB/ampicilin. The culture was incubated and shaked at 37° C. It was induced with 0.5 ml of 1M IPTG to reach an optical density of 0.6-0.8 at 600 nm The culture was removed three hours later and was centrifuged at 4,000 g for 20 minutes. The pellet was resuspended in 15 ml of suspension solution (50 mM Tris, 5 mM EDTA, 1% Triton X-100, pH 8.0).

The suspension was sonicated for at 1 minute intervals every minute for 5 minutes and was centrifuged at 20,000 g for 30 minutes. The pellet was resuspended in 15 ml of suspension solution without Triton X-100 and the sonicate process was repeated. The procedure was repeated for a third time. The chimera expressed in the cytoplasm was contained in three sonicate supernatants while inclusion bodies were contained in the pellet.

The inclusion bodies were resuspended in PBS buffer with 8 M urea and were left overnight at room temperature. The resuspension was dialyzed against PBS for two days with a buffer change. The sample was centrifuged and the supernatant was dialyzed against buffer A (50 mM Tris/HCl, pH 8.5). The first purification step was performed by anionic interchange chromatography in a MonoQ or a Q-Sepharose (Pharmacia, USA) column in a FPLC equipment (Pharmacia, USA). The sample was injected in the balanced column with buffer A and was eluted by linear gradient up to 50% of buffer B (buffer A+1 M NaCl).

The purification second step was performed by chromatography in a Superdex 200 (Amersham, UK) molecular exclusion column. For this, the chimera peak was concentrated in a Centriprep (Millipore, USA) tube and injected in the column for elution with PBS. The presence of the chimeric protein in the peaks was evaluated by SDS-PAGE.

The construction of the BLS-KETc1 chimeric gene was performed by using molecular biology techniques known in the art. See Sambrook, et al., supra; Brown, supra; Watson, et al., supra; Davis et al., supra, Alberts, et al., supra.

Figure 16:
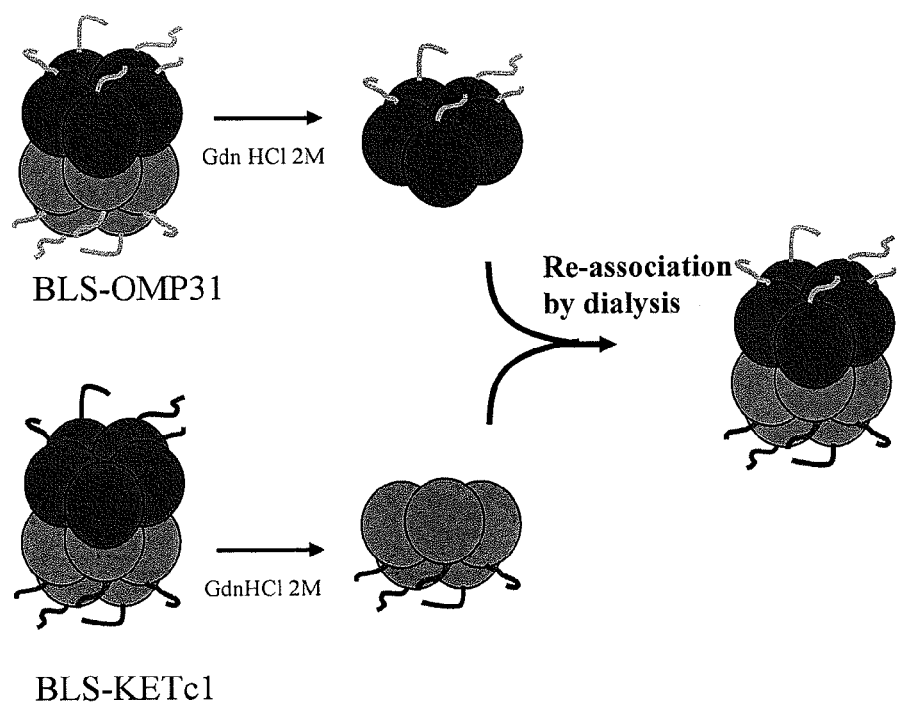

The BLS-OMP31 and BLS-KETc1 chimeras were unfolded in 2 M of guanidine chloride, mixed in equimolar concentrations and re-associated through dialysis. Adding 2 M guanidine, the decamers were separated thus generated pentamers that preserved their secondary structure. When the guanidine was removed through dialysis, the pentamers were re-associated forming decamers again. See Zylberman, et al., *J. Biol. Chem.*, 279(9): 8093-8101 (2004). In this manner, a mixture of BLS chimeras was produced. See FIG. 16.

The re-association product was purified by interchange chromatography in a MonoQ (Amersham, UK) anionic interchange column. The results were compared to the elution profile of each separate chimera (a sample without dissociation) according to the following protocol: the BLS-KETc1 chimera was eluted at 16.8% of buffer B (this particle was estimated the most basic in view of insert theoretical isoelectric point) and the BLS-OMP31 chimera was eluted at 35.8% of the same buffer. The re-associated sample was separated yielding three different peaks, the first corresponded to the pure BLS-KETc1 chimera; the second and largest peak corresponded to the mixed chimera and the last peak corresponded to the pure BLS-OMP31 chimera. See FIG. 17 A.

The sample corresponding to the second peak was analyzed by SDS-PAGE and native PAGE. The results demonstrated that the sample corresponded to a mixed chimera formed by KETc1 peptide displayed in the five amino termini of one pentamer and by OMP31 peptide displayed in the five amino termini of the other pentamer. See FIGS. 17 B1 and B2.

This outcome showed that proposed strategy of separating, mixing and re-associating the modified proteins was effective to yield a mixed chimera where five copies of two different peptides were displayed by the BLS decameric structure. See FIG. 16. The mixtures may have different characteristics depending on the nature of the inserts (e.g. one insert might be directed to an specific cell traffic while the other might induce a particular immune response).

EXAMPLE 6

Immunization with Mixed BLS Chimeras

The mixed BLS-OMP31-KETc1 chimeras was administered with adjuvants to mice to evaluate its capacity to induce a specific humoral immune response. The experiment was performed with a group of five mice. The group received three doses of 25 μg of protein in emulsion with a Freund's adjuvant by intraperitoneal route at 0, 20 and 40 days. The first dose was applied with a complete adjuvant. The second and third doses were applied with an incomplete adjuvant. Blood was drawn 7 days after the third immunization and the sera reactivity was assayed against the OMP31 and KETc1 synthetic peptides by ELISA. See FIG. 18.

A strong response against both peptides was obtained in immunized mice with the mixed chimeras with adjuvant. This demonstrated that mice immunized with the BLS-OMP31-KETc1 mixed developed simultaneously a specific immune response against both inserts.

EXAMPLE 7

Cellular Immune Response Against BLS Chimeras

Groups of five BALB/c mice were immunized with 50 µg/mouse of the BLS-KETc1 chimera emulsified in saponin and with 10 µg/mouse of the KETc1 synthetic peptide emulsified in saponin to assess the specific cellular immune response induced by the BLS-KETc1 chimera against the inserted peptide. The mice were immunized twice within a 10-day interval by subcutaneous route.

The spleens of both groups were aseptically removed three days after the last immunization. The spleen cells were resuspended in an RPMI 1640 Gibco (InVitrogen Corp., USA) culture medium, supplemented with L-glutamine (0.2 mM), 2-mercaptoethanol (0.05 mM), non-essential amino acids (0.01 mM), penicillin (100 U/ml), streptomycin (100 µg/ml) and fetal bovine serum 10% (FBS). A culture medium, the KETc1 peptide or the BLS-KETc1 chimera (10 µg/ml) were added to different cell cultures. The cells were suspended in flat-bottom culture microplates at a concentration of $2 \times 10^5$ cells per 200 µl of final volume. They were kept in a 5% $CO_2$ humidified environment at 37° C.

After 72 hours, 1 µCi of [methyl-$^3$H] timidine (Amersham Biosciences, UK) was added to each culture. The cells were seeded and the tritrated timidine level of incorporation was measured in a 1205 Betaplate™ liquid scintillation counter (Wallac Oy, FI). All the assays were performed in triplicate.

The assay showed that the spleen cells of mice immunized with the BLS-KETc1 chimera proliferated in cultures in the presence both of the peptide and the chimera. This result clearly indicated that the BLS-KETc1 chimera was able to induce a specific cellular immune response against the KETc1 peptide inserted in BLS. See FIG. 19.

EXAMPLE 8

Multidisplay of Protein Domains by BLS Chimeras

The BLS can be modified to display not only peptides but also complete protein domains in its ten amino termini. In order to demonstrate this alternate use a BLS-RBD3 chimera was constructed by linking the modified BLS codifying sequence and the codifying sequence of the RBD3 proteic domain of the murine protein Staufen-1. See FIGS. 20 and 21.

The BLS-KETc1 chimeric protein was obtained according to the following protocol:
1. Cloning
   a) The pBLS-OMP31 plasmid was digested with the Nsi I and Afl II restriction enzymes to remove the codifying sequence corresponding to the 27 amino acids from the 48-74 sequence of the OMP31 protein. The OMP31 protein codifying sequence was extracted.

b) The codifying sequence for the 75 amino acids of the RBD3 domain of the murine protein Staufen was linked to the open cassette in a) by incubation overnight of the open cassette of the pBLS-OMP31-OMP31 plasmid with DNA T4 ligase enzyme at 16° C. The BLS-RBD3 reading frame was thus obtained. The insertion was confirmed by the sequencing of the reading frame. This reading frame was called BLS-RBD3 chimera, of SEQ ID NO:22, and the expression plasmid, pBLS-RBD3.

This procedure can also be performed following the protocol indicated in step 1) of Example 1 through the cleavage of BLSm cassette (SEQ ID NO: 16) with the Nsi and Afl I restriction enzymes and its further linkage with the RBD3 insert. Thus, the BLS-RBD3 reading frame and the pBLS-RBD3 plasmid are also obtained.

This experience was repeated using the DNA sequences of the mutated BLS SEQ ID NO:13, SEQ ID NO:14, SEQ ID NO:15, SEQ ID NO:16, SEQ ID NO:17 and SEQ ID NO:18. Similar results were obtained.

2. Transformation

The pBLS-RBD3 plasmid obtained according to the above protocol was inserted in *E. coli* BL21 (DE3) bacteria by thermal shock transformation. Afterwards, the bacteria were seeded in an LB medium in the presence of ampicillin. The gene expression was induced with IPTG 1 mM for 4 hours at 28° C.

3. Expression and Purification of the BLS-RD3 Chimeric Protein

The protein was expressed in inclusion bodies, washed with 4 and 6 M urea solutions and solubilized in a buffer Tris/HCl 50 mM, urea 8 M, EDTA 5 mM, β-ME 5 mM, PMSF 1 mM, pH 8 by magnetic stirring for 16 hours at 4° C. The solubilized protein was purified under denaturalizing conditions in a Q-Sepharose ionic interchange column applying a linear gradient between 0 and 1 M NaCl in a buffer Tris/HCl 50 mM, 8 M urea, pH 8.5. The eluted protein was refolded by dialysis against the PBS buffer and purified by a heparin Hyper D column. For elution, a buffer Tris/HCl 50 mM, NaCl 1.2 M, pH 8 was used.

FIG. 22 shows the SDS-PAGE, circular dichroism and light scattering analyses of the BLS-RBD3 chimera obtained through the method described above.

The SDS-PAGE analysis shows the high degree of purity of the BLS-RBD3 chimera obtained. The small anomaly observed in electrophoretic mobility is attributed to the high density of the RBD3 domain positive charge. The similarity of the BLS-RBD3 circular dichroism spectrum with its theoretical spectrum, calculated by the combination of the spectra of the BLS and the RBD3 domain of the isolated murine protein Staufen-1, indicated that the chimera was well-folded. The chimera molecular weight (257 kDa), calculated from its run in the molecular filtering column connected in series to a light scattering detector and a refraction index detector, indicated that BLS-RBD3 chimera presented a decameric structure.

The construction of the BLS-RBD3 chimeric gene was performed by using molecular biology techniques known in the art. See Sambrook, et al., supra; Brown, supra; Watson, et al., supra; Davis et al., supra, Alberts, et al., supra.

EXAMPLE 9

Production of Wide Spectrum Antibodies by Immunization with BLS Chimeras

The BLS-Staufen chimera was used as an immunogen to obtain antibodies against the Staufen RBD3 domain. 5 Balb/c mice were inoculated with 80 μg of the BLS-RBD3 chimera in a buffer 200 μl HCl 50 mM, NaCl 1.2M, 50 mM phosphate, pH 8 without adjuvant twice, at a 14-day interval by intraperitoneal route. As a control, 5 mice of the same strain were immunized with a mixture of BLS proteins and the Staufen RBD3 domain, in the same chimera-including mass. The mice were bleeded through retroorbital punction fifteen days after the last immunization. A serum was prepared through centrifugation at 1000×g for 10 min. Sera reactivity against RBD3 was assayed by ELISA in 96-well plate with the glutathione S-transferase-RBD3 (GST-RBD3) fusion protein. Mouse anti-immunoglobulin conjugated to caprine peroxidasa (DakoCytomation, USA) was used as a secondary antibody. The reaction was developed with orthophenildyamin (OPD) and was stopped with 4 N sulphuric acid. The optical density was determined by an ELISA reader at 492 nm FIG. 23 shows a representative example of the humoral immune response developed by both groups. As observed, immunization with the BLS-RBD3 chimera caused a strong anti-RBD3 antibody response. No reactivity was observed against the peptide in mice inoculated with the BLS and RBD3 mixture.

EXAMPLE 10

Production of Monoclonal Antibodies by Immunization with BLS Chimeras

Figure 24:
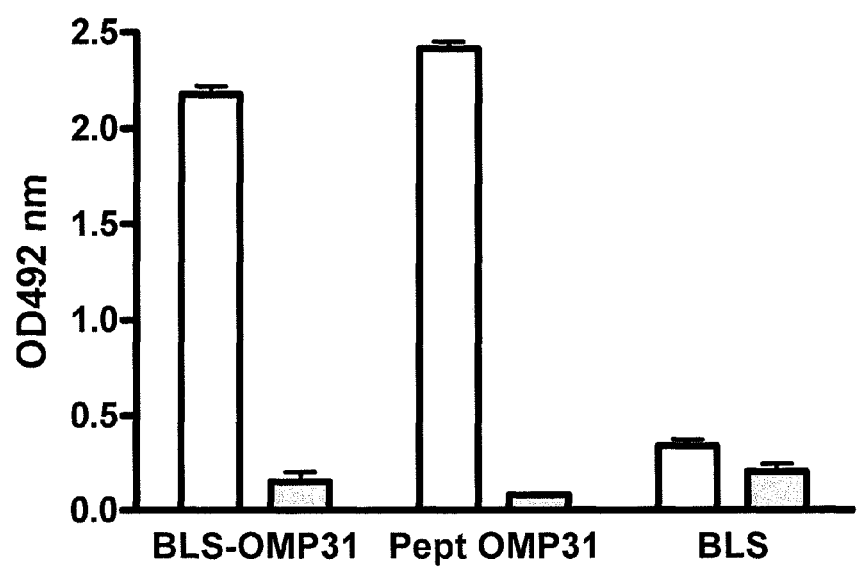

The capacity to generate specific monoclonal antibodies against the OMP31 peptide was assessed from splenocytes of mice immunized with the BLS-OMP31 chimera. The experiment was performed with a group of five mice. The group received three doses, by intraperitoneal route, of 25 µg of protein in emulsion to the medium with Freund's adjuvant at 0, 20 and 40-day intervals. At day 60, 25 µg of BLS-OMP31 dissolved in PBS was inoculated by peritoneal route in the mouse that showed a better response against the OMP31 peptide. The spleen of such mouse was removed and the splenocytes were merged with the NSO myeloma cells. The resulting hybridomas were selected in a HAT medium and their culture supernatants were assayed to measure reactivity against the OMP31 peptide by ELISA. The hybridoma that showed a higher reactivity was cloned by limit dilution. FIG. 24 shows the AcMo 37F7 reactivity against the OMP31 peptide and the whole OMP31 protein. A strong response against both was obtained. This demonstrated that mice immunized with the BLS-OMP31 chimera developed a specific immune response against the inserted peptide. This experience also shows that specific monoclonal antibodies could be produced using the BLS chimeras.

EXAMPLE 11

Use of BLS Chimeras as Biosensors

Biosensors allow the detection of a specific interaction among macromolecules, which is visualized by the increase of a signal proportional to the mass accumulation on a reactive surface. The BLS-OMP31 modified protein was used to study the application of the BLS chimeras as a peptide and proteic domain carrier for the development of biosensors. To this end, the reaction between the BLS-OMP31 and the AcMo 37F7 described in the previous example was analyzed further.

The BLS-OMP31 chimera was used to derivatize a dextran carboximethyl plate (IAsys Affinity Sensors, Thermo, USA). For that purpose, a solution including 80 µg/ml of BLS-OMP31, in a buffer of 10 mM sodium acetate pH 5.5, was incubated in a plate previously derivatized by the EDC/NHS reagent. After immobilizing a signal corresponding to 800 arc sec (equal to 5 ng of antigen), the reactive surface was blocked with diethylamine. After derivatization, the anti-OMP31 AcMo 37F7 reactivity was studied, for which 50 µl of culture supernatant were incubated in the previously activated plate.

Figure 25:
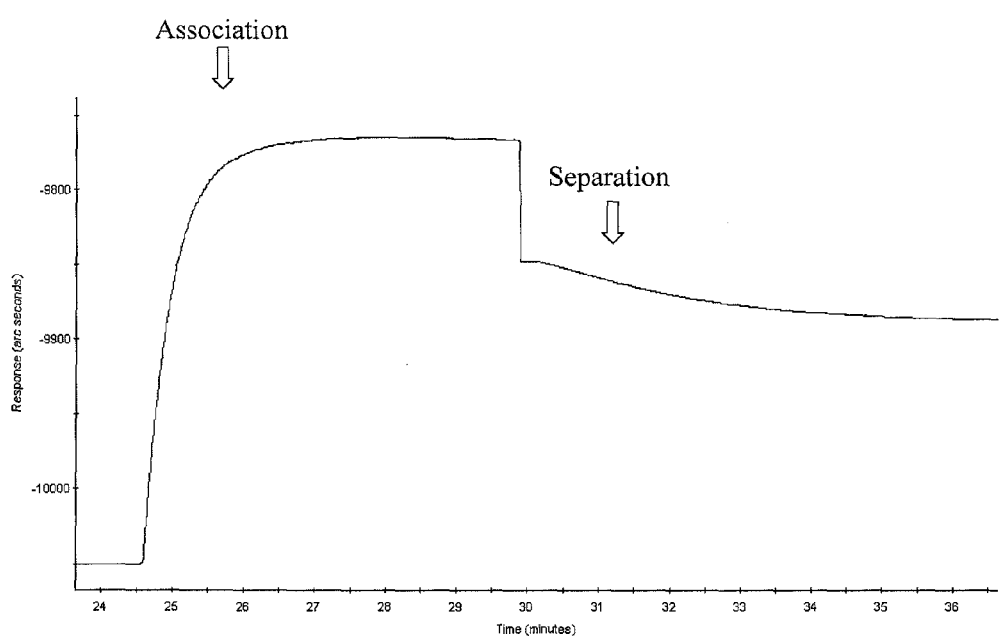

As observed in FIG. 25, the AcMo 37F7 reacted strongly, providing a signal of approximately 300 arc sec. In the separation phase, the buffer PBS+Tween was washed and added, observing a drop in the signal corresponding to the AcMo separation of the solid phase. This example clearly shows that the chimera is able to detect antibodies directed against the peptide in the biosensor.

EXAMPLE 12

Activation of Dendritic Cells by BLS

The BLS capacity of activating dendritic cells was analyzed. To that end, the activation levels of different markers were studied in these cells 18 hours after incubation with BLS. Bone marrow cells from Balb/c mice were cultured in Petri plates with a RPMI medium with 2 mM L-glutamine, 100 U/ml-penicillin, 100 µg/ml streptomycin, 50 µM 2-mercaptoethanol and 10% fetal bovine serum (medium R10), supplemented with mouse granulocyte and macrophages colony stimulating factor (mGM-CSF) in an incubator with a 5% $CO_2$ environment at 37° C. The culture medium was replaced at days 3, 6 and 8. At day 9, the non-adhered cells were taken and centrifuged at 300×g for 8 minutes. The cells were then incubated at a concentration of $2 \times 10^6$ cells/ml in a final volume of 1 ml with BLS (1, 5 or 10 µM) or without BLS in R10 medium for 18 hours (n=4). Afterwards, $4 \times 10^5$ cells per 200 µl of final volume were centrifuged and incubated with the following monoclonal antibodies (Pharmingen) conjugated to fluorescein isothiocyanate (FITC): anti-CD40, anti-CD80, anti I-$A^d$ or anti-CD86, and with the anti-CD11c monoclonal antibody conjugated to phycoerythrin (PE). Three washings were performed and the cells were extracted with a FACScan cytometer (Becton Dickinson, USA). The obtained data was analyzed with the CellQuest (Becton Dickinson, USA) software.

In the cells incubated with BLS, within the subpopulation of CD11c$^+$ (75-80%), significant increases were observed in the percentages and mean fluorescence of cells expressing CD40, CD80, I-$A^d$ y CD86. The experiment was performed three times, obtaining similar results. FIG. 26 shows representative histograms of the CD40 expression (A) and of the I-$A^d$ (B) in CD11c$^+$ cells treated with or without BLS.

A similar activation by BLS was observed in dendritic cells of C3H/HeJ mice (non responders to LPS) or when pre-incubating the BLS protein with polymyxin B, so as to eliminate LPS of E. coli.

These results demonstrated that the BLS is able to activate dendritic cells.

EXAMPLE 13

Production of Molecular Assemblies with Protein Domains through Adaptor Peptides Linked to BLS Chimeras The BLS protein could be modified in its amino termini to display whole proteic domains. This could be accomplished by the formation of molecular assemblies. In these clusters, complementary heterodimeric peptides are incorporated into the modified BLS protein and the target. Afterwards, the high affinity between the heterodimers links the target molecule and the modified BLS protein. The use of high affinity heterodimers is useful to avoid affecting the proper folding of the carrier protein. To demonstrate this application of the BLS chimeras, two heterodimerization peptides known in the art, $RR_{12}EE_{345}L$ y $EE_{12}RR_{345}L$, were used. See Moll, et al., *M Protein Sci.,* 10:649-655 (2001). See FIG. 27. This strategy allowed the construction of molecular assemblies, including ten copies of the domain combined with the BLS. The assembly was performed in vitro, which made possible to control the stoichiometry of the process. This system also enables expressing the antigen in a recombinant system different from BLS. See FIG. 28A and FIG. 28B.

1. Construction of Fusion Protein $BLS\text{-}RR_{12}EE_{345}L$

The peptide $RR_{12}EE_{345}L$ was cloned in the N-terminal end of the BLS. See FIGS. 28A, 28B and 29. The $K_{49}$ residue located in BLS and $RR_{12}EE_{345}L$ linker region was substituted for serine. The $BLS\text{-}RR_{12}EE_{345}L$ chimeric gene was cloned in the pET11a vector. A competent strain of *E. coli* BL21 (DE3) bacteria was transformed with the resulting vector. Afterwards, the bacteria were cultured in a LB-agar/ampicillin culture medium The gene expression was induced with 1M IPTG for 16 hours at 37° C. The protein was expressed in the inclusion bodies.

Figure 30:
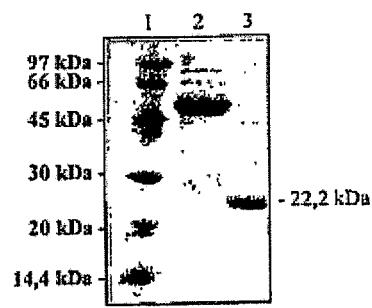
Figure 31:
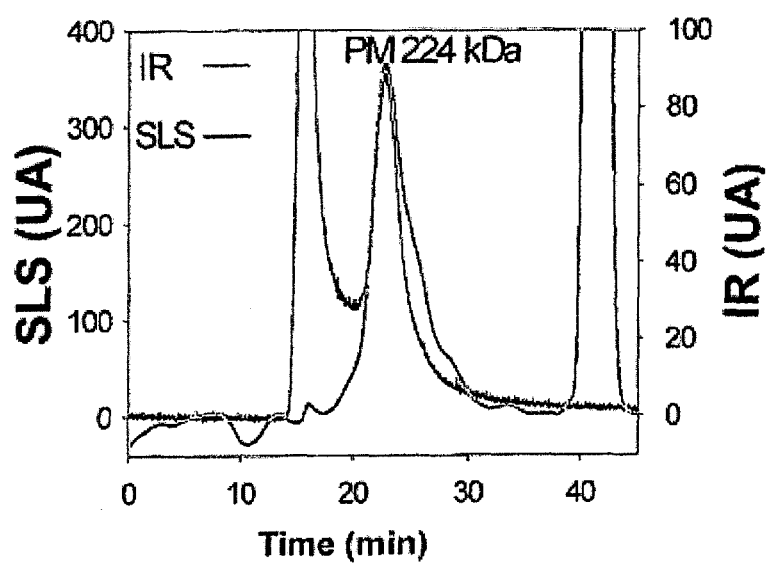

The inclusion bodies were washed with a buffer 50 mM Tris/HCl, 5 mM EDTA, 5 mM β-ME, 1 mM PMSF, pH 8. The dissolved protein was treated with a buffer 50 mM Tris/HCl, 8 M urea, 5 mM EDTA, 5 mM β-ME, 1 mM PMSF, pH 8 and stirred magnetically for 16 hours at 4° C. The resulting $BLS\text{-}RR_{12}EE_{345}L$ chimera was purified under denaturalizing conditions by anionic interchange chromatography in a Q-Sepharose (Pharmacia, USA) column. The sample was eluted using a buffer 50 mM Tris/HCl, 8 M urea, pH 8.5 under a linear gradient of 0 to 1 M NaCl. The fusion protein was assayed by SDS-PAGE and light scattering analyses. See FIGS. 30 and 31.

The SDS-PAGE analysis showed that the fusion protein $BLS\text{-}RR_{12}EE_{345}L$ had a high level of purity. The molecular weight of the protein, as determined by the light scattering technique, was 224 kDa. In addition, the protein showed a high-quality CD signal in the remote UV spectrum These results suggest that the fusion protein is well folded and observes a decameric structure similar to the native BLS protein when in the presence of 8M urea. The BLS structure is distorted at room temperature when the urea concentration is decreased. This is probably due to the binding of the $RR_{12}EE_{345}L$ with itself.

2. Construction of Peptide $EE_{12}RR_{345}L$

The peptide $EE_{12}RR_{345}L$ was cloned in the C-terminal end of protein glutathione S-transferase (GST). This peptide is complementary to the $RR_{12}EE_{345}L$ peptide displayed by the BLS fusion protein. See FIG. 32.

The $EE_{12}RR_{345}L$ peptide gene was cloned in the pGEX-4T1 vector. A competent strain of *E. coli* BL21 (DE3) bacteria was transformed with the resulting vector. Afterwards, the bacteria were cultured in a LB-agar/ampicillin culture medium at 37° C. The gene expression was induced with 1 mM IPTG for 16 hours at 37° C. The bacteria were then sonicated.

The resulting $EE_{12}RR_{345}L$ peptide was purified as a GST fusion protein using a glutathione/agarose matrix. The coupled complex was set in a column and was washed with a buffer 50 mM Tris, pH 8 until the peptide was absent from the eluent. Afterwards, the matrix was incubated with thrombine for 16 hours at room temperature to cleave the $EE_{12}RR_{345}L$ from GST fusion protein. The peptide was then eluted with a buffer 50 mM Tris, pH 8 to purify it further. The resulting $EE_{12}RR_{345}L$ peptide had a high level of purity.

3. Formation of Molecular Assembly Between Fusion Protein $BLS\text{-}RR_{12}EE_{3}45L$ and Peptide $EE_{12}RR_{345}L$ One part of the fusion protein $BLS\text{-}RR_{12}EE_{345}L$ was preincubated with 8 M urea, 50 mM Tris, 0.5 M NaCl, pH 8 for 15 minutes at 30° C. Four parts of the peptide $EE_{12}RR_{345}L$ were preincubated in a buffer 50 mM Tris, 0.1 M NaCl, pH 8 for 15 minutes at 30° C. The fusion protein and peptide were mixed and incubated for 15 minutes at 30° C. The mixture remained soluble after incubation.

Figure 34:
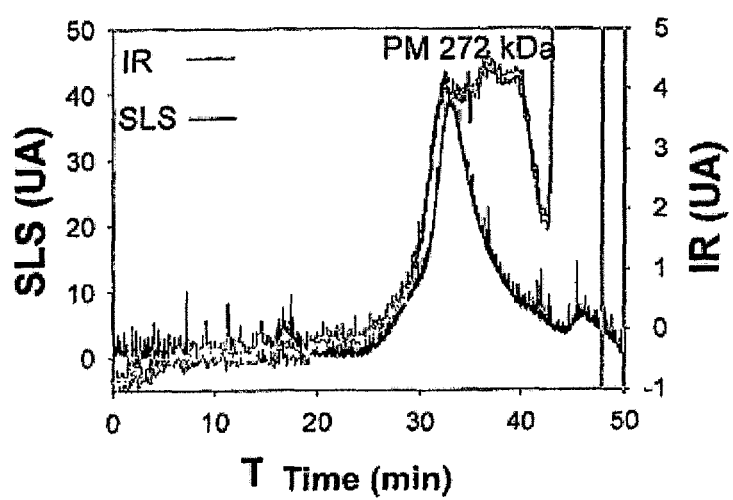
Figure 35:
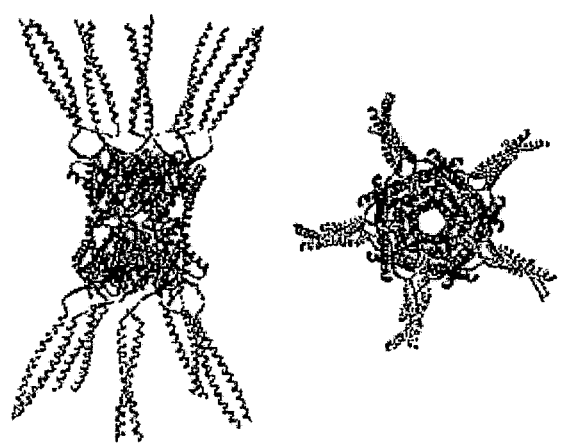

The resulting molecular assembly was assayed by light scattering analysis and its theoretical molecular weight was calculated (MW: 222.1 kDa). See FIG. 34. This analysis showed that approximately 10 $EE_{12}RR_{345}L$ peptides (MW: 5.6 kDa) coupled to the $BLS\text{-}RR_{12}EE_{345}L$ decamer (MW: 222.1 kDa). See FIG. 35.

In addition, the assembly showed a high-quality CD signal in the remote UV spectrum. These results suggest that molecular assemblies formed with modified BLS proteins using this technique are viable.

The present invention has been described in some detail and exemplified to facilitate its understanding and reproducibility. Certain changes in the form and detail can be made by anyone skilled in the art without departing from the true object and scope of the claims of the present invention. All the publications quoted herein are incorporated in their totality as references to the description of the invention.

REFERENCES

Arakawa, T., Yu, J., Chong, D., Hough, J., Engen, P. C. and Langridge, W. H. R. "A plant-based cholera toxin B subunit-insulin fusion protein protects against the development of autoimmune diabetes" Nature Biotech., 16:934-938, 1998.

Bacher A. and Fischer M. "Protein conjugates, methods, vectors, proteins and DNA for producing them, their use, and medicaments and vaccines containing a certain quantity of said protein conjugates" WO0053229.

Bachmann, M. F., Rohrer, U. H., Kundig, T. M., Burki, K., Hengartner, H. and Zinkernagel, R. M. "The influence of antigen organization on B cell responsiveness" Science, 262:1448-1451, 1993.

Baldi, P. C., Velikovsky, C., Braden, B. C., Giambartolomei, G. H., Fossati, C. A. and Goldbaum, F. A. "Structural, functional and immunological studies on a polymeric bacterial protein" Brazilian Journal of Medical and Biological Research, 33:741-747, 2000.

Baldi, P. C., Giambartolomei, G. H., Goldbaum, F. A., Abdón, L. F., Velikovsky, C. A. Kittelberger, R. and Fossati, C. A. "Humoral immune response against LPS and cytoplasmic proteins of *Brucella* in cattle vaccinated with *Brucella abortus* S19 or experimentally infected with *Yersinia enterocolitica* 0:9" Clinical Diagnostic and Laboratory Immunology, 3 (4):472-476, 1996.

Braden, B. C., Velikovsky, C. A., Cauerhff, A., Polikarpov, I. and Goldbaum, F. A. "Divergence in macromolecular assembly: X-ray crystallographic structure analysis of lumazine synthase from *Brucella abortus*" Journal of Molecular Biology, 297:1031-1036, 2000.

Domingo, G. J., Orru, S. and Perham, R. N. "Multiple display of peptides and proteins on a macromolecular scaffold derived from a multienzyme complex" Journal of Molecular Biology, 305:259-267, 2001.

Domingo, G. J., Orru, S. and Perham, R. N. "Molecular display on multimeric protein scaffolds derived from the E2 component of the alphaketoacid dehydrogenase" WO0185208.

Goldbaum, F. A., Rubbi, C. P., Wallach, J. C., Miguel, S. E., Baldi, P. C. and Fossati, C. A "Differentiation between active and inactive human brucellosis by measuring antiprotein humoral immune responses" Journal of Clinical Microbiology, 30:604-607, 1992.

Goldbaum, F. A., Leoni, J., Wallach, J. C. and Fossati, C. A. "Characterization of an 18 kDa brucella cytoplasmic protein which appears to be a serological marker of active infection of both human and bovine brucellosis" Journal of Clinical Microbiology, 31:2141-2145, 1993.

Goldbaum, F. A., Polikarpov, I., Cauerhff, A., Velikovsky, C. A., Braden B. C. and Poljak, R. J. "Crystallization and preliminary X-ray analysis of the lumazine synthase from Brucella spp." Journal of Structural Biology, 123:175-178, 1998.

Goldbaum, F. A., Velikovsky, C. A., Baldi, P. C., Mörtl, S., Bacher, A. and Fossati, C. A. "The 18 kDa cytoplasmic protein of Brucella spp. is as enzyme with lumazine synthase activity" Journal of Medical Microbiology, 48:833-839, 1999.

Huerta, M., et al. "Synthetic peptide vaccine against Taenia solium pig cysticercosis: successful vaccination in a controlled field trial in rural Mexico" Vaccine, 20:262-266, 2001.

Laemmli, U. K. "Cleavage of structural proteins during the assembly of the head of bacteriophage T4." Nature, 227 (259): 680-5, 1970.

Leclerc, C. and Ronco, J. "New approaches in vaccine development" Immunol. Today, 19(7):300-302, 1998.

Li, Y., Mui, S., Brown, J. H., Strand, J., Reshetnikova, L., Tobacman, L. S. y Cohen, C. 2002. The Crystal Structure of the C-Terminal Fragment of Striated-Muscle Alpha-Tropomyosin Reveals a Key Troponin T Recognition Site. Procedings Nacional Academy of Sciences USA, 99: 7378.

Moll, J., Ruvinov, S., Pastan, I. and Vinson, C. "Designed heterodimerizing leucine zippers with a ranger of pIs and stabilities up to $10^{-15}$ M" Protein Sci., 10:649-655, 2001.

Nieba, L. and Bachmann, M. F. "A new generation of vaccines" Moderns Aspects of Immunobiology, 1(2):36-39, 2000.

Pace, C. N. "Determination and analysis of urea and guanidine hydrochloride denaturation curves" Methods Enzymol., 131: 266-80, 1986.

Redfield, N. New England Journal of Medicine, 316:673-678, 1998.

Renner, W. A., Bachmann, M., Hennecke, F., and Nieba, L. "Ordered molecular presentation of antigens, method of preparation and use" WO0032227.

Bachmann, M., Dunant N., Sebbel, P., Tissot, A., and Lechener, F. "Molecular antigen array" WO0185208.

Ritsert, K., Huber, R., Turk, D., Ladenstein, R., Schmidt-Base, K. and Bacher, A. "Studies on the lumazine synthase/riboflavin synthase complex of Bacillus subtilis: crystal structure analysis of reconstituted, icosahedral β-subunit capsids with bound substrate analogue inhibitor at 2.4 Å resolution" Journal of Molecular Biology, 253: 151-167, 1995.

Toledo, A., et al. "Two epitopes shared by Taenia crassiceps and Taenia solium confer protection against murine T. crassiceps cysticercosis along with a prominent T1 response" Infect Immun 69:1766-1773, 2001.

Velikovsky, C. A., Cassataro, J., Sanchez, M., Fossati, C. A., Fainboim, L. and Spitz, M. "Single-shot plasmid DNA intrasplenic immunization for the production of monoclonal antibodies" Persistent Expression of DNA, J. Immunol. Meth., 244(1-2):1-7, 2000b.

What is claimed is:

1. Isolated chimeric proteins comprising a peptide, a polypeptide or a proteic domain linked to a modified lumazine synthase protein from *Brucella* spp, wherein either the first 8 N-terminal residues of the modified protein have been deleted or the nucleotide sequences encoding the first 8 N-termini residues of the modified protein are replaced with DNA sequences comprising restriction sites for enzymes Nsi I and Afl II, wherein the amino acid sequence of the modified protein consists of SEQ ID NO:7.

2. The isolated chimeric proteins, according to claim 1, wherein the linked peptide, polypeptide or proteic domain is homologous or heterologous.

3. The isolated chimeric proteins, according to claim 1, wherein the linked peptide, polypeptide or proteic domain is an antigen, toxin, agent or segment thereof, capable of inducing an immune response in an eukaryotic organism.

4. The isolated chimeric proteins, according to claim 3, wherein the linked peptide, polypeptide or proteic domain is an antigen, toxin, agent or segment thereof of bacterial, viral or parasitic origin.

5. The isolated chimeric proteins, according to claim 3, wherein the antigen is the Outer-membrane protein from *Brucella melitensis* fused to *Brucella* spp. lumazine synthase (BLS-OMP31) or functional segments thereof.

6. The isolated chimeric proteins, according to claim 3, wherein the antigen is the *Taenia crassiceps* recombinant antigen fused to *Brucella* spp. lumazine synthase (BLS-KETc 1) or functional segments thereof.

7. The isolated chimeric proteins, according to claim 3, wherein the antigen is murine Staufen-1 double-stranded RNA-binding domain 3 fused to *Brucella* spp. lumazine synthase (BLS-RBD3) or functional segments thereof.

8. The isolated chimeric proteins, according to claim 3, wherein the immune response is humoral or cellular.

9. The isolated chimeric proteins, according to claim 3, wherein the eukaryotic organism is a bird, fish or mammal.

10. The isolated chimeric proteins, according to claim 9, wherein the eukaryotic organism is a mammal.

11. The isolated chimeric proteins, according to claim 10, wherein the mammal is a human, a rabbit or a mouse.

12. The isolated chimeric proteins, according to claim 3, wherein the linked peptide, polypeptide or proteic domain is an antigen, toxin, agent or segment thereof which induces an immune response in vitro or in vivo.

13. The combination of two or more isolated chimeric proteins, according to claim 1, wherein the peptides, polypeptides or proteic domains linked to each modified protein are different.

14. The combination of two or more isolated chimeric proteins, according to claim 1, wherein the peptides, polypeptides or proteic domains linked to each modified protein are identical.

15. The combination of one or more isolated chimeric proteins, according to claim 1.

16. A pharmaceutical composition comprising at least one of the isolated chimeric proteins according to claim 1.

17. A pharmaceutical composition, according to claim 16, comprising an acceptable pharmaceutical excipient.

18. A pharmaceutical composition, according to claim 17, wherein the acceptable pharmaceutical excipient is an adjuvant.

19. A pharmaceutical composition, according to claim 18, wherein the adjuvant comprises a Freund's adjuvant, a MDP dipeptide, saponin, tyrosine stearate, aluminum hydroxide, lymph cytokines, the native protein of lumazine synthase of *Brucella* spp or the modified proteins of lumazine synthase of *Brucella* spp.

20. A pharmaceutical composition comprising at least one of the isolated chimeric proteins according to claim 1.

21. A pharmaceutical composition, according to claim 20, comprising an acceptable pharmaceutical excipient.

22. A pharmaceutical composition, according to claim 21, wherein the acceptable pharmaceutical excipient is an adjuvant.

23. A pharmaceutical composition, according to claim 22, wherein the adjuvant comprises a Freund's adjuvant, a MDP dipeptide, saponin, tyrosine stearate, aluminum hydroxide, lymph cytokines, the native protein of lumazine synthase of *Brucella* spp or the modified proteins of lumazine synthase of *Brucella* spp.

24. A biosensor comprising a base attached to at least one isolated chimeric protein of claim 1, wherein said base is connected to a means for measuring the interaction of a ligand with said isolated chimeric protein.

25. A biosensor, according to claim 24, wherein the ligand is an antibody.

26. Protein conjugates comprising a ligand linked to the peptide, polypeptide or proteic domain connected to the modified proteins of lumazine synthase of *Brucella* spp. according to claim 1.

27. The protein conjugates according to claim 26, wherein the ligand is linked to the peptide by a covalent bond.

28. The protein conjugates, according to claim 26, wherein the link is non-covalent.

29. The protein conjugates according to claim 26, wherein the ligand and the chimeric protein are linked through connecting sequences of a heterodimerization domain.

30. The isolated chimeric proteins according to claim 1, wherein their quaternary structure is a decamer.

31. The protein conjugates according to claim 26, wherein the ligand is linked to the peptide by a peptide bond.

32. The protein conjugates according to claim 26, wherein the ligand and the chimeric protein are linked through connecting sequences encoding a leucine zipper.

33. A method to induce an immune response in an eukaryotic organism comprising the administration of an effective amount of a pharmaceutical composition according to claim 16 to the organism.

34. A method, according to claim 33, wherein the immune response is humoral or cellular.

35. A method, according to claim 33, wherein the pharmaceutical composition is administered simultaneously or sequentially.

36. A method, according to claim 33, wherein the eukaryotic organism is a bird, fish or mammal.

37. A method, according to claim 33, wherein the eukaryotic organism is a mammal.

38. A method, according to claim 37, wherein the mammal is a human, a rabbit or a mouse.

39. A method, according to claim 33, wherein the pharmaceutical composition is administered by a subcutaneous, intravenous, intraperitoneal, intramuscular, oral or nasal routes or through a needle-free injection system.

* * * * *

UNITED STATES PATENT AND TRADEMARK OFFICE
CERTIFICATE OF CORRECTION

PATENT NO.       : 8,685,670 B2                           Page 1 of 2
APPLICATION NO.  : 11/569957
DATED            : April 1, 2014
INVENTOR(S)      : Fernando Goldbaum et al.

It is certified that error appears in the above-identified patent and that said Letters Patent is hereby corrected as shown below:

Delete Title Page, and replace with new Title Page. (attached)

In the Claims

Cancel claims 20-23 at column 80, lines 17-29 of the patent.

Signed and Sealed this
First Day of July, 2014

Michelle K. Lee
*Deputy Director of the United States Patent and Trademark Office*

(12) United States Patent
Goldbaum et al.

(10) Patent No.: US 8,685,670 B2
(45) Date of Patent: Apr. 1, 2014

(54) ISOLATED CHIMERIC PROTEINS OF MODIFIED LUMAZINE SYNTHASE

(75) Inventors: Fernando Alberto Goldbaum, Buenos Aires (AR); Diego Andrés Laplagne, Buenos Aires (AR); Vanesa Zylberman, Buenos Aires (AR); Patricio Craig, Buenos Aires (AR); Paula Mercedes Berguer, Buenos Aires (AR); Natalia Ainciart, Buenos Aires (AR); Carlos Alberto Fossati, La Plata (AR); Carlos Alejandro Velikovsky, Buenos Aires (AR); Juliana Cassataro, Buenos Aires (AR); Guillermo Giambartolomei, Buenos Aires (AR)

(73) Assignee: Goldgene LLC, Buenos Aires (AR)

(*) Notice: Subject to any disclaimer, the term of this patent is extended or adjusted under 35 U.S.C. 154(b) by 1367 days.

(21) Appl. No.: 11/569,957

(22) PCT Filed: Jun. 3, 2005

(86) PCT No.: PCT/US2005/019289
§ 371 (c)(1),
(2), (4) Date: Mar. 17, 2008

(87) PCT Pub. No.: WO2005/121330
PCT Pub. Date: Dec. 22, 2005

(65) Prior Publication Data
US 2009/0087435 A1 Apr. 2, 2009

(30) Foreign Application Priority Data
Jun. 3, 2004 (AR) .............................. P040101923

(51) Int. Cl.
C12P 21/04 (2006.01)
C12N 9/00 (2006.01)
C12N 1/20 (2006.01)
C12N 15/00 (2006.01)
A61K 38/00 (2006.01)
A61K 39/00 (2006.01)
A61K 39/02 (2006.01)
C07H 21/04 (2006.01)

(52) U.S. Cl.
USPC ................. 435/69.7; 435/183; 435/252.33; 435/320.1; 424/184.1; 424/190.1; 424/194.1; 514/1.1; 536/23.2

(58) Field of Classification Search
None
See application file for complete search history.

(56) References Cited

U.S. PATENT DOCUMENTS

2004/0014158 A1* 1/2004 Bacher et al. ............... 435/8
2004/0213808 A1* 10/2004 Lieberman et al. ......... 424/218.1

FOREIGN PATENT DOCUMENTS

| WO | 00/32227 A2 | 6/2000 |
| WO | 00/53229 A2 | 9/2000 |
| WO | 01/42439 A1 | 6/2001 |
| WO | 01/85208 A2 | 11/2001 |

OTHER PUBLICATIONS

Laplagne et al. Engineering of a polymeric bacterial protein as a scaffold for the multiple display of peptides, Proteins. Dec. 1, 2004;57(4):820-8.*
Sciutto et al. *Brucella* spp. lumazine synthase: a novel antigen delivery system, Vaccine. Apr. 15, 2005; 23(21): 2784-90.*
Mahairas et al. J Bacteriol. Mar. 1996;178(5):1274-82.*
Whisstock et al. Quaterly Reviews of Biophysics, 2003, "Prediction of protein function from protein sequence and structure", 36(3): 307-340.*
Sciutto et al. New approaches to improve a peptide vaccine against porcine *Taenia solium* cysticercosis, Archives of Med Res 33, 371-378, 2002, Review.*
Estein et al. The recombinant Omp31 from *Brucella melitensis* alone or associated with rough lipopolysaccharide induces protection against *Brucella ovis* infection in BALB/c mice, Microbes Infect. Feb. 2003;5(2):85-93.*
Arakawa Takeshi et al., "A plant-based cholera toxin B subunit-insulin fusion protein protects against the development of autoimmune diabetes", Nature Biotechnology., vol. 16, pp. 934-938, Oct. 1998.
Bachmann, Martin F. et al., "The Influence of Antigen Organization on B Cell Rresponsiveness", Science, vol. 262, pp. 1448-1451, Nov. 1993.
Baldi, Pablo. C. et al., "Humoral Immune Response against Lipolysaccharide and Cytoplasmic Proteins of *Brucella abortus* in Cattle Vaccinated with *B. abortus* S19 or Experimentally Infected with *Yersinia enterocolitica* Serotype 0:9", Clinical and Diagnostic and Laboratory Immunology, vol. 3, No. 4, pp. 472-476, Jul. 1996.
Baldi, P.C. et al., "Structural, functional and immunological studies on a polymeric bacterial protein", Brazilian Journal of Medical and Biological Research, vol. 33, pp. 741-747, 2000.

(Continued)

Primary Examiner — Iqbal H Chowdhury
(74) Attorney, Agent, or Firm — Sughrue Mion, PLLC

(57) ABSTRACT

Isolated chimeric proteins including up to ten copies of peptides, polypeptides or protein domains inserted in the amino termini of the *Brucella* spp. Lumazine synthase enzyme. Isolated nucleotide sequences codifying the chimeric proteins. Vectors, plasmids and transformed cells used for expressing the proteins. Monoclonal and polyclonal antibodies induced by the chimeric proteins. Hybridomas producing the monoclonal antibodies. Vaccines and pharmaceutical compounds including the chimeric proteins, nucleotide sequences and antibodies. A method to induce an immune response in higher organisms including the administration of effective amounts of the vaccines and pharmaceutical compounds. Biosensors including the chimeric proteins. Protein conjugates formed by the chimeric proteins and a ligand bound by means of covalent and noncovalent bonds. Uses of the chimeric proteins, nucleotide sequences, vectors, plasmids, transformed cells, antibodies, hybridomas, conjugates, biosensors, vaccines and pharmaceutical compounds. The quaternary structure of the chimeric proteins.

35 Claims, 42 Drawing Sheets